(12) United States Patent
Adam et al.

(10) Patent No.: US 8,318,159 B2
(45) Date of Patent: Nov. 27, 2012

(54) ANTI-IGF ANTIBODIES

(75) Inventors: Paul Adam, Vienna (AT); Eric Borges, Maria Enzersdorf (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 68 days.

(21) Appl. No.: 12/636,195

(22) Filed: Dec. 11, 2009

(65) Prior Publication Data
US 2010/0150940 A1 Jun. 17, 2010

(30) Foreign Application Priority Data
Dec. 12, 2008 (EP) .................................... 08171554

(51) Int. Cl.
*A61K 39/395* (2006.01)
*C07K 16/26* (2006.01)
(52) U.S. Cl. ............. 424/130.1; 530/387.9; 530/388.24; 424/133.1; 424/139.1; 424/140.1; 424/145.1
(58) Field of Classification Search .......................... None
See application file for complete search history.

(56) References Cited

U.S. PATENT DOCUMENTS

| | | | |
|---|---|---|---|
| 3,773,919 | A | 11/1973 | Boswell et al. |
| 4,342,566 | A | 8/1982 | Theofilopoulos et al. |
| 6,342,221 | B1 | 1/2002 | Thorpe et al. |
| 6,696,245 | B2 | 2/2004 | Winter et al. |
| 6,991,790 | B1 | 1/2006 | Lam et al. |
| 7,020,563 | B1 | 3/2006 | Bentley et al. |
| 7,037,498 | B2 | 5/2006 | Cohen et al. |
| 7,060,268 | B2 | 6/2006 | Andya et al. |
| 7,438,911 | B2 | 10/2008 | Shitara et al. |
| 7,498,415 | B2 | 3/2009 | Shitara et al. |
| 7,749,966 | B2 | 7/2010 | Raso |
| 2006/0165695 | A1 | 7/2006 | Shitara et al. |
| 2007/0196376 | A1 | 8/2007 | Raeber et al. |
| 2009/0016967 | A1 | 1/2009 | Schnapp et al. |
| 2010/0099147 | A1 | 4/2010 | Hariharan et al. |
| 2010/0196395 | A1 | 8/2010 | Adam et al. |

FOREIGN PATENT DOCUMENTS

| | | |
|---|---|---|
| CA | 2473039 A1 | 7/2003 |
| CA | 2483848 A1 | 11/2003 |
| CA | 2536288 A1 | 3/2005 |
| CA | 2540133 A1 | 3/2005 |
| CA | 2540138 A1 | 3/2005 |
| EP | 0123228 A2 | 10/1984 |
| EP | 0292656 A1 | 11/1988 |
| EP | 0492552 A1 | 7/1992 |
| EP | 0700994 A1 | 3/1996 |
| EP | 1505075 A1 | 2/2005 |
| JP | 2003310275 A | 11/2003 |
| WO | 8500831 A1 | 2/1985 |
| WO | 8911297 A1 | 11/1989 |
| WO | 9000562 A1 | 1/1990 |
| WO | 9429348 A2 | 12/1994 |
| WO | 9525794 A1 | 9/1995 |
| WO | 9928347 A1 | 6/1999 |
| WO | 02053596 A2 | 7/2002 |
| WO | 02056910 A1 | 7/2002 |
| WO | 03002609 A2 | 1/2003 |
| WO | 03050531 A2 | 6/2003 |
| WO | 03059951 A2 | 7/2003 |
| WO | 03093317 A1 | 11/2003 |
| WO | 03100008 A2 | 12/2003 |
| WO | 03106621 A2 | 12/2003 |
| WO | 2004003019 A2 | 1/2004 |
| WO | 2004058821 A2 | 7/2004 |
| WO | 2004071529 A2 | 8/2004 |
| WO | 2004083248 A1 | 9/2004 |
| WO | 2005005635 A2 | 1/2005 |
| WO | 2005016970 A2 | 2/2005 |
| WO | 2005018671 A1 | 3/2005 |
| WO | 2005027970 A1 | 3/2005 |
| WO | 2005028515 A1 | 3/2005 |
| WO | 2005058967 A2 | 6/2005 |
| WO | 2005061541 A1 | 7/2005 |
| WO | 2006008639 A1 | 1/2006 |
| WO | 2006069202 A2 | 6/2006 |
| WO | 2006125640 A2 | 11/2006 |
| WO | 2007012614 A2 | 2/2007 |
| WO | 2007042309 A2 | 4/2007 |
| WO | 2007070432 A2 | 6/2007 |
| WO | 2007115814 A2 | 10/2007 |
| WO | 2007118214 A2 | 10/2007 |

(Continued)

OTHER PUBLICATIONS

Sell, Christian, et al; Effect of a Null Mutation of the Insulin-Like Growth Factor I Receptor Gene on Growth and Transformation of Mouse Embryo Fibroblasts; Molecular and Cellular Biology (1994) vol. 14, No. 6 pp. 3604-3612.

Sell, Christian, et al; Simian Virus 40 Large Tumor Antigen is Unable to Transform Mouse Embryonic Fibroblasts lacking Type 1 Insulin-Like Growth Factor Receptor; Proc. Natl. Acad. Sci. USA vol. 90 pp. 11217-11221, 1993.

Shukla, Abhinav, A., et al; Downstream Processing of Monoclonal Antibodies—Application of Platform Approaches; Journal of Chromatography (2007) vol. 848 pp. 28-39.

Srinivasan, Mythily, et al; Immunomodulatory Peptides From IgSF Proteins: A Review; Current Protein and Peptide Science (2005) vol. 6, No. 2 pp. 185-196.

Strumberg, Dirk; Preclinical and Clinical Development of the Oral Multikinase Inhibitor Sorafenib in Cancer Treatment; Drugs of Today (2005) vol. 41, No. 12 pp. 773-784.

Takanami, Iwao, et al; Insulin-Like Growth Factor-II as a Prognostic Factor in Pulmonary Adenocarcinoma; Journal of Surgical Oncology (1996) vol. 61 pp. 205-208.

Tsai, J. F., et al; Serum Insulin-Like Growth Factor-II as a Serologic Marker of Small Hepatollular Carcinoma: Scandinavian Journal of Gastroenterology (2005) vol. 40 pp. 68-75.

(Continued)

*Primary Examiner* — Marianne P Allen
(74) *Attorney, Agent, or Firm* — Michael P. Morris; Edouard G. Lebel

(57) ABSTRACT

Antibody molecules, in particular fully human antibodies that bind to human IGF-1 and cross-react with IGF-2 such that binding of IGF-1 and IGF-2 to the IGF-1 receptor is prevented and IGF-1 receptor-mediated signaling is inhibited. The antibodies do not bind to insulin and thus do not affect the mitogenic properties of insulin that are mediated by its binding to the insulin receptors. The antibodies are useful for the treatment of hyperproliferative diseases, in particular cancer.

13 Claims, 25 Drawing Sheets

FOREIGN PATENT DOCUMENTS

| | | | |
|---|---|---|---|
| WO | 2007126876 A2 | 11/2007 | |
| WO | 2007141626 A1 | 12/2007 | |
| WO | 2008005469 A2 | 1/2008 | |
| WO | 2008079324 A1 | 7/2008 | |
| WO | 2008079849 A2 | 7/2008 | |
| WO | 2008098917 A2 | 8/2008 | |
| WO | 2008108986 A2 | 9/2008 | |
| WO | 2008115470 A2 | 9/2008 | |
| WO | 2008116103 A2 | 9/2008 | |
| WO | 2008144345 A2 | 11/2008 | |
| WO | 2008144720 A2 | 11/2008 | |
| WO | 2008152422 A2 | 12/2008 | |
| WO | 2008155387 A2 | 12/2008 | |
| WO | WO 2008/155387 | * | 12/2008 |
| WO | 2009005673 A1 | 1/2009 | |
| WO | 2009006336 A1 | 1/2009 | |
| WO | 2009016164 A1 | 2/2009 | |
| WO | 2009017679 A2 | 2/2009 | |
| WO | 2009019117 A1 | 2/2009 | |
| WO | 2009021054 A2 | 2/2009 | |
| WO | 2009032145 A1 | 3/2009 | |
| WO | 2009032782 A2 | 3/2009 | |
| WO | 2009039457 A1 | 3/2009 | |
| WO | 2009045361 A2 | 4/2009 | |
| WO | 2009045389 A2 | 4/2009 | |
| WO | 2009079587 A2 | 6/2009 | |
| WO | 2009120767 A1 | 10/2009 | |
| WO | 2009126304 A1 | 10/2009 | |
| WO | 2009137378 A2 | 11/2009 | |
| WO | 2009137758 A2 | 11/2009 | |
| WO | 2009149185 A2 | 12/2009 | |
| WO | 2010034441 A1 | 4/2010 | |
| WO | 2010036767 A1 | 4/2010 | |
| WO | 2010045315 A1 | 4/2010 | |
| WO | 2010048123 A2 | 4/2010 | |
| WO | 2010052344 A2 | 5/2010 | |
| WO | 2010062896 A1 | 6/2010 | |
| WO | 2010066868 A2 | 6/2010 | |
| WO | 2010069858 A1 | 6/2010 | |
| WO | 2010075511 A1 | 7/2010 | |

OTHER PUBLICATIONS

Wang, Zheng, et al; Expression of IGF-II in Early Experimental Hepatocellular Carcinomas and its Significance in Early Diagnosis; World Journal of Gastroenterology (2003) vol. 9 pages 267-270.

Woodson, Karen, et al; Loss of Insulin-Like Growth Factor-II Imprinting and the Presence of Screen-Detected Colorectal Adenomas in Women; Journal of the National Cancer Institute (2004) vol. 96, No. 5 pages 407-410.

Yao, Xiaoming, et al; A Methylated Oligonucleotide Inhibits IGF2 Expression and Enhances Survival in a Model of Hepatocellular Carcinoma; The Journal of Clinical Investigation (2003) vol. 111, No. 2 pp. 265-273.

Yao, Xiaoming, et al; A Novel Orthotopic Tumor Model to Study Growth Factors and Oncogenes in Hepatocarcinogenesis; Clinical Cancer Research (2003) vol. 9 pp. 2719-2726.

Yelton, Dale, E. et al; Affinity Maturation of the BR96 Anti-Carcinoma Antibody by Codon-Based Mutagenesis; The American Association of Immunologists (1995) vol. 155 pp. 1994-2004.

Zapata, Gerardo, et al; Engineering Linear F(ab')2 Fragments for Efficient Production in *Escherichia coli* and Enhanced Antiproliferative Activity; Protein Engineering (1995) vol. 8, No. 10 pp. 1057-1062.

Zhao, Ronghua, et al; Positive Correlation of Insulin-Like Growth Factor-II with Proliferating Cell Index in Patients with Colorectal Neoplasia; Cancer Epidemiology, Biomarkers and Prevention (2005) vol. 14 pp. 1819-1822.

Barbas, Carlos F., et al; In Vitro evolution of a Neutralizing Human Antibody to Human Immunodeficiency Virus Type 1 to Enhance Affinity and Broaden Strain Cross-Reactivity; Proc. Natl. Acad. Sci. USA (1994) vol. 91 pp. 3809-1813.

Burtrum, Douglas, et al; A Fully Human Monoclonal Antibody to the Insulin-Like Growth Factor I Receptor Blocks Ligand-dependent Signaling and Inhibits Human Tumor Growth in Vivo; Cancer Research (2003) vol. 63 pp. 8912-8921.

Cascieri, Margaret, A., et al; Identification of the Insulin-Like Growth Factor I (IGF I) Epitopes Recognized by Monoclonal and Polyclonal Antibodies to IGF I; Endocrinology (1990) vol. 126, No. 6 pp. 2773-2777.

Chen, Jian-Wen, et al; Free Rather than Total Circulating Insulin-Like Growth Factor-I Determines the Feedback on Growth Hormone Release in Normal Subjects; The Journal of Clinical Endocrinology & Metabolism (2005) vol. 90, No. 1 pp. 366-371.

Chothia, Cyrus, et al; Canonical Structures for the Hypervariable Regions of Immunoglobulins; Journal Molecular Biology (1987) vol. 196 pp. 901-917.

Cruz-Correa, M., et al; IGF2 Loss of Imprinting: A Potential Heritable Risk Factor for Colorectal Cancer; Gastroenterology (2004) vol. 126 pp. 1190-1201.

Cui, Hengmi, et al; Loss of IGF2 Imprinting: A Potential Marker of Colorectal Cancer Risk; Science (2003) vol. 299 pp. 1753-1755.

Dufner, Almut, et al; Ribosomal S6 Kinase Signaling and the Control of Translation; Experimental Cell Research (1999) vol. 253 pp. 100-109.

Feng, Yang, et al; Novel Human Monoclonal Antibodies to Insulin-Like Growth Factor (IGF)-II That Potently Inhibit the IGF Receptor Type I Signal Transduction Function; Molecular Cancer Therapy (2006) vol. 5, No. 1 pp. 114-120.

Frasca, F., et al; Insulin Receptor Isoform A, a Newly Recognized, High-Affinity Insulin-Like Growth Factor II Receptor in Fetal and Cancer Cells; Molecular and Cellular Biology (1999) vol. 19, No. 5 pp. 3278-3288.

Freier, S., et al; Expression of the Insulin-Like Growth Factors and their Receptors in Adenocarcinoma of the Colon; Gut (1999) vol. 44 pp. 704-708.

Fukuzawa, Ryuji, et al; High Frequency of Inactivation of the Imprinted H19 gene in "Sporadic" Hepatoblastoma; International Journal of Cancer (1999) vol. 82 pp. 490-497.

Goetsch, Liliane, et al; A Recombinant Humanized Anti-Insulin-Like Growth Factor Receptor Type I Antibody (h7C10) Enhances the Antitumor Activity of Vinorelbine and Anti-Epidermal Growth Factor Receptor Therapy Against Human Cancer Xenografts; International Journal of Cancer (2005) vol. 113 pp. 316-328.

Goya, Masato, et al; Growth Inhibition of Human Prostate Cancer Cells in Human Adult Bone implanted into Nonobese Diabetic/Severe Combined Immunodeficient Mice by a Ligand-Specific Antibody to Human Insulin-Like Growth Factors; Cancer Research, American Association for Cancer Research (2004) vol. 64, No. 17 pp. 6252-6258.

Haenel, Cornelia et al; Characterization of High-Affinity Anitbodies by Electrochemiluminescense-Based Equilibrium Titration; (Analytical Biochemistry (2005) vol. 339 pp. 182-184.

Hassan, A. Bassim., et al; Insulin-Like Growth factor II Supply Modifies growth of Intestinal Adenoma in ApcMin/+Mice1; Cancer Research (2000) vol. 60 pp. 1070-1076.

Hawkins, Robert E., et al; Selection of Phage Antibodies by Binding Affinity Mimicking Affinity Maturation; Journal Mol. Biol. (1992) vol. 226 pp. 889-896.

Jackson, Jeffrey R., et al; In Vitro Antibody Maturation: Improvement of High Affinity, Neutraizing Antibody Against IL-1b; Journal of Immunology (1995) vol. 154, No. 7 pp. 3310-3319.

Jerome L, et al; Deregulation of the IGF Axis in Cancer: Epidemiological Evidence and Potential Therapeutic Interventions; Endocrine-Related Cancer (2003) vol. 10 pp. 561-578.

Kipriyanov, Sergey M., et al; Generation and Production of Engineered Antibodies; Molecular Biotechnology (2004) vol. 26 pp. 39-60.

Knappik, Achim, et al; Fully Synthetic Human Combinatorial Antibody Libraries (HuCAL) Based on Modular Consensus Frameworks and CDRs Randomized with Trinucleotides; Journal Molecular Biology (2000) vol. 296 pp. 57-86.

Kolb, E. Anders, et al; Initial Testing (Stage 1) of a Monoclonal Antibody (SCH 717454) Against the IGF-1 Receptor by the Pediatric Preclinical Testing Program; Pediatr Blood Cancer (2008) vol. 50 pp. 1190-1197.

Kulik, George et al; Antiapoptotic Signalling by the Insulin-Like Growth Factor I receptor, Phosphatidylinositol 3-Kinase, and AKt; Molecular and Cellular Biology (1997) vol. 17, No. 3 pp. 1595-1606.

Leroith, Derek; The Insulin-Like Growth Factor System; Experimental Diab. Res. (2003) vol. 4 pp. 205-212.

Li, Shu-Rui, et al; Differential Expression Patterns of the Insulin-Like Growth Factor 2 Gene in Human Colorectal Cancer; Tumor Biology (2004) vol. 25 pp. 62-68.

Lin, Yvonne, S., et al; Preclinical Pharmacokinetics, Interspecies scaling, and Tissue Distribution of a Humanized Monoclonal Antibody Against Vascular endothelial growth Factor; The Journal of Pharmacology and Experimental Thepapeutics (1999) vol. 288 pp. 371-378.

Lowman, Henry, B., et al; Selecting High-Affiniy Binding Proteins by Monovalent Phage Display; Biochemistry (1991) vol. 30, No. 45 pp. 10832-10837.

Lund, Per, et al; Autocrine Inhibition of Chemotherapy Response in Human Liver Tumor Cells by Insulin-Like Growth Factor-II; Cancer Letters (2004) vol. 206 pp. 85-96.

Manara, Maria C., et al; Preclinical in Vivo Study of New Insulin-Like Growth Factor-I Receptor-Specific Inhibitor in Ewing's Sarcoma; Clinical Cancer Research (2007) vol. 13, No. 4 pp. 1322-1330.

Manes, Santos, et al; Functional Epitope Mapping of Insulin-Like Growth Factor I (IGF-I) by Anti-IGF-I Monoclonal Antibodies; Endocrinology (1997) vol. 138, No. 3 pp. 905-915.

Manes, Santos, et al; Physical Mapping of Human Insulin-Like Growth Factor-I Using Specific Monoclonal Antibodies; Journal of endocrinology (1997) vol. 154 pp. 293-302.

Marks, James D., et al; By-Passing Immunization: Building High Affinity Human Antibodies by Chain Shuffling; Bio/Technology (1992) vol. 10 779-783.

Miyamoto, Shin'Ichi, et al; Blockade of Paracrine Supply of Insulin-Like Growth Factors Using Neutralizing Antibodies Suppresses the Liver Metastasis of Human Colorectal Cancers; Clin Cancer Research (2005) vol. 11, No. 9 pp. 3494-3502.

Moorehead, Roger A., et al; Transgenic Overexpression of IGF-II Induces Spontaneous Lung Tumors: A Model for Human Lung Adenocarcinoma: Oncogene (2003) vol. 22 pp. 853-857.

Nagy, Zoltan A., et al; Fully Human, HLA-DR-Specific Monoclonal Anitbodies efficiently Induce Programmed Death of Malignant Lymphoid Cells; Nature Medicine (2002) vol. 8, Issue 8 pp. 801-807.

Ng, Irene OL, et al; "Hepatocellular Carcinoma Expression of Insulin-Like Growth Factor II mRNA in Hepatocellular Carcinoma" Journal of Gastroenterology and Hepatology (1998) vol. 13, p. 152-157.

Pandini, Giuseppe, et al.; "Insulin/Insulin-like Growth Factor I Hybrid Receptors Have Different Biological Characteristics Depending on the Insulin Receptor Isoform Involved"; The Journal of Biological Chemistry; (2002) V. 277, Issue: 42, pp. 39684-39695.

Pollak, M.N., et al; Pharmacodynamic Properties of the Anti-IGF-IR Monoclonal Antibody CP-751,871 in Cancer Patients; American Society of Clinical Oncology (ASCO) vol. 25, No. 18S p. 3587, 2007.

Pollak, Michael N. et al.; "Insulin-Like Growth Factors and Neoplasia" Nature Reviews Cancer, (2004) vol. 4, pp. 505-518.

Quinn Kathryn A., et al; insulin-Like Growth Factor Expression in Human Cancer Cell Lines; The Journal of Biological Chemistry (1996) vol. 271, No. 19 pp. 11477-11483.

Rauchenberger, Robert, et al; Human Combinatorial Fab Library Yielding Specific and Functional Antibodies Against the Human Fibroblast Growth Factor Receptor 3*; The Journal of Biological Chemistry (2003) vol. 278, No. 40 pp. 38194-38205.

Renehan, Andrew, G., et al; Circulating Insulin-Like Growth Factor II and Colorectal Adenomas; The Journal of Clinical Endocrinology and Metabolism (2000) vol. 85, No. 9 pp. 3402-3408.

Renehan, Andrew, G., et al; Elevated Serum Insulin-Like Growth Factor (IGF)-II and IGF Binding Protein-2 in Patients with Colorectal Cancer; British Journal of Cancer (2000) vol. 83, No. 10 pp. 1344-1350.

Revets, Hilde, et al; Nanobodies as Novel Agents for Cancer Therapy; Experts Opin. Biol. Ther. (2005) vol. 5, No. 1 pp. 111-124.

Rubin, Raphael, et al; Biology of Disease: Insulin-Like Growth Factor-I Receptor; Laboratory Investigation (1995) vol. 73, No. 3 pp. 311-331.

Rusell, William, E., et al; Inhibition of the Mitogenic Effects of Plasma by a Monoclonal Antibody to Somatomedin C; Proc. Natl. Acad. Sci. USA (1984) vol. 81 pp. 2389-2392.

Schier, Robert, et al; Identification of Functional and Structural Amino-Acid residues by Parsimonious Mutagenesis; Gene (1996) vol. 169 pp. 147-155.

Scotlandi, Katia, et al; Insulin-like Growth Factor I Receptor-Mediated Circuit in Ewing's Sarcoma/Peripheral Neuroectodermal Tumor: A Possible Therapeutic Target; Cancer Research (1996) vol. 56 pp. 4570-4574.

Reinberg, Steven "Rare Gene Mutation Plays Role in Longevity" Healthday News, published by US News & World Report, Mar. 4, 2008; pp. 1-3.

Green, Larry L. "Antibody engineering via genetic engineering of the mouse: XenoMouse strains are a vehicle for the facile generation of therapeutic human monoclonal antibodies" Journal of Immunological Methods; 231, (1991) 11-23.

Jirtle Randy L. "IGF2 Loss of Imprinting: A Potential Heritable Risk Factor for Colorectal Cancer"; Gastroenterology (2004) vol. 126 pp. 1190-1201.

Krebs, Barbara, et al "High-throughput generation and engineering of recombinant human antibodies" Journal of Immunological Methods 254 (2001) pp. 67-84.

Casset, Florence et al. "A peptide mimetic of an anti-CD4 monoclonal antibody by rational design" Biochemical and Biophysical Research Communications, (2003) vol. 307, pp. 198-205.

Chen, Yvonne, et al. "Selection and Analysis of an Optimized Anti-VEGF Antibody: Crystal Structure of an Affinity-matured Fab in Complex with Antigen" Journal of Molecular Biology, (1999) vol. 293, pp. 865-881.

De Pascalis, Roberto, et al. "Grafting of "Abbreviated" Complementarity-Determining Regions Containing Specificity-Determining Residues Essential for Ligand Contact to Engineer a Less Immunogenic Humanized Monoclonal Antibody" The Journal of Immunology (2002) vol. 169 pp. 3076-3084.

Green, Larry L. "Antibody engineering via genetic engineering of the mouse: XenoMouse strains are a vehicle for the facile generation of therapeutic human monoclonal antibodies" Journal of Immunological Methods, (1999) vol. 231, pp. 11-23.

MacCallum, Robert M. et al. "Antibody-antigen Interactions: Contact Analysis and Binding Site Topography" Journal of Molecular Biology (1996) vol. 262, pp. 732-745.

Rudikoff, Stuart et al. "Single Amino Acid Substitution Altering Antigen-Binding Specificity" Proc. Natl. Acad. Sci. USA (1982) vol. 79, pp. 1979-1983.

Wu, Henry, et al "Humanization of a Murine Monoclonal Antibody by Simultaneous Optimization of Framework and CDR Residues" (1999) Journal of Molecular Biology vol. 294, pp. 151-162.

* cited by examiner

GPETLCGAELVDALQFVCGDRGFYFNKPTGYGSSSRRAPQ
TGIVDECCFRSCDLRRLEMYCAPLKPAKSA

60814

VH3 Amino Acid Sequence:

QVELVESGGGLVQPGGSLRLSCAASGFTFSNYWMHWVRQAPGKGLEWVSGISGWSSWTYYADSVKGRFT
ISRDNSKNTLYLQMNSLRAEDTAVYYCARFGIDAYTKVYFDYWGQGTLVTVSS

VH3 DNA Sequence:

CAGGTGGAATTGGTGGAAAGCGGCGGCGGCCTGGTGCAACCGGGCGGCAGCCTGCGTCTGAGCTGCGCGGCCTCCGGATT
TACCTTTTCTAATTATTGGATGCATTGGGTGCGCCAAGCCCCTGGAAGGGTCTCGAGTGGGTGAGCGGTATCTCTGGTT
GGTCTAGCTGGACCTATTATGCGGATAGCGTGAAAGGCCGTTTTACCATTTCACGTGATAATTCGAAAAACACCCTGTAT
CTGCAAATGAACAGCCTGCGTGCGGAAGATACGGCCGTGTATTATTGCGCGCGTTTTGGTATTGATGCTTATACTAAGGT
TTATTTTGATTATTGGGGCCAAGGCACCCTGGTGACGGTTAGCTCA

60814

Vλ3 Amino Acid Sequence:

DIELTQPPSVSVAPGQTARISCSGDNIPLKYVSWYQQKPGQAPVLVIHDDNKRPSGIPERFSGSNSGN
TATLTISGTQAEDEADYYCSSWDTLDIFNVFGGGTKLTVLG(Q)

Vλ3 DNA Sequence:

GATATCGAACTGACCCAGCCGCCTTCAGTGAGCGTTGCACCAGGTCAGACCGCGCGTATCTCGTGTAGCGGCGATAATAT
TCCTCTTAAGTATGTTTCTTGGTACCAGCAGAAACCCGGGCAGGCGCCAGTTCTTGTGATTCATGATGATAATAAGCGTC
CCTCAGGCATCCCGGAACGCTTTAGCGGATCCAACAGCGGCAACACCGCGACCCTGACCATTAGCGGCACTCAGGCGAA
GACGAAGCGGATTATTATTGCTCTCTTCTTGGATATCTCTTGATATTTTTAATGTGTTTGGCGGCGGCACGAAGTTAACCGT
CCTAGGT

VH3 Amino Acid Sequence:

QVELVESGGGLVQPGGSLRLSCAASGFTFSNYMHWVRQAPGKGLEWVSGISGWSSWTYYADSVKGRFT
ISRDNSKNTLYLQMNSLRAEDTAVYYCARFGIDAYTKVYFDIWGQGTLVTVSS

VH3 DNA Sequence:

CAGGTGGAATTGGTGGAAAGCGGCGGCCTGGTGCAACCGGGCGGCAGCCTGCGTCTGAGCTGCGCGGCCTCCGGATT
TACCTTTTCTAATTATTGGATGCATTGGGTGCGCCAAGCCCCTGGAAAGGGTCTGGAGTGGGTGAGCGGTATCTCTGGTT
GGTCTAGCTGGACCTATTATGCGGATAGCGTGAAAGGCCGTTTTACCATTTCACGTGATAATTCGAAAAACACCCTGTAT
CTGCAAATGAACAGCCTGCGTGCGGAAGATACGGCCGTGTATTATTGCGCGCGTTTTGGTATTGATGCTTATACTAAGGT
TTATTTTGATTTGGGGCCAAGGCACCCTGGTGACGGTTAGCTCA

60819

Vλ3 Amino Acid Sequence:

DIELTQPPSVSVAPGQTARISCSGDNIPLKYVSWYQQKPGQAPVLVIHDDNKRPSGIPERFSGSNSGNTATLTIS
GTQAEDEADYYCQSYDYFPKFVVFGGGTKLIVLG (Q)

Vλ3 DNA Sequence:

GATATCGAACTGACCCAGCCGCCTTCAGTGAGCGTTGCACCAGGTCAGACCGCGCGTATCTCGTGTAGCGGCGATAATAT
TCCTCTTAAGTATGTTTCTTGGTACCAGCAGAAACCCGGGCAGGCGCCAGTTCTTGTGATTCATGATGATAATAAGCGTC
CCTCAGGCATCCCGGAACGCTTTAGCGGATCCAACAGCGGCAACACCGCAACCCTGACCATTAGCGGCACTCAGGCGAA
GACGAAGCGGATTATTATTGCCAGTCTTATGATTATTTCCTAAGTTTGTTGTGTTTGGCGGCGGCACGAAGTTAACCGT
CCTAGGT

VH3 Amino Acid Sequence:

QVELVESGGGLVQPGGSLRLSCAASGFTFTSYW
NSKNTLYLQMNSLRAEDTAVYYCARNMYTHFI

VH3 DNA Sequence:

CAGGTGGAATTGGTGGAAAGCGGCGGCCTGGTG(
TACCTTTACTTCTTATTGGATGTCTTGGGTGCCGCCAJ
ATGGTAGCTTTACCTATTATGCGGATAGCGTGAAAG(
CTGCAAATGAACAGCCTGCGTGCCGAAGATACGGCC(
GGGCCAAGGCACCCCTGGTGACGGTTAGCTCA

60833

Vλ1 Amino Acid Sequence:

DIVLTQPPSVSGAPGQRVTISCSGSSSNIGSNSVSWYQQLPGTAPKLLIYDNSKRPSGVPDRFSGSKSGTSASLAI
TGLQSEDEADYYCQSRDTYGYYWVFGGGTKLTVLG (Q)

Vλ1 DNA Sequence:

GATATCGTGCTGACCCAGCCGCCTTCAGTGAGTGGCGCACCAGGTCAGCGTGTGACCATCTCGTGTAGCGGCAGCAGCAG
CAACATTGGTTCTAATTCTGTCTGTTGGTACCAGCAGTTGCCCGGGACGGCGCCGAAACTTCTGATTTATGATAATTCTA
AGCGTCCCTCAGGCGTGCCGGATCGTTTTAGCGGCAGCAAAAGCGGCACCAGCGCGAGCCTTGCGATTACGGGCCTGCAA
AGCGAAGACGAAGCGGATTATTATTGCCAGTCTCGTGATACTTATGGTTATTATTGGGTGTTTGGCGGCGGCACGAAGTT
AACCGTCCTAGGT

Fig. 12C

ANTI-IGF ANTIBODIES

This application claims the benefit of European application number EP 08171554.2 filed Dec. 12, 2008, the contents of which are incorporated herein their entirety.

The present invention relates to the therapy of hyperproliferative diseases, in particular to the therapy of cancers.

BACKGROUND OF THE INVENTION

Insulin-like growth factor-1 (IGF-1; a 70 amino-acid polypeptide) and insulin-like growth factor-2 (IGF-2; a 67 amino-acid polypeptide) are 7.5-kD soluble factors present in serum that can potently stimulate the growth of many mammalian cells (reviewed by Pollack et al., 2004). On secretion into the bloodstream the IGFs form complexes with the IGFBPs which protect them from proteolytic degradation in the serum en route to their target tissues and prevents their association with the IGF receptors. IGFs are also known to be secreted in an autocrine or paracrine manner in target tissues themselves. This is known to occur during normal fetal development where the IGFs play a key role in the growth of tissues, bone and organs. It is also seen in many cancer tissues where there is thought to be paracrine signaling between tumour cells and stromal cells or autocrine IGF production by the tumour cells themselves (reviewed by LeRoith D, 2003).

IGF-1 and IGF-2 are able to bind to the IGF-1 receptor (IGF-1R) expressed on many normal tissues, which functionally is a 460 kD heterotetramer consisting of a dimerised alpha- and beta-subunit, with similar affinities (Rubin et al., 1995). IGF-2 can also bind to the IGF-2 receptor, which is thought to prevent IGF-2 from binding and signaling through the IGF-1R. In this respect the IGF-2R has been demonstrated to be a tumour suppressor protein. The IGF-1R is structurally similar to the insulin receptor which exists in two forms, IR-A and IR-B, which differ by an alternatively spliced 12 amino acid exon deletion in the extracellular domain of IR-A. IR-B is the predominant IR isoform expressed in most normal adult tissues where it acts to mediate the effects of insulin on metabolism. IR-A on the other hand is known to be highly expressed in developing fetal tissues but not in adult normal tissues. Recent studies have also shown that IR-A, but not IR-B, is highly expressed in some cancers. The exon deletion in IR-A has no impact on insulin binding but does cause a small conformational change that allows IGF-2 to bind with much higher affinity than for IR-B (Frasca et al., 1999; Pandini et al., 2002). Thus, because of it's expression in cancer tissues and increased propensity for IGF-2 binding, IR-A may be as important as IGF1-R in mediating the mitogenic effects of IGF-2 in cancer.

Binding of the IGFs to IGF-1R triggers a complex intracellular signaling cascade which results in activation of proteins that stimulate proliferation and survival (reviewed by Pollack et al., 2004).

Unlike the EGFR and Her2neu receptors there is no known amplification of the IGF1-R or IR-A receptors in cancers indicating that receptor activation is controlled by the presence of active ligand. There is a very large body of scientific, epidemiological and clinical literature implicating a role for the IGFs in the development, progression and metastasis of many different cancer types (reviewed by Jerome et al., 2003; and Pollack et al., 2004).

For example, in colorectal cancer the expression of IGF-2 mRNA and protein is elevated in clinical colorectal tumour specimens compared with adjacent normal tissue (Freier et al., 1999; Li et al., 2004). There is also a positive correlation of elevated IGF serum levels with proliferating cell index in patients with colorectal neoplasia (Zhao et al., 2005). In addition, elevated circulating levels of IGF-2 correlate with an increased risk of developing colorectal cancers and adenomas (Renehan et al., 2000a) and b); Hassan et al., 2000). Loss of parental imprinting (LOI) of the IGF-2 gene, an epigenetic alteration that results in elevated IGF-2 expression, is a heritable molecular trait that has recently been identified in patients with colorectal and other tumour types. Loss of IGF-2 imprinting has been shown to be associated with a five-fold risk of colorectal neoplasia (Cui et al., 2003; Cruz-Correa et al., 2004) and adenomas (Woodson et al., 2004). Antibodies targeting the alpha-subunit of the IGF-1R which block IGF binding and internalize the receptor have been shown to delay the growth of the xenografted colon cancer-derived cell lines such as COLO 205 (Burtrum et al., 2003).

Elevated levels of IGFs are associated with a poor prognosis in human pulmonary adenocarcinomas (Takanami et al., 1996) and IGFs are expressed and secreted by many SCLC- and NSCLC-derived cell lines (Quinn et al., 1996). Transgenic over-expression of IGF-2 induces spontaneous lung tumours in a murine model (Moorhead et al., 2003). In terms of hepatocellular carcinoma (HCC), human clinical specimens and animal models of HCC express higher levels of IGF mRNA and protein than corresponding normal tissues and this has been correlated with increased tumour growth (Wang et al., 2003; Ng et al., 1998). IGF-2 has also been shown to be a serological marker of HCC with elevated levels in the serum of HCC patients compared with controls (Tsai et al., 2005).

Many childhood solid tumours such as Ewing's sarcoma and rhabdomyosarcoma appear to be particularly dependent on the IGF signaling pathway for their growth (Scotlandi et al., 1996). LOI of the IGF-2 gene has been implicated as a primary genetic event in the development for embryonal rhabdomyosarcoma (Fukuzawa et al., 1999). Autocrine IGF signaling is also thought to strongly influence the growth of Ewing's sarcoma in cases where the type-1 EWS-FLI1 chimeric transcription factor is expressed through a chromosomal translocation resulting in elevated expression of target genes including the IGF ligands and IGF-1R, and reduced expression of IGFBP-3. Antibodies and small molecule compounds targeting the IGF-1R have been shown to reduce the growth of xenografted pediatric solid tumour derived cell lines (Kolb et al., 2008; Manara et al., 2007).

Using IGF ligand-specific antibodies it has been demonstrated that the growth of human prostate cancer cells in adult human bone implanted into SCID mice can be inhibited (Goya et al., 2004). In addition, it was demonstrated that the same IGF ligand antibodies could block the paracrine supply of IGF and suppress the liver metastasis of human colorectal cancer cells in a murine xenograft system (Miyamoto et al., 2005).

There is also considerable evidence suggesting that the IGF signaling system reduces the sensitivity of cancers to chemotherapeutic agents and radiation. One of the earliest findings in this respect was the demonstration that IGF-1R knock-out mouse embryos are refractory to transformation by viruses, oncogenes and over-expressed growth factor receptors (Sell et al., 1993; Sell et al., 1994) and that over-expression of IGF-1R protects cells from UV irradiation and gamma radiation-induced apoptosis (Kulik et al., 1997). Furthermore, using liver tumour cell lines that secrete large amounts of IGF-2, it was found that neutralization of IGF-2 significantly increased response to chemotherapeutic agents such as cisplatin and etoposide in vitro, especially at lower, cytostatic doses, suggesting that IGF-2 can reduce the susceptibility to chemotherapeutic agents (Lund et al., 2004). Consistent with these findings it has been demonstrated that antibodies targeting the IGF-1R increase the susceptibility of tumour xenografts to growth inhibition by chemotherapeutic drugs and radiation (Goetsch et al., 2005).

A number of antibodies that show cross-reactive binding to human IGF-1 and human IGF-2 have been reported. Antibody sm1.2 was raised against human IGF-1 and shows 40% cross-reactivity to human IGF-2 and was shown to inhibit the proliferation of a mouse fibroblast cell line BALB/c3T3 which was stimulated with 20 ng/ml human IGF-1 (Russell et al., 1984). In a study designed to functionally epitope map IGF-1 by raising monoclonal antibodies to whole IGF-1 protein and portions of the protein a number of antibodies where identified that cross reacted with IGF-2 (Manes et al., 1997). The percent cross-reactivity with IGF-2 ranged from 0 to 800% and several antibodies were identified which were equally IGF-1 and IGF-2 reactive. KM1486 is a rat monoclonal antibody that cross-reacts with human IGF-1 and IGF-2 and it was demonstrated that KM1486 can inhibit growth of human prostate cancer cells in human adult bone implanted into nonobese diabetic/severe combined immunodeficient mice (Goya et al., 2004). In addition, it was demonstrated that KM1486 suppresses the liver metastasis of human colorectal cancers (Miyamoto et al., 2005). KM1486 has also been described in WO 03/093317, JP 2003-310275, WO 2005/018671, WO 2005/028515, and WO 2005/027970.

For the treatment of human disease an antibody with a fully human sequence is highly desirable in order to minimize the risk of generating a human anti-antibody reaction and neutralizing antibodies that will rapidly eliminate the administered antibody from the body and thereby reduce the therapeutic effect. As such, and given the roles of IGF-1 and IGF-2 dependent signaling in the development and progression of cancers, it has become desirable to obtain fully human antibodies. WO 2007/070432 describes fully human antibodies that co-neutralise the mitogenic effects of both ligands.

It was an object of the invention to provide alternative human anti-IGF antibodies with high affinities.

It was a further object of the invention to provide human anti-IGF antibodies with high affinity to IGF-1.

It was a further object of the invention to provide human anti-IGF antibodies with high affinity to IGF-1 and to IGF-2.

It was a further object of the invention to provide human anti-IGF antibodies with adequate relative affinities to IGF-1 and to IGF-2.

It was a further object of the invention to provide human anti-IGF antibodies with a higher affinity to IGF-1 than to IGF-2.

It was a further object of the invention to provide human anti-IGF antibodies with high IGF-1 neutralisation potency.

It was a further object of the invention to provide human anti-IGF antibodies with high IGF-1 and IGF-2 neutralisation potency.

It was a further object of the invention to provide human anti-IGF antibodies with high solubility and stability.

It was a further object of the invention to obtain antibodies that do not affect binding of insulin to its receptor.

The clinical development of therapeutic agents is supported by pharmacodynamic biomarkers of drug activity. Clinical studies with antibodies targeting the IGF-1R have demonstrated that an increase in total serum IGF-1 levels may be a useful pharmacodynamic marker for these agents (Pollack et al., 2007). The reason for the increase in total serum IGF-1 levels is likely due to a feedback mechanism involving pituitary growth hormone (GH) secretion which releases both IGF-1 and IGFBPs from the liver. Indeed, in humans it has been demonstrated that free or bioactive IGF-1, which represents only around 1% of total IGF-1 levels, determines the feedback response (Chen et al., 2005).

It was therefore a further object of the invention to provide, for the treatment of diseases in whose development and/or progression the IGFs are causally involved, a therapy that is accompanied by a biomarker that allows the pharmacological monitoring of the effectiveness of the therapy.

In the experiments of the present invention, it could be demonstrated that total serum IGF-1 levels are elevated upon application of the anti-IGF antibodies of the invention. Thus, total IGF-1 levels are a useful pharmacodynamic marker for the effectiveness of the therapy with an anti-IGF antibody. It is therefore highly advantageous that the antibodies of the invention are cross-reactive with IGFs from a suitable animal species, e.g. mouse or rat, such that a pharmacodynamic effect can already be tested pre-clinically.

"Total IGF-1 levels" refers to the combined amount of IGF-1 in plasma or serum comprising the amount of IGF-1 bound to serum binding proteins plus the free (unbound) IGF-1.

Therefore, in a further aspect, the present invention relates to a method for determining the effectiveness of a treatment of a cancer patient with an antibody molecule that binds to IGF-1 and IGF-2. In such method, in a first step, the level of total IGF-1 is measured in a biological sample of the patient, e.g. serum or plasma. Next, the antibody molecule is administered and then, after a period of time sufficient to allow the therapeutic antibody to exert its effect, the level of total IGF-1 is again determined. The amount of increase in the level of total IGF-1 compared to the level of total IGF-1 measured in the first step, indicates to which extent the patient responds to said anti-IGF antibody molecule. This method is preferably used for monitoring therapies in which the antibodies of the invention are administered.

BRIEF DESCRIPTION OF THE FIGURES

FIG. 12 shows the amino acid and DNA sequences of the variable chains of antibodies 60814 (A, SEQ ID NOs: 7 and 8, and SEQ ID NOs: 9 and 10), 60819 (B, SEQ ID NOs: 17 and 18, and SEQ ID NOs: 19 and 20), and 60833 (C, SEQ ID NOs: 27 and 28, and SEQ ID NOs: 29 and 30); CDRs are in bold letters.

BRIEF DESCRIPTION OF INVENTION

Figure 1A:
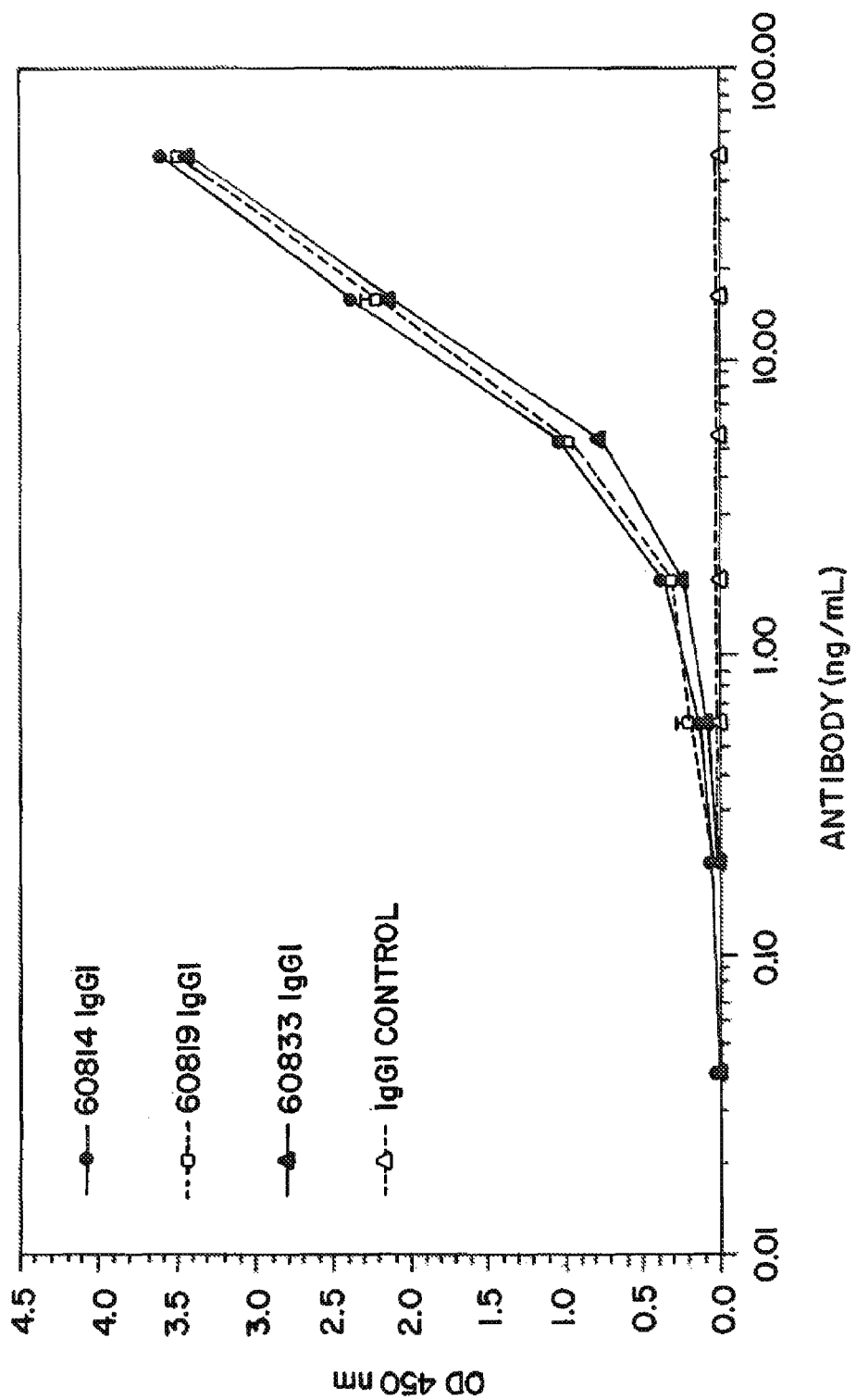
FIGS. 1A-1G show an ELISA binding titration of IgG1 antibodies designated 60814, 60819 and 60833 to human IGF-1 (FIG. 1A), mousee IGF-1 (FIG. 1B), rat IGF-1 (FIG. 1C), human IGF-2 (FIG. 1D), mouse IGF-2 (FIG. 1E), rat IGF-2 (FIG. 1F), and human insulin (FIG. 1G).
Figure 1B:
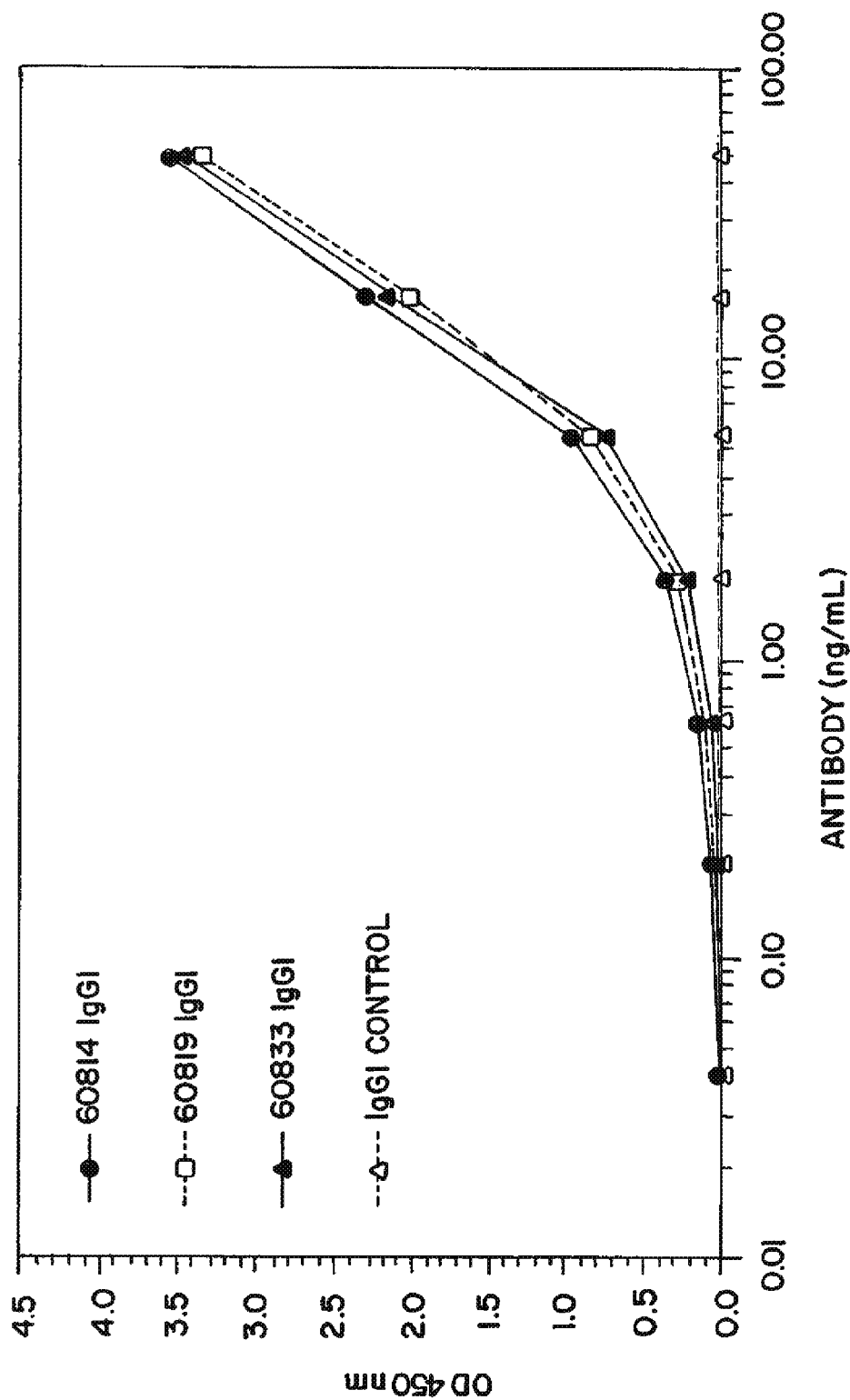
Figure 1C:
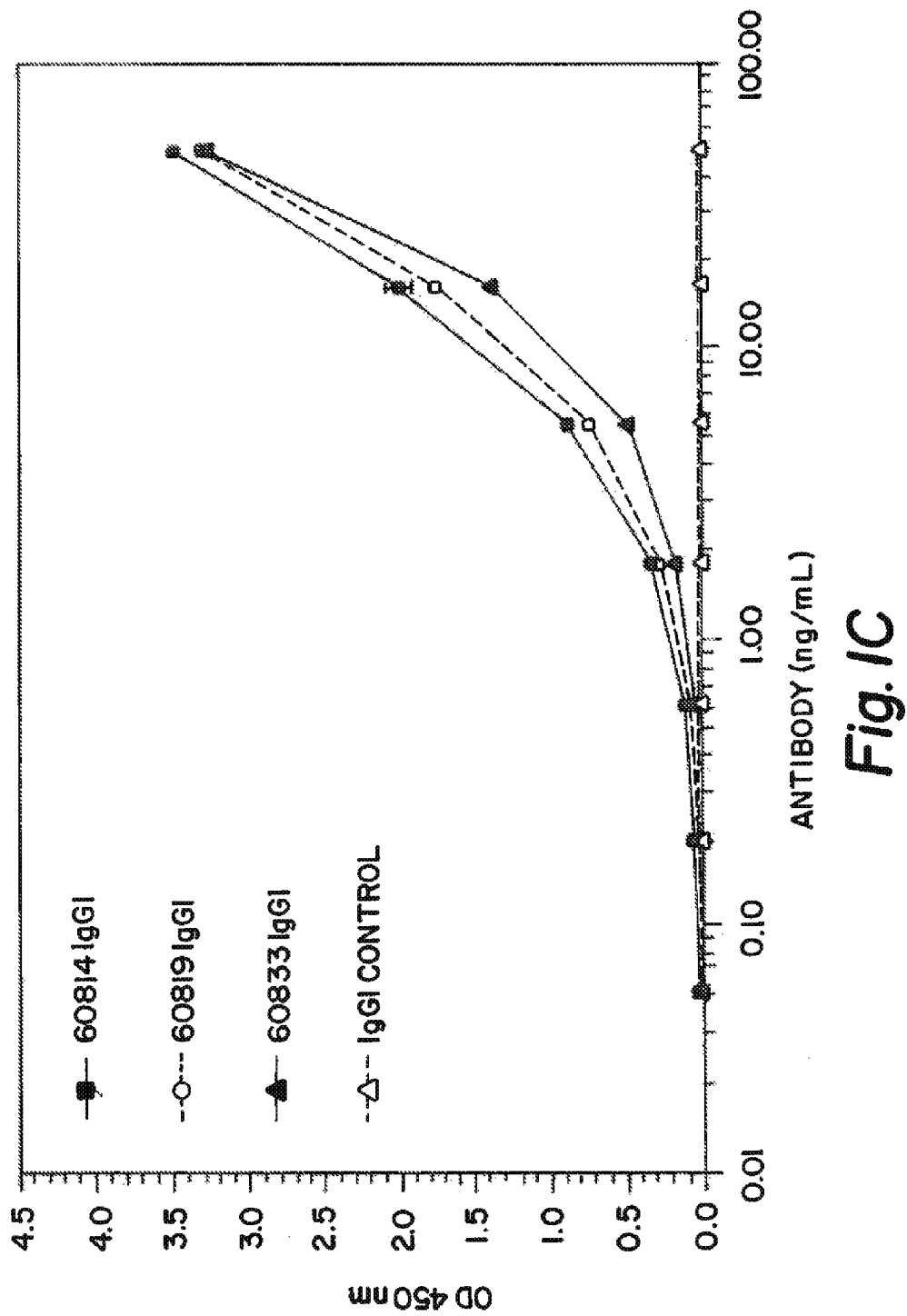
Figure 1D:
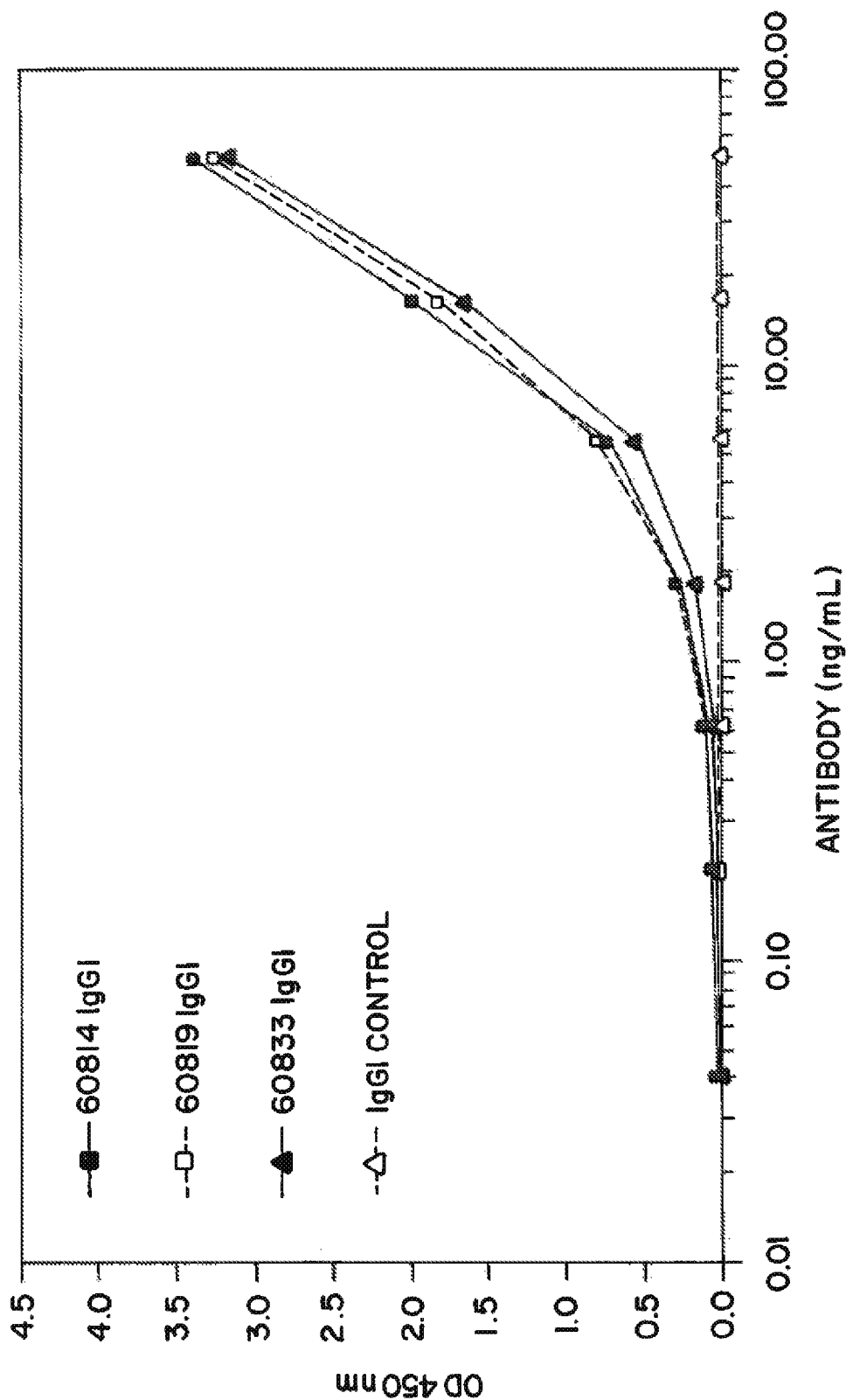
Figure 1E:
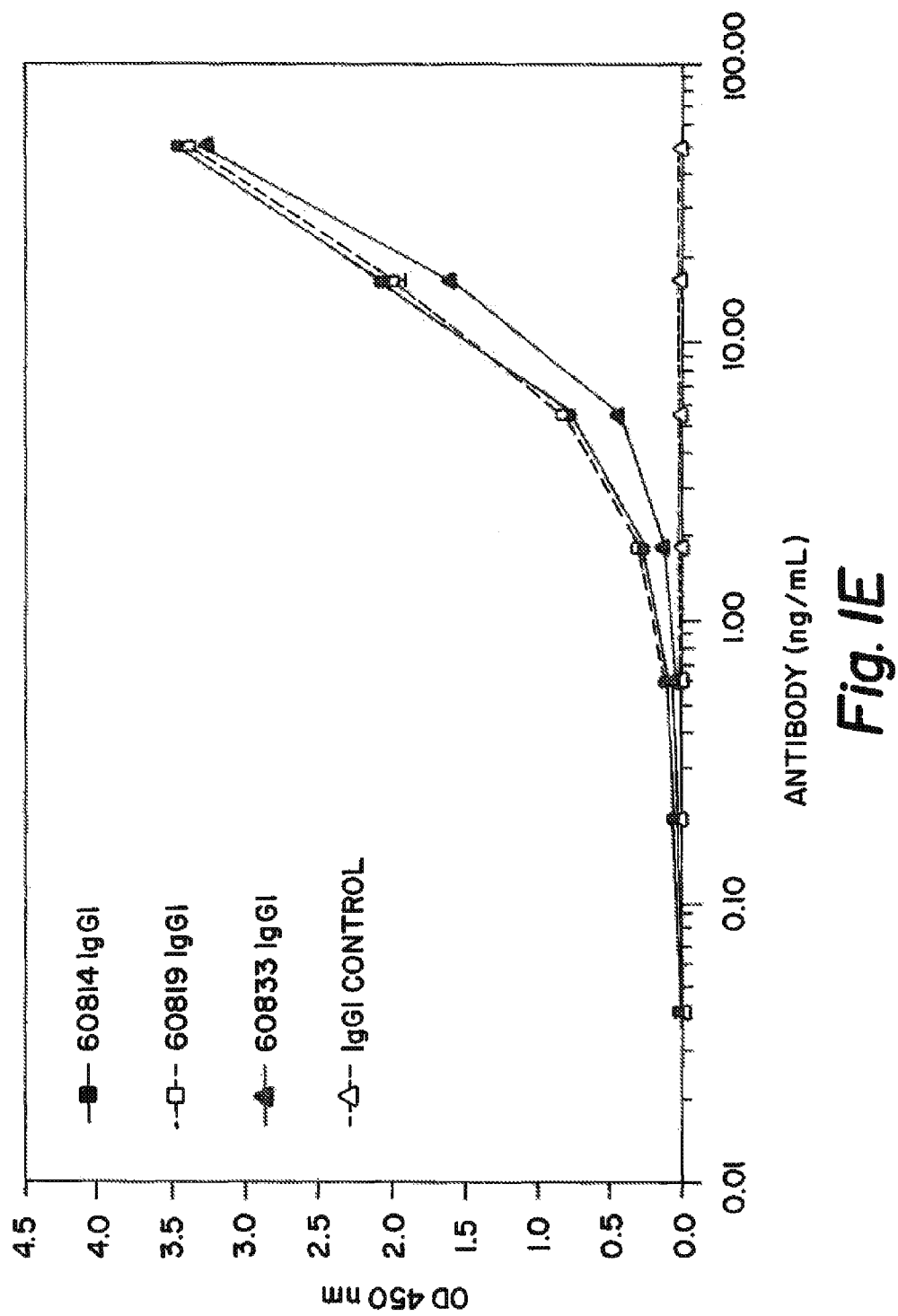
Figure 1F:
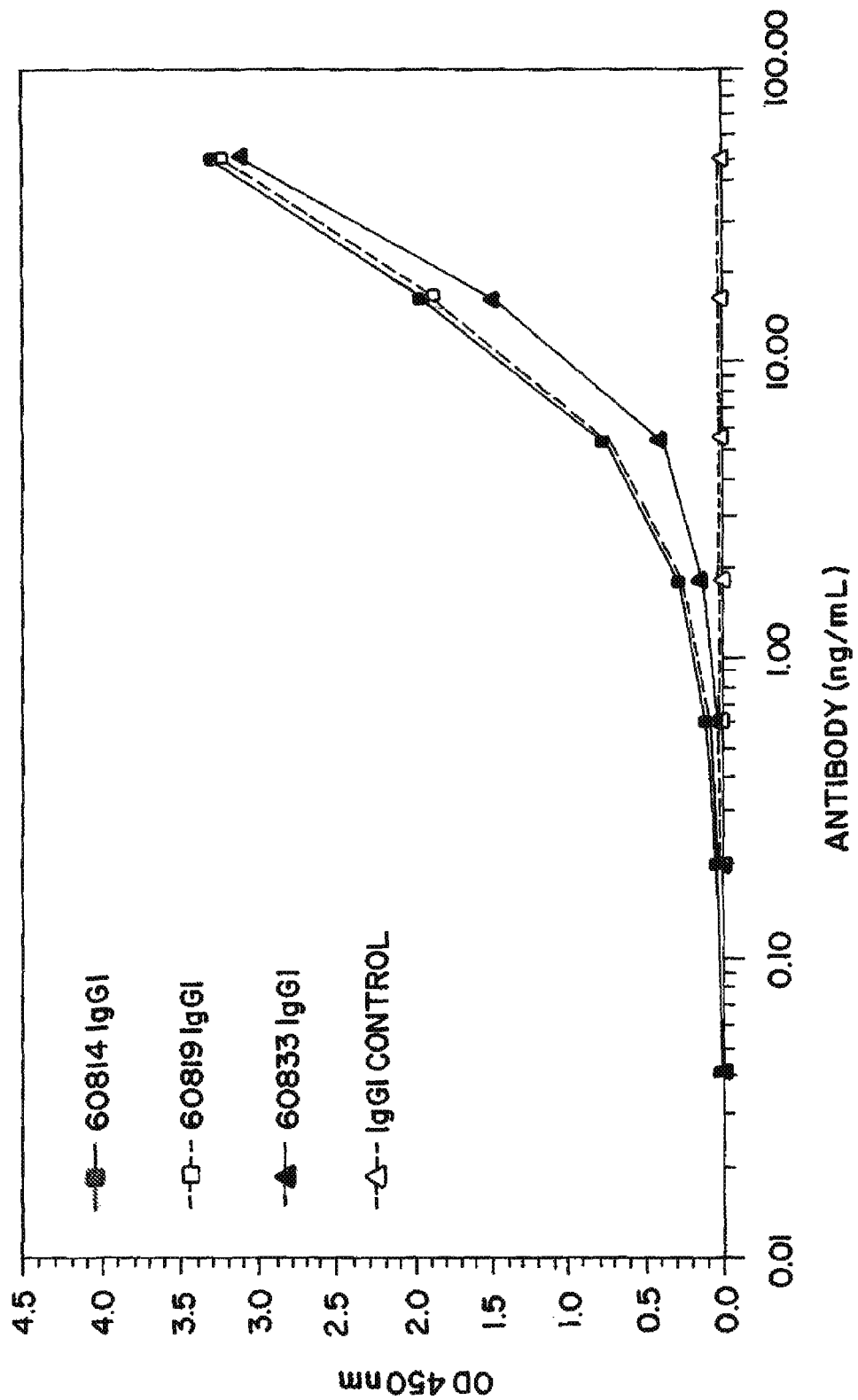
Figure 1G:
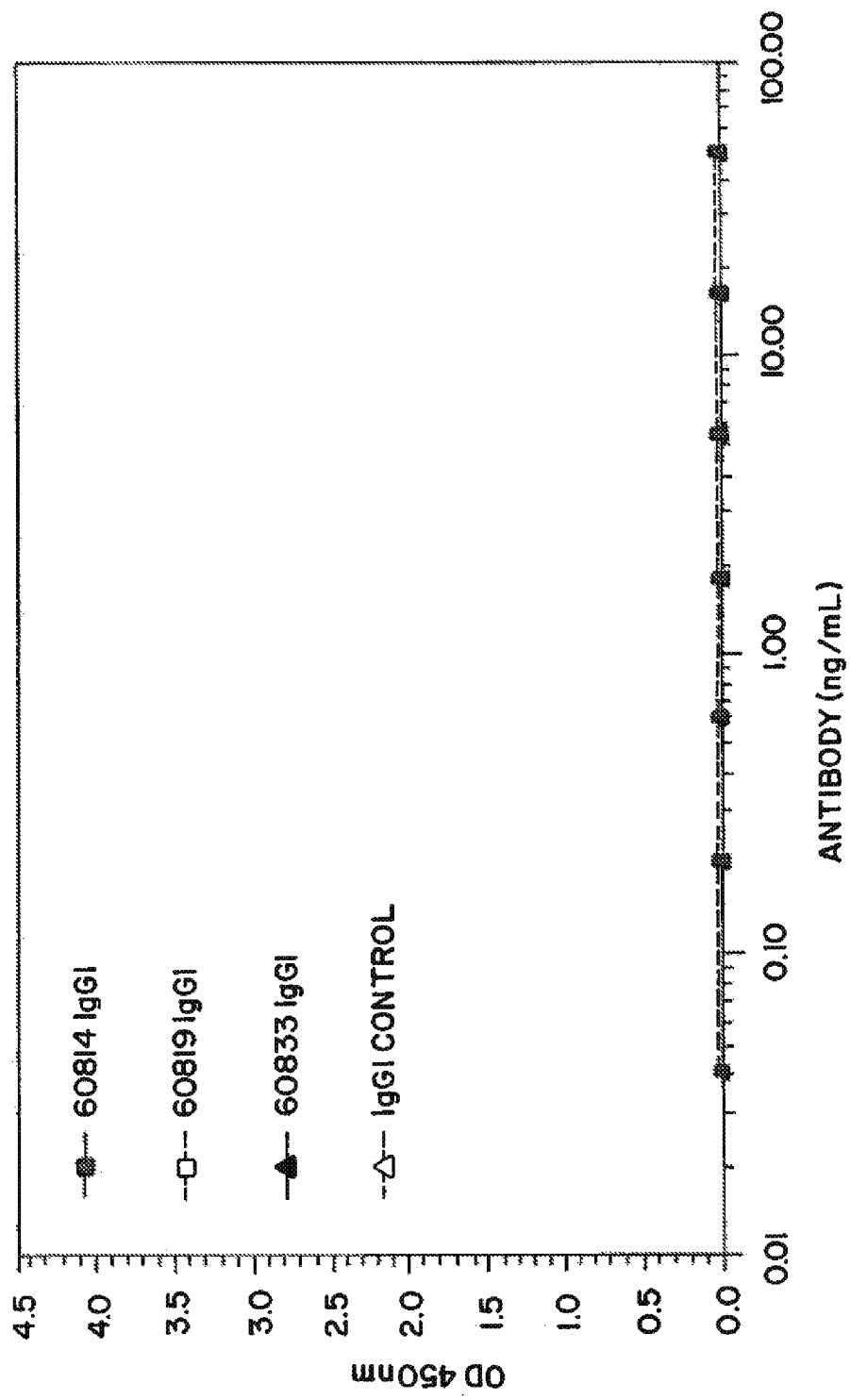

In one aspect, the present invention relates to an isolated human antibody molecule, which
a) binds to human IGF-1 and IGF-2 such that
  i) binding of IGF-1 and IGF-2 to the IGF-1 receptor is prevented and
  ii) IGF-1 receptor-mediated signaling is inhibited,
b) binds to mouse and rat IGF-1 and IGF-2,
c) does not bind to human insulin;
wherein said antibody molecule is selected from the group comprising
  i) an antibody molecule that has heavy chain CDRs comprising the amino acid sequences of SEQ ID NO:1 (CDR1), SEQ ID NO:2 (CDR2) and SEQ ID NO:3 (CDR3) and that has light chain CDRs comprising the amino acid sequences of SEQ ID NO:4 (CDR1), SEQ ID NO:5 (CDR2) and SEQ ID NO:6 (CDR3);
  ii) an antibody molecule that has heavy chain CDRs comprising the amino acid sequences of SEQ ID NO:11 (CDR1), SEQ ID NO:12 (CDR2) and SEQ ID NO:13 (CDR3) and that has light chain CDRs comprising the amino acid sequences of SEQ ID NO:14 (CDR1), SEQ ID NO:15 (CDR2) and SEQ ID NO:16 (CDR3);
  iii) an antibody molecule that has heavy chain CDRs comprising the amino acid sequences of SEQ ID NO:21 (CDR1), SEQ ID NO:22 (CDR2) and SEQ ID NO:23 (CDR3) and that has light chain CDRs comprising the amino acid sequences of SEQ ID NO:24 (CDR1), SEQ ID NO:25 (CDR2) and SEQ ID NO:26 (CDR3).

In another aspect, the present invention relates to an anti-IGF antibody molecule, wherein said antibody molecule has heavy chain CDRs comprising the amino acid sequences of SEQ ID NO:1 (CDR1), SEQ ID NO:2 (CDR2) and SEQ ID NO:3 (CDR3) and light chain CDRs comprising the amino acid sequences of SEQ ID NO:4 (CDR1), SEQ ID NO:5 (CDR2) and SEQ ID NO:6 (CDR3).

In another aspect, the present invention relates to an anti-IGF antibody molecule, wherein said antibody molecule has heavy chain CDRs comprising the amino acid sequences of SEQ ID NO:11 (CDR1), SEQ ID NO:12 (CDR2) and SEQ ID NO:13 (CDR3) and light chain CDRs comprising the amino acid sequences of SEQ ID NO:14 (CDR1), SEQ ID NO:15 (CDR2) and SEQ ID NO:16 (CDR3).

In another aspect, the present invention relates to an anti-IGF antibody molecule, wherein said antibody molecule has heavy chain CDRs comprising the amino acid sequences of SEQ ID NO:21 (CDR1), SEQ ID NO:22 (CDR2) and SEQ ID NO:23 (CDR3) and has light chain CDRs comprising the amino acid sequences of SEQ ID NO:24 (CDR1), SEQ ID NO:25 (CDR2) and SEQ ID NO:26 (CDR3).

In another aspect, the present invention relates to anti-IGF antibody molecules having heavy and light chains or CDRs having amino acid sequences as depicted in FIGS. 12A-C.

In another aspect, the present invention relates to an anti-IGF antibody molecule, wherein said antibody molecule binds to a nonlinear epitope within IGF-1 comprising the amino acid sequences LCGAELVDALQFVCGDR (SEQ ID NO:41) and CCFRSCDLRRLEM (SEQ ID NO:42) of human IGF-1 (SEQ ID NO:43). In a preferred embodiment, said antibody molecule makes contact with at least 8 amino acids within the amino acid sequence LCGAELVDALQFVCGDR (SEQ ID NO:41), and at least 10 amino acids within amino acid sequence CCFRSCDLRRLEM (SEQ ID NO:42) of human IGF-1 (SEQ ID NO:43). In a further preferred embodiment, such anti-IGF antibody molecule makes contact with Leu (5), Cys (6), Glu (9), Leu (10), Asp (12), Ala (13), Phe (16), Val (17), Arg (21), Cys (47), Cys (48), Phe (49), Ser (51), Cys (52), Asp (53), Leu (54), Arg (55), Leu (57), and Glu (58) of human IGF-1 (SEQ ID NO:43), as determined by X-ray crystallography. A respective method is disclosed in Example 9 herein. Preferably, said antibody molecule has heavy chain CDRs comprising the amino acid sequences of SEQ ID NO:21 (CDR1), SEQ ID NO:22 (CDR2) and SEQ ID NO:23 (CDR3) and has light chain CDRs comprising the amino acid sequences of SEQ ID NO:24 (CDR1), SEQ ID NO:25 (CDR2) and SEQ ID NO:26 (CDR3).

Binding of the antibody is defined as the interaction that occurs via the non-covalent bonds that hold the antigen (or a protein or a fragment thereof that is structurally similar) to the antibody combining site, i.e. the region of the immunoglobulin that combines with the determinant of an appropriate antigen (or a structurally similar protein).

Affinity (i.e. the interaction between a single antigen-binding site on an antibody and a single epitope) is expressed by the association constant $K_A = k_{ass}/k_{diss}$ or the dissociation constant $K_D = k_{diss}/k_{ass}$.

In one aspect according to a), the antibody binds to each IGF protein with an affinity, as determined by surface plasmon resonance analysis, with a $K_D$ value ranging from 0.02 nM to 20 nm, e.g. 0.2 nM to 2 nM, for example, with an affinity of 0.05, 0.1, 0.2, 0.3, 0.4, 0.5, 0.6, 0.7, 0.8, 0.9, or 1.0 nM. Based on this property, neutralization of IGF functional signaling is achieved.

In one aspect according to c), the antibody does not bind to human insulin at concentrations that are at least 100-fold higher than the minimum concentration required for binding to human IGF-1 or IGF-2.

In another aspect, the property of the anti-IGF antibody molecule defined in c) is characterized by the fact that the affinity of the anti-IGF antibody molecule to IGF-1 and IGF-2, respectively, is at least 100-fold, and even more than 1000-fold, as compared to its affinity to insulin. Even though at very high doses, e.g. more than 100 mg/kg, weak binding may not be completely excluded, the anti-IGF antibody molecule does not bind to insulin at therapeutic doses.

In one embodiment, the antibody molecules of the invention do not affect the mitogenic properties of human insulin that are mediated by its binding to the insulin receptor. (In general, a mitogenic property is defined as the ability of a compound to encourage a cell to commence cell division, triggering mitosis, e.g. in the case of insulin, its ability to promote cell growth).

In another embodiment, in addition to its ability to inhibit IGF signaling mediated via the IGF-1 receptor, an antibody of the invention also has the ability to inhibit IGF-2 signaling mediated via the insulin receptor IR-A.

The antibodies of the invention have a surprisingly high neutralisation potency towards IGF-1 and IGF-2. Furthermore, they have an unexpected higher potency and binding affinity towards IGF-1 than towards IGF-2. They have high solubility and stability, they are free of undesirable glycosylation or hydrolysis motifs in the variable domain, and have a long half-life in the circulation.

DETAILED DESCRIPTION OF THE INVENTION

In the following, an antibody molecule of the invention, which binds to human IGF-1 and IGF-2, is termed "anti-IGF antibody molecule".

The term "anti-IGF antibody molecule" encompasses human anti-IGF antibodies, anti-IGF antibody fragments, anti-IGF antibody-like molecules and conjugates with any of the above mentioned antibody molecules. Antibodies include, in the meaning of the present invention, but are not limited to, monoclonal, chimerized monoclonal, and bi- or multispecific antibodies. The term "antibody" shall encompass complete immunoglobulins as they are produced by lymphocytes and for example present in blood sera, monoclonal antibodies secreted by hybridoma cell lines, polypeptides produced by recombinant expression in host cells, which have the binding specificity of immunoglobulins or monoclonal antibodies, and molecules which have been derived from such immunoglobulins, monoclonal antibodies, or polypeptides by further processing while retaining their binding specificity.

In particular, the term "antibody molecule" includes fully human complete immunoglobulins comprising two heavy chains and two light chains, preferably.

In a further aspect, the antibody molecule is an anti-IGF antibody-fragment that has an antigen binding region. To obtain antibody fragments, e.g. Fab fragments, digestion can be accomplished by means of routine techniques, e.g. using papain or pepsin. Examples of papain digestion are described in WO 94/29348 and U.S. Pat. No. 4,342,566. Papain digestion of antibodies typically produces two identical antigen binding fragments, so-called Fab fragments, each with a single antigen binding site, and a residual Fc fragment. Pepsin treatment yields an F(ab')$_2$ fragment that has two antigen combining sites and is still capable of cross-linking the antigen. Antibody fragments can also be generated by molecular biology methods producing the respective coding DNA fragments.

Fab fragments also contain the constant domains of the light chain and the first constant domain (CH$_1$) of the heavy chain. Fab' fragments differ from Fab fragments in that they contain additional residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them.

Antigen-binding antibody fragments or antibody-like molecules, including single-chain antibodies and linear antibodies as described in Zapata et al., 1995, may comprise, on a single polypeptide, the variable region(s) alone or in combination with the entirety or a portion of the following: constant domain of the light chain, CH1, hinge region, CH2, and CH3 domains, e.g. a so-called "SMIP" ("Small Modular Immunopharmaceutical"), which is an antibody like molecule employing a single polypeptide chain as its binding domain Fv, which is linked to single-chain hinge and effector domains devoid of the constant domain CH1 (WO 02/056910). SMIPs can be prepared as monomers or dimers, but they do not assume the dimer-of-dimers structure of traditional antibodies. Also included in the invention are antigen-binding fragments comprising any combination of variable region(s) with a constant domain region of a light chain, VH1, CH1, hinge region, CH2, and CH3 domains.

The antibody fragments or antibody-like molecules may contain all or only a portion of the constant region as long as they exhibit specific binding to the relevant portion of the IGF-1/IGF-2 antigen. The choice of the type and length of the constant region depends, if no effector functions like complement fixation or antibody dependent cellular toxicity are desired, mainly on the desired pharmacological properties of the antibody protein. The antibody molecule will typically be a tetramer consisting of two light chain/heavy chain pairs, but may also be dimeric, i.e. consisting of a light chain/heavy chain pair, e.g. a Fab or Fv fragment, or it may be a monomeric single chain antibody (scFv).

The anti-IGF antibody-like molecules may also be single domain antibodies (e.g. the so-called "nanobodies"), which harbour an antigen-binding site in a single Ig-like domain (described e.g. in WO 03/050531, and by Revets et al., 2005). Other examples for antibody-like molecules are immunoglobulin super family antibodies (IgSF; Srinivasan and Roeske, 2005), or CDR-containing or CDR-grafted molecules or "Domain Antibodies" (dAbs). dABs are functional binding units of antibodies, corresponding to the variable regions of either the heavy (VH) or light (VL) chains of human antibodies. Domain Antibodies have a molecular weight of approximately 13 kDa, or less than one-tenth the size of a full antibody. A series of large and highly functional libraries of fully human VH and VL dAbs has been developed. dABs are also available for "dual targeting", i.e. dAbs that bind, in addition to IGF-1/IGF-2, to a further target in one molecule. dAb libraries, selection and screening methods, dAb formats for dual targeting and for conferring extended serum half life are described in e.g. U.S. Pat. No. 6,696,245, WO 04/058821, WO 04/003019, and WO 03/002609.

In general, antibody fragments and antibody-like molecules are well expressed in bacterial, yeast, and mammalian cell systems.

In a preferred embodiment, an antibody molecule of the invention, as defined above in i), has a variable heavy chain comprising the amino acid sequence of SEQ ID NO:8 and a variable light chain comprising the amino acid sequence of SEQ ID NO:10 (this sequence may contain, at its C-terminus, an additional Gln. This amino acid position may either be considered the C-terminal end of the variable region, according to the Kabat numbering, or alternatively, and in line with the sequences in the sequence listing, it may represent the first amino acid of the constant light chain, see SEQ ID NO:34).

Preferably, an antibody with the variable heavy chain comprising the amino acid sequence of SEQ ID NO:8 and a variable light chain comprising the amino acid sequence of SEQ ID NO:10 has an IgG1 constant heavy chain region. Preferably, such antibody has an Igλ constant light chain region. Preferably, such antibody is the antibody designated 60814, which has a heavy chain constant region which comprises the amino acid sequence of SEQ ID NO:32 and a light chain constant region which comprises the amino acid sequence of SEQ ID NO:34. The complete amino acid sequences of the antibody designated 60814 are depicted in SEQ ID NO:35 (heavy chain) and SEQ ID NO:36 (light chain).

In another preferred embodiment, an antibody molecule of the invention, as defined above in ii), has a variable heavy chain comprising the amino acid sequence of SEQ ID NO:18 and a variable light chain comprising the amino acid sequence of SEQ ID NO:20 (this sequence may contain, at its C-terminus, an additional Gln. This amino acid position may either be considered the C-terminal end of the variable region, according to the Kabat numbering, or alternatively, and in line with the sequences in the sequence listing, it may represent the first amino acid of the constant light chain, see SEQ ID NO:34).

Preferably, an antibody with the variable heavy chain comprising the amino acid sequence of SEQ ID NO:18 and a variable light chain comprising the amino acid sequence of SEQ ID NO:20 has an IgG1 constant heavy chain region. Preferably, such antibody has an Igλ constant light chain region. Preferably, such antibody is the antibody designated 60819, which has a heavy chain constant region which comprises the amino acid sequence of SEQ ID NO:32 and a light chain constant region which comprises the amino acid sequence of SEQ ID NO:34. The complete amino acid sequences of the antibody designated 60819 are depicted in SEQ ID NO:37 (heavy chain) and SEQ ID NO:38 (light chain).

In another preferred embodiment, an antibody of the invention, as defined above in iii), has a variable heavy chain comprising the amino acid sequence of SEQ ID NO:28 and a variable light chain comprising the amino acid sequence of SEQ ID NO:30 (this sequence may contain, at its C-terminus, an additional Gln. This amino acid position may either be considered the C-terminal end of the variable region, according to the Kabat numbering, or alternatively, and in line with the sequences in the sequence listing, it may represent the first amino acid of the constant light chain, see SEQ ID NO:34).

Preferably, an antibody with the variable heavy chain comprising the amino acid sequence of SEQ ID NO:28 and a variable light chain comprising the amino acid sequence of SEQ ID NO:30 has an IgG1 constant heavy chain region. Preferably, such antibody has an Igλ constant light chain region. Preferably, such antibody is the antibody designated 60833, which has a heavy chain constant region which comprises the amino acid sequence of SEQ ID NO:32 and a light chain constant region which comprises the amino acid sequence of SEQ ID NO:34. The complete amino acid sequences of the antibody designated 60833 are depicted in SEQ ID NO:39 (heavy chain) and SEQ ID NO:40 (light chain).

The cross-reactivity of the antibodies of the invention with mouse and rat IGF-1 allows to examine their endocrine effects, e.g. the effect on the growth hormone pathway, in these species. Cross-reactivity with the rat IGFs is particularly advantageous because the rat is an excellent animal model that is preferably used in drug development to study toxicological effects.

The observed pharmacodynamic effect of the antibodies on total IGF-1 levels, likely due to removal of the free IGF-1, which results in feedback regulation through the growth hormone pathway resulting in increased secretion of IGF-1 by the liver, is a useful pharmacodynamic marker. The availability of such marker in animal species, which allows determination of a dose/effect relationship early in drug development, facilitates the preparation of Phase I clinical studies where, in addition to PK analysis, the pharmacodynamic response on total IGF-1 levels in patients are monitored.

The anti-IGF antibody molecule of the invention may also be a variant of an antibody as defined by the amino acid sequences shown in the sequence listing. Thus, the invention also embodies antibodies that are variants of these polypeptides, which have the features a) to c) defined above. Using routinely available technologies, the person skilled in the art will be able to prepare, test and utilize functional variants of the antibodies 60814, 60819 and 60833. Examples are variant antibodies with at least one position in a CDR and/or framework altered, variant antibodies with single amino acid substitutions in the framework region where there is a deviation from the germline sequence, antibodies with conservative amino substitutions, antibodies that are encoded by DNA molecules that hybridize, under stringent conditions, with the DNA molecules presented in the sequence listing encoding antibody variable chains of 60814, 60819 or 60833, functionally equivalent codon-optimized variants of 60814, 60819 and 60833.

A variant may also be obtained by using an antibody of the invention as starting point for optimization and diversifying one or more amino acid residues, preferably amino acid residues in one or more CDRs, and by screening the resulting collection of antibody variants for variants with improved properties. Particularly preferred is diversification of one or more amino acid residues in CDR3 of the variable light chain, CDR3 of the variable heavy chain, CDR1 of the variable light and/or CDR2 of the variable heavy chain. Diversification can be done by methods known in the art, e.g. the so-called TRIM technology referred to in WO 2007/042309.

Given the properties of individual amino acids, rational substitutions can be performed to obtain antibody variants that conserve the overall molecular structure of antibody 60814, 60819 or 60833. Amino acid substitutions, i.e., "conservative substitutions", may be made, for instance, on the basis of similarity in polarity, charge, solubility, hydrophobicity, hydrophilicity, and/or the amphipathic nature of the respective amino acid. The skilled person is familiar with commonly practiced amino acid substitutions, as described e.g. in WO 2007/042309, and methods for obtaining thus modified antibodies. Given the genetic code and recombinant and synthetic DNA techniques, DNA molecules encoding variant antibodies with one or more conservative amino acid exchanges can be routinely designed and the respective antibodies readily obtained.

Preferred antibody variants have a sequence identity in the variable regions of at least 60%, more preferably, at least 70% or 80%, still more preferably at least 90% and most preferably at least 95%. Preferred antibodies also have a sequence similarity in the variable regions of at least 80%, more preferably 90% and most preferably 95%.

("Sequence identity" between two polypeptide sequences indicates the percentage of amino acids that are identical between the sequences. "Sequence similarity" indicates the percentage of amino acids that either are identical or that represent conservative amino acid substitutions.)

In a further embodiment, the anti-IGF antibody molecule of the invention is an "affinity matured" antibody.

An "affinity matured" anti-IGF antibody is an anti-IGF antibody derived from a parent anti-IGF antibody, e.g. 60814, 60819 or 60833, that has one or more alterations in one or more CDRs or in which one or more complete CDRs have been replaced, which results in an improvement in the affinity for the antigens, compared to the respective parent antibody. One of the procedures for generating such antibody mutants involves phage display (Hawkins et al., 1992; and Lowman et al., 1991). Briefly, several hypervariable region sites (e.g. 6-7 sites) are mutated to generate all possible amino substitutions at each site. The antibody mutants thus generated are displayed in a monovalent fashion from filamentous phage particles as fusions to the gene III product of M13 packaged within each particle. The phage-displayed mutants are then screened for their biological activity (e.g. binding affinity) as herein disclosed.

Affinity matured antibodies may also be produced by methods as described, for example, by Marks et al., 1992, (affinity maturation by variable heavy chain (VH) and variable light chain (VL) domain shuffling), or Barbas et al., 1994; Shier et al., 1995; Yelton et al., 1995; Jackson et al., 1995; and Hawkins et al., 1992, (random mutagenesis of CDR and/or framework residues). Preferred affinity matured antibodies will have very high affinities, e.g. low picomolar, for the target antigen.

The present invention also relates to DNA molecules that encode an anti-IGF antibody molecule of the invention. These sequences include, but are not limited to, those DNA molecules encoding antibodies 60814, 60819 and 60833 as shown in the sequence listing: SEQ ID NO:7 and SEQ ID NO:9, respectively, encoding the variable heavy and light chain, respectively, of antibody 60814; SEQ ID NO:17 and SEQ ID NO:19, encoding the variable heavy and light chain, respectively, of antibody 60819; SEQ ID NO:27 and SEQ ID NO:29, encoding the variable heavy and light chain, respectively, of antibody 60833.

The sequences shown in SEQ ID NO:9, SEQ ID NO:19 and 29, encoding the variable light chains, may, at their 3' end, contain an additional codon for Gln.

Accordingly, the present invention also relates to nucleic acid molecules that hybridize to the DNA molecules set forth in the sequence listing under high stringency binding and washing conditions, as defined in WO 2007/042309, where such nucleic molecules encode an antibody or functional fragment thereof that has properties equivalent or superior to antibody 60814, 60819 or 60833. Preferred molecules (from an mRNA perspective) are those that have at least 75% or 80% (preferably at least 85%, more preferably at least 90% and most preferably at least 95%) homology or sequence identity with one of the DNA molecules described herein.

Yet another class of DNA variants that are within the scope of the invention may be defined with reference to the polypeptide they encode. These DNA molecules deviate with respect to their sequence from those depicted in the sequence listing (SEQ ID NOs:7, 17 and 27, or 9, 19, 29, respectively), but encode, due to the degeneracy of the genetic code, antibodies with the identical amino acid sequences of antibodies 60814, 60819 or 60833, respectively. By way of example, in view of expressing antibodies 60814, 60819 or 60833 in eukaryotic cells, the last nine nucleotides, respectively, that encode the last three amino acids of the variable light chains, can be designed to match codon usage in eukaryotic cells. If it is desired to express the antibodies in *E. coli*, these sequences can be changed to match *E. coli* codon usage.

Variants of DNA molecules of the invention can be constructed in several different ways, as described in WO 2007/042309.

For producing the recombinant anti-IGF antibody molecules of the invention, the DNA molecules (cDNA and/or genomic DNA) encoding full-length light chain (in the case of antibody 60814, a sequence comprising SEQ ID NO:9 and SEQ ID NO:33) and heavy chain (in the case of antibody 60814, the sequence comprising SEQ ID NO:7 and SEQ ID NO:31), or fragments thereof, are inserted into expression vectors such that the sequences are operatively linked to transcriptional and/or translational control sequences. In the case of antibody 60819, the sequences are those of SEQ ID NO:19 and SEQ ID NO:33, and SEQ ID NO:17 and SEQ ID NO:31, respectively, in the case of antibody 60833, the sequences are those of SEQ ID NO:29 and SEQ ID NO:33, and SEQ ID NO:27 and SEQ ID NO:31, respectively.

For manufacturing the antibodies of the invention, the skilled artisan may choose from a great variety of expression systems well known in the art, e.g. those reviewed by Kipriyanow and Le Gall, 2004.

In another aspect, the present invention relates to an expression vector containing a DNA molecule comprising the nucleotide sequence encoding the variable heavy chain and/or the variable light chain of an antibody molecule as described above. Preferably, such an expression vector of containing a DNA molecule comprising the nucleotide sequence of SEQ ID NO:7 and/or SEQ ID NO:9, or comprising the sequence of SEQ ID NO:17 and/or SEQ ID NO:19, or comprising the sequence of SEQ ID NO:27 and/or SEQ ID NO:29. Preferably, such an expression vector additionally comprises a DNA molecule encoding the constant heavy chain and/or the constant light chain, respectively, linked to the DNA molecule encoding the variable heavy chain and/or the variable light chain, respectively.

Expression vectors include plasmids, retroviruses, cosmids, EBV derived episomes, and the like. The expression vector and expression control sequences are selected to be compatible with the host cell. The antibody light chain gene and the antibody heavy chain gene can be inserted into separate vectors. In certain embodiments, both DNA sequences are inserted into the same expression vector. Convenient vectors are those that encode a functionally complete human CH (constant heavy) or CL (constant light) immunoglobulin sequence, with appropriate restriction sites engineered so that any VH (variable heavy) or VL (variable light) sequence can be easily inserted and expressed, as described above. In the case of the antibodies with the variable regions of 60814, 60819 and 60833, the constant chain is usually kappa or lambda for the antibody light chain, for the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the antibody chain from a host cell. The DNA encoding the antibody chain may be cloned into the vector such that the signal peptide is linked in-frame to the amino terminus of the mature antibody chain DNA. The signal peptide may be an immunoglobulin signal peptide or a heterologous peptide from a non-immunoglobulin protein. Alternatively, the DNA sequence encoding the antibody chain may already contain a signal peptide sequence.

In addition to the antibody chain DNA sequences, the recombinant expression vectors carry regulatory sequences including promoters, enhancers, termination and polyadenylation signals and other expression control elements that control the expression of the antibody chains in a host cell. Examples for promoter sequences (exemplified for expression in mammalian cells) are promoters and/or enhancers derived from CMV (such as the CMV Simian Virus 40 (SV40) promoter/enhancer), adenovirus, (e. g., the adenovirus major late promoter (AdMLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e. g. origins of replication) and selectable marker genes.

Nucleic acid molecules encoding the heavy chain or an antigen-binding portion thereof and/or the light chain or an antigen-binding portion thereof of an anti-IGF antibody, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the heavy chain and the light chain are present on two vectors which are co-transfected into the host cell, preferably a mammalian cell.

In a further aspect, the present invention relates to a host cell carrying one or more expression vectors as described before, preferably a mammalian cell.

Mammalian cell lines available as hosts for expression are well known in the art and include, inter alia, Chinese hamster ovary (CHO) cells, NSO, SP2/0 cells, HeLa cells, baby hamster kidney (BHK) cells, monkey kidney cells (COS), human carcinoma cells (e. g., Hep G2 and A-549 cells), 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used. The anti-IGF antibody molecules of the invention are produced by culturing the host cells for a period of time sufficient to allow for expression of the antibody molecule in the host cells.

Thus, in a further aspect, the present invention relates to a method for producing an antibody molecule as described, comprising transfecting a mammalian host cell with one or more vectors as described, cultivating the host cell and recovering and purifying the antibody. In another embodiment, the present invention relates to a method for producing an antibody as described above, comprising obtaining a mammalian host cell comprising one or more vectors as described, and cultivating the host cell. In another embodiment, the method further comprises recovering and purifying the antibody.

Antibody molecules are preferably recovered from the culture medium as a secreted polypeptide or it can be recovered from host cell lysates if for example expressed without a secretory signal. It is necessary to purify the antibody molecules using standard protein purification methods used for recombinant proteins and host cell proteins in a way that substantially homogenous preparations of the antibody are obtained. By way of example, state-of-the art purification methods useful for obtaining the anti-IGF antibody molecule of the invention include, as a first step, removal of cells and/or particulate cell debris from the culture medium or lysate. The antibody is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining an anti-IGF antibody molecule preparation, the purified antibody molecule may be dried, e.g. lyophilized, as described below for therapeutic applications.

In one embodiment, the anti-IGF antibody molecule of the invention may be purified by a sequence of state-of-the art purifications steps comprising affinity chromatography (recombinant Protein A), low pH viral inactivation, depth filtration, cation exchange chromatography, anion exchange chromatography, nanofiltration, and 30 kD ultra/diafiltration (Shukla et al., 2007).

In a further aspect, the present invention relates to an antibody molecule as described above for use in medicine.

In a further aspect, the present invention relates to a pharmaceutical composition containing, as the active ingredient, an anti-IGF antibody molecule, preferably a full antibody, of the invention.

To be used in therapy, the anti-IGF antibody molecule is included into pharmaceutical compositions appropriate to facilitate administration to animals or humans. Typical formulations of the anti-IGF antibody molecule can be prepared by mixing the anti-IGF antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function.

The anti-IGF antibody molecules may also be dried (freeze-dried, spray-dried, spray-freeze dried, dried by near or supercritical gases, vacuum dried, air-dried), precipitated or crystallized or entrapped in microcapsules that are prepared, for example, by coacervation techniques or by interfacial polymerization using, for example, hydroxymethylcellulose or gelatin and poly-(methylmethacylate), respectively, in colloidal drug delivery systems (for example, liposomes, albumin microspheres, microemulsions, nano-particles and nanocapsules), in macroemulsions or precipitated or immobilized onto carriers or surfaces, for example by pcmc technology (protein coated microcrystals). Such techniques are disclosed in Remington, 2005.

Naturally, the formulations to be used for in vivo administration must be sterile; sterilization may be accomplished be conventional techniques, e.g. by filtration through sterile filtration membranes.

It may be useful to increase the concentration of the anti-IGF antibody to come to a so-called high concentration liquid formulation (HCLF); various ways to generate such HCLFs have been described.

The anti-IGF antibody molecule may also be contained in a sustained-release preparation. Such preparations include solid, semi-solid or liquid matrices of hydrophobic or hydrophilic polymers, and may be in the form of shaped articles, e.g., films, sticks or microcapsules and may be applied via an application device. Examples of sustained-release matrices include polyesters, hydrogels (for example, poly(2-hydroxyethyl-methacrylate or sucrose acetate butyrate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilization (e.g. as described in WO 89/011297) from acidic solutions, controlling moisture content, using appropriate additives, and developing specific polymer matrix compositions.

Formulations that may also be used for the anti-IGF antibody molecule of the invention are described in U.S. Pat. Nos. 7,060,268 and 6,991,790.

The IGF antibody molecule can be incorporated also in other application forms, such as dispersions, suspensions or liposomes, tablets, capsules, powders, sprays, transdermal or intradermal patches or creams with or without permeation enhancing devices, wafers, nasal, buccal or pulmonary formulations, or may be produced by implanted cells or—after gene therapy—by the individual's own cells.

An anti-IGF antibody molecule may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding.

The preferred mode of application is parenteral, by infusion or injection (intraveneous, intramuscular, subcutaneous, intraperitoneal, intradermal), but other modes of application such as by inhalation, transdermal, intranasal, buccal, oral, may also be applicable.

In a preferred embodiment, the pharmaceutical composition of the invention contains the anti-IGF-antibody, e.g. antibody 60814, 60819 or 60833, in a concentration of 10 mg/ml and further comprises 25 mM Na citrate pH 6, 115 mM NaCl, 0.02% Tween® (polysorbate 20).

In another embodiment, the pharmaceutical composition of the invention is an aqueous solution which contains the anti-IGF-antibody, e.g. antibody 60814, 60819 or 60833, in a concentration of 10 mg/ml, and further comprises 25 mM histidine HCl pH 6, 38.8 g/L mannitol, 9.70 g/L sucrose, and 0.02% Tween® (polysorbate 20).

For intravenous infusion, the pharmaceutical composition of the invention may be diluted with a physiological solution, e.g. with 0.9% sodium chloride or G5 solution.

The pharmaceutical composition may be freeze-dried and reconstituted with water for injection (WFI) before use.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g. 0.1-15 mg/kg) of antibody is an initial candidate dosage for administration to the patient, whether, for example, by one or more separate administrations, or by continuous infusion, e.g. infusion over 1 hour. A typical treatment schedule usually involves administration of the antibody once every week to once every three weeks with doses ranging from about 0.1 µg/kg to ca. 20 mg/kg or more, depending on the factors mentioned above. For example, a weekly dose could be 5, 10, or 15 mg/kg. Progress of this therapy is easily monitored by conventional techniques and assays.

The "therapeutically effective amount" of the antibody to be administered is the minimum amount necessary to prevent, ameliorate, or treat a disease or disorder.

The anti-IGF antibody molecule of the invention and pharmaceutical compositions containing it are useful for the treatment of hyperproliferative disorders.

In certain embodiments, the hyperproliferative disorder is cancer.

Cancers are classified in two ways: by the type of tissue in which the cancer originates (histological type) and by primary site, or the location in the body, where the cancer first developed. The most common sites in which cancer develops include the skin, lung, breast, prostate, colon and rectum, cervix and uterus.

The anti-IGF antibody molecules of the invention are useful in the treatment of a variety of cancers, including but not limited to the following:

AIDS-related cancer such as Kaposi's sarcoma;

bone related cancer such as Ewing's family of tumours and osteosarcoma;

brain related cancer such as adult brain tumour, childhood brain stem glioma, childhood cerebellar astrocytoma, childhood cerebral astrocytoma/malignant glioma, childhood ependymoma, childhood medulloblastoma, childhood supratentorial primitive neuroectodermal tumours, childhood visual pathway and hypothalamic glioma and other childhood brain tumours;

breast cancer;

digestive/gastrointestinal related cancer such as anal cancer, extrahepatic bile duct cancer, gastrointestinal carcinoid tumour, gastrointestinal stroma tumour (GIST), cholangiocarcinoma , colon cancer, esophageal cancer, gallbladder cancer, adult primary liver cancer (hepatocellular carcinoma, hepatoblastoma) childhood liver cancer, pancreatic cancer, rectal cancer, small intestine cancer and stomach (gastric) cancer;

endocrine related cancer such as adrenocortical carcinoma, gastrointestinal carcinoid tumour, islet cell carcinoma (endocrine pancreas), parathyroid cancer, pheochromocytoma, pituitary tumour and thyroid cancer;

eye related cancer such as intraocular melanoma, and retinoblastoma;

genitourinary related cancer such as bladder cancer, kidney (renal cell) cancer, penile cancer, prostate cancer, transitional cell renal pelvis and ureter cancer, testicular cancer, urethral cancer, Wilms' tumour and other childhood kidney tumours;

germ cell related cancer such as childhood extracranial germ cell tumour, extragonadal germ cell tumour, ovarian germ cell tumour and testicular cancer;

gynecologic cancer such as cervical cancer, endometrial cancer, gestational trophoblastic tumour, ovarian epithelial cancer, ovarian germ cell tumour, ovarian low malignant potential tumour, uterine sarcoma, vaginal cancer and vulvar cancer;

head and neck related cancer such as hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, parathyroid cancer and salivary gland cancer;

hematologic/blood related cancer such as leukemias, such as adult acute lymphoblastic leukemia, childhood acute lymphoblastic leukemia, adult acute myeloid leukemia, childhood acute myeloid leukemia, chronic lymphocytic leukemia, chronic myelogenous leukemia and hairy cell leukemia; and lymphomas, such as AIDS-related lymphoma, cutaneous T-cell lymphoma, adult Hodgkin's lymphoma, childhood Hodgkin's lymphoma, Hodgkin's lymphoma during pregnancy, mycosis fungoides, adult non-Hodgkin's lymphoma, childhood non-Hodgkin's lymphoma, non-Hodgkin's lymphoma during pregnancy, primary central nervous system lymphoma, Sezary syndrome, cutaneous T-cell lymphoma and Waldenström's macroglobulinemia and other hematologic/blood related cancer such as chronic myeloproliferative disorders, multiple myeloma/plasma cell neoplasm, myelodysplastic syndromes and myelodysplastic/myeloproliferative diseases;

musculoskeletalrelated cancer such as Ewing's family of tumours, osteosarcoma, malignant fibrous histiocytoma of bone, childhood rhabdomyosarcoma, adult soft tissue sarcoma, childhood soft tissue sarcoma and uterine sarcoma; hemangiosarcomas and angiosarcoma;

neurologicrelated cancer such as adult brain tumour, childhood brain tumour, brain stem glioma, cerebellar astrocytoma, cerebral astrocytoma/malignant glioma, ependmoma, medulloblastoma, supratentorial primitive neuroectodermal tumours, visual pathway and hypothalamic glioma and other brain tumours such as neuroblastoma, pituitary tumour and primary central nervous system lymphoma;

respiratory/thoracicrelated cancer such as non-small cell lung cancer, small cell lung cancer, malignant mesothelioma, thymoma and thymic carcinoma;

skin related cancer such as cutaneous T-cell lymphoma, Kaposi's sarcoma, melanoma, Merkel cell carcinoma and skin cancer;

Small blue round cell tumours.

In particular, the anti-IGF antibody molecules of the invention and pharmaceutical compositions containing them are beneficial in the treatment of cancers of the hematopoietic system including leukemias, lymphomas and myelomas, cancers of the gastrointestinal tract including esophageal, gastric, colorectal, pancreatic, liver and gall bladder and bile duct cancer; kidney, prostate and bladder cancer; gynecological cancers including breast, ovarian, cervical and endometrial cancer; skin and head and neck cancers including malignant melanomas; pediatric cancers like Wilms' tumour, neuroblastoma and Ewing' sarcoma; brain cancers like glioblastoma; sarcomas like osteosarcoma, soft tissue sarcoma, rhabdomyosarcoma, hemangiosarcoma; lung cancer, mesothelioma and thyroid cancer.

In a preferred aspect of the invention, the anti-IGF antibody molecules of the invention and pharmaceutical compositions containing them are beneficial in the treatment of non-small cell lung cancer (NSCLC), in particular locally advanced or metastatic NSCLC (stage IIIB/IV). In this context, the anti-IGF antibody molecules of the invention can be combined with platinum-based chemotherapy, in particular paclitaxel/carboplatin or gemcitabine/cisplatin platinum doublet therapy.

In a further preferred aspect of the invention, the anti-IGF antibody molecules of the invention and pharmaceutical compositions containing them are beneficial in the treatment of hepatocellular carcinoma, in particular locally advanced or hepatocellular carcinoma (stage III/IV). In this context, the anti-IGF antibody molecules of the invention can be combined with sorafenib (Strumberg D., 2005).

In another embodiment, the anti-IGF antibody molecules and pharmaceutical compositions containing them are useful for non-cancerous hyperproliferative disorders such as, without limitation, psoriasis and restenosis after angioplasty. In addition, based on the recent observation (Reinberg, 2008) that a gene mutation that decreases the activity of IGF-1 has a positive effect on longevity, the antibodies of the invention have the potential to be useful, when applied to adults, in therapies to slow aging and prevent age-related diseases.

Thus, in a further aspect, the present invention relates to the use of an antibody molecule as decribed above for the preparation of a medicament for the treatment of a cancerous disease outlined above.

In another aspect, the present invention relates to a pharmaceutical composition as described above for the treatment of a cancerous disease as outlined before.

In another aspect, the present invention relates to a method for treating a patient suffering from a cancerous disease as outlined above, comprising administering to said patient an effective amount of a pharmaceutical composition as described herein.

Depending on the disorder to be treated, the anti-IGF antibody molecule of the invention may be used on its own or in combination with one or more additional therapeutic agents, in particular selected from DNA damaging agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the anti-IGF antibody molecule.

In certain embodiments, the additional therapeutic agent may be, without limitation, one or more inhibitors selected from the group of inhibitors of EGFR, VEGFR, HER2-neu, AuroraA, AuroraB, PLK and PI3 kinase, FGFR, PDGFR, Raf, KSP or PDK1.

Further examples of additional therapeutic agents are inhibitors of CDK, Akt, src/bcr-abl, cKit, cMet/HGF, c-Myc, Flt3, HSP90, hedgehog antagonists, inhibitors of JAK/STAT, Mek, mTor, NFkappaB, the proteasome, Rho, an inhibitor of wnt signaling or an ubiquitination pathway inhibitor.

Examples for Aurora inhibitors are, without limitation, PHA-739358, AZD-1152, AT-9283, CYC-116, R-763, VX-667, MLN-8045, PF-3814735, SNS-314, VX-689, GSK-1070916, TTP-607, PHA-680626, MLN-8237 and ENMD-2076.

An example for a PLK inhibitor is GSK-461364.

Examples for raf inhibitors are BAY-73-4506 (also a VEGFR inhibitor), PLX-4032, RAF-265 (also a VEGFR inhibitor), sorafenib (also a VEGFR inhibitor), XL-281, and Nevavar (also an inhibitor of the VEGFR).

Examples for KSP inhibitors are ispinesib, ARRY-520, AZD-4877, CK-1122697, GSK-246053A, GSK-923295, MK-0731, SB-743921, LY-2523355, and EMD-534085.

Examples for a src and/or bcr-abl inhibitors are dasatinib, AZD-0530, bosutinib, XL-228 (also an IGF-1R inhibitor), nilotinib (also a PDGFR and cKit inhibitor), imatinib (also a cKit inhibitor), NS-187, KX2-391, AP-24534 (also an inhibitor of EGFR, FGFR, Tie2, Flt3), KM-80 and LS-104 (also an inhibitor of Flt3, Jak2).

An example for a PDK1 inhibitor is AR-12.

An example for a Rho inhibitor is BA-210.

Examples for PI3 kinase inhibitors are PX-866, PX-867, BEZ-235 (also an mTor inhibitor), XL-147, XL-765 (also an mTor inhibitor), BGT-226, CDC-0941, GSK-1059615.

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, AV-299, ARQ-197, MetMAb, CGEN-241, BMS-777607, JNJ-38877605, PF-4217903, SGX-126, CEP-17940, AMG-458, INCB-028060, and E-7050.

An example for a c-Myc inhibitor is CX-3543.

Examples for Flt3 inhibitors are AC-220 (also an inhibitor of cKit and PDGFR), KW-2449, LS-104 (also an inhibitor of bcr-abl and Jak2), MC-2002, SB-1317, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are, tanespimycin, alvespimycin, IPI-504, STA-9090, MEDI-561, AUY-922, CNF-2024, and SNX-5422.

Examples for JAK/STAT inhibitors are CYT-997 (also interacting with tubulin), TG-101348 (also an inhibitor of Flt3), and XL-019.

Examples for Mek inhibitors are ARRY-142886, AS-703026, PD-325901, AZD-8330, ARRY-704, RDEA-119, and XL-518.

Examples for mTor inhibitors are rapamycin, temsirolimus, deforolimus (which also acts as a VEGF inhibitor), everolimus (a VEGF inhibitor in addition), XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are masitinib, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), sunitinib (also an inhibitor of Flt3, PDGFR, VEGFR), and XL-820 (also acts as a VEGFR- and PDGFR inhibitor), imatinib (also a bcr-abl inhibitor), nilotinib (also an inhibitor of bcr-abl and PDGFR).

Examples for hedgehog antagonists are IPI-609, CUR-61414, GDC-0449, IPI-926, and XL-139.

Examples for CDK inhibitors are seliciclib, AT-7519, P-276, ZK-CDK (also inhibiting VEGFR2 and PDGFR), PD-332991, R-547, SNS-032, PHA-690509, PHA-848125, and SCH-727965.

Examples for proteasome inhibitors/NFkappaB pathway inhibitors are bortezomib, carfilzomib, NPI-0052, CEP-18770, MLN-2238, PR-047, PR-957, AVE-8680, and SPC-839.

An example for an ubiquitination pathway inhibitor is HBX-41108.

Examples for anti-angiogenic agents are inhibitors of the FGFR, PDGFR and VEGF(R), and thalidomides, such agents being selected from, without limitation, BIBF 1120 (Vargatef®), bevacizumab, motesanib, CDP-791, SU-14813, telatinib, KRN-951, ZK-CDK (also an inhibitor of CDK), ABT-869, BMS-690514, RAF-265, IMC-KDR, IMC-18F1, IMiDs, thalidomide, CC-4047, lenalidomide, ENMD-0995, IMC-D11, Ki-23057, brivanib, cediranib, 1B3, CP-868596, IMC-3G3, R-1530 (also an inhibitor of Flt1), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, PF-337210, aflibercept, E-7080, CHIR-258, sorafenib tosylate (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL-880 (also an inhibitor of cMet), XL-647 (also an inhibitor of EGFR and EphB4), XL-820 (also an inhibitor of cKit), nilotinib (also an inhibitor of cKit and brc-abl), CYT-116, PTC-299, BMS-584622, CEP-11981, dovitinib, CY-2401401, and ENMD-2976.

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, nimotuzumab, zalutumumab; examples for small molecule EGFR inhibitors are gefitinib, erlotinib and vandetanib (also an inhibitor of the VEGFR). Another example for an EGFR modulator is the EGF fusion toxin.

Further EGFR and/or Her2 inhibitors useful for combination with an anti-IGF antibody molecule of the invention are BIBW 2992 (Tovok®), lapatinib, trastuzumab, pertuzumab, XL-647, neratinib, BMS-599626 ARRY-334543, AV-412, mAB-806, BMS-690514, JNJ-26483327, AEE-788 (also an inhibitor of VEGFR), AZD-8931, ARRY-380 ARRY-333786, IMC-11F8, Zemab, TAK-285, AZD-4769.

Other agents that may be advantageously combined in a therapy with the anti-IGF antibody molecule of the invention are tositumumab and ibritumomab tiuxetan (two radiolabelled anti-CD20 antibodies); ofatumumab, rituximab, LY-2469298, ocrelizumab, TRU-015, PRO-131921, FBT-A05, veltuzumab, R-7159 (CD20 inhibitors), alemtuzumab (an anti-CD52 antibody), denosumab, (an osteoclast differentiation factor ligand inhibitor), galiximab (a CD80 antagonist), zanolimumab (a CD4 antagonist), SGN40 (a CD40 ligand receptor modulator), XmAb-5485, Chi Lob 7/4, lucatumumab, CP-870893 (CD40 inhibitors), CAT-8015, epratuzumab, Y90-epratuzumab, inotuzumab ozogamicin (CD22 inhibitors), lumiliximab (a CD23 inhibitor), TRU-016 (a CD37 inhibitor), MDX-1342, SAR-3419, MT-103 (CD19 inhibitors), or mapatumumab, tigatuzumab, lexatumumab, Apomab, AMG-951 and AMG-655 (TRAIL receptor modulators).

Other chemotherapeutic drugs that may be used in combination with the anti-IGF antibody molecules of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortinsone, fluoxymesterone, medroxyprogesterone, octreotide, arzoxifene, pasireotide, vapreotide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, pemetrexed, pyrimidine analogues like 5-fluorouracil, capecitabine, decitabine, nelarabine, and gemcitabine, purine and adenosine analogues such as mercaptopurine thioguanine, cladribine and pentostatin, cytarabine, fludarabine); antitumour antibiotics (e.g. anthracyclines like doxorubicin, daunorubicin, epirubicin and idarubicin, mitomycin-C, bleomycin dactinomycin, plicamycin, mitoxantrone, pixantrone, streptozocin); platinum derivatives (e.g. cisplatin, oxaliplatin, carboplatin, lobaplatin, satraplatin); alkylating agents (e.g. estramustine, meclorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan) and miscellaneous chemotherapeutics such as amifostine, anagrelide, interferone alpha, procarbazine, mitotane, and porfimer, bexarotene, celecoxib.

In one aspect, the anti-IGF antibody molecules of the invention are used in combination with platinum-based chemotherapy, for example in combination with paclitaxel/carboplatin or gemcitabine/cisplatin platinum doublet therapy. In one embodiment, such combination therapy may be repeated several times, for examples 6 cycles (q3 weeks). This treatment may be followed by further repeated treatment (e.g. 6 cycles q3 weeks) with anti-IGF antibody molecule alone. This regimen can be used e.g. in the treatment of NSCLC. In another aspect, the anti-IGF antibody molecules of the invention are used in combination with sorafenib. In one embodiment, the anti-IGF antibody molecule may be administered repeatedly in intervals of 1-3 weeks, e.g. for 12 cycles, in combination with continuous administration of sorafenib. This regimen can be used e.g. in the treatment of hepatocellular carcinoma.

The anti-IGF antibody molecules of the invention, e.g. when used at lower concentrations, may also be combined with agents that target the IGF-1R. Such agents include antibodies that bind to IGF-1R (e.g. CP-751871, AMG-479, IMC-A12, MK-0646, AVE-1642, R-1507, BBB-022, SCH-717454, rhu Mab IGFR and novel chemical entities that target the kinase domain of the IGF1-R (e.g. OSI-906 or BMS-554417, XL-228, BMS-754807).

The anti-IGF antibody molecules of the invention may also be used in combination with other therapies including surgery, radiotherapy, endocrine therapy, biologic response modifiers, hyperthermia and cryotherapy and agents to attenuate any adverse effect, e.g. antiemetics and, in a preferred embodiment, antidiabetics, e.g. metformin.

The anti-IGF antibody molecules of the invention are also useful in diagnosis of cancers where elevated serum levels of IGF-1 and/or IGF-2 correlate with development or progression of disease, e.g. for determining elevated IGF-2 levels due to loss of imprinting (LOI), an epigenetic alteration affecting the insulin-like growth factor II gene (IGF2). In certain embodiments, an antibody for diagnostic applications, e.g. for detection of IGF-1 in human tissue sections by immunohistological staining, is a chimeric antibody that is derived from a human antibody. In such antibody, the constant regions, or parts thereof, have been replaced by the respective sequences from an antibody of another species, e.g. mouse. By using such chimeric antibody as a primary antibody, the secondary antibody, e.g. a goat antibody which specifically reacts with the murine Fc portion, will specifically recognize the murine sequences of the chimeric primary antibody and not bind to the Fc portions of the other human immunoglobulin molecules that are present in the human tissue sample. Thus, undesired background staining is avoided.

The antibodies of the invention, by blocking IGF-1 and IGF-2 mediated signal transduction, may also be useful for the control of body weight and adipose tissue formation. To this end, the antibodies of the invention are administered alone or in combination with other anti-obesity drugs.

Materials & Methods

Selection of High Affinity Fully Human Antibodies that Bind IGF-1

Selection of specific Fab fragment clones from the human combinatorial antibody library (HuCAL Gold) (Knappik et al., 2000) that bind human IGF-1 with low nanomolar affinity is performed essentially as described by Rauchenberger et al., 2003, in three panning cycles. In order to identify Fab fragments with improved affinity to human IGF-1, several of these 'parental' Fab clones are subjected to 'in vitro affinity maturation' essentially as described by Nagy et al., 2002. The L-CDR3 (light chain CDR3) and H-CDR2 (heavy chain CDR2) sequences of each clone are separately diversified by substituting the parental sequence with approximately $10^8$ L-CDR3 and H-CDR2 cassettes from HuCAL (Knappik et al., 2000). Phages are prepared from the resultant 'maturation libraries' and each library is subjected to solution pannings on human IGF-1. In order to select the highest affinity human IGF-1 binders, the solution pannings are performed under normal and increased stringency washing conditions according to methods known in the art, with antigen reduction, and with and without blocking by human insulin. The panning outputs after three phage panning rounds are subcloned into a Fab expression vector and the affinity of each Fab for human IGF-1 determined by an electrochemiluminescence-based equilibrium titration technology developed by BioVeris (Witney, Oxfordshire, UK) essentially as described by Haenel et al., 2005. The Fab clones with the best IGF-1 affinities are sequenced, then converted into human IgG1 antibodies as described by Krebs et al., 2001, with subnanomolar affinity to human IGF-1 without any change in specificity compared with the parental antibodies.

Cloning and Recombinant Expression of IgG1 Antibodies

Variable heavy chain regions (VH) and variable light chain regions (VL) are excised from the Fab expression vectors by restriction enzyme digestion and ligated into compatible restriction enzyme sites of pcDNA3.1 based plasmids containing the human IgG1 heavy chain and human Igλ light chain constant regions respectively. EndoFree plasmid preparations (Qiagen) are prepared and the heavy and light chain plasmids are co-transfected into HEK293 freestyle cells (Invitrogen) at a concentration of 1 mg/L of each plasmid according to the supplier's protocol. After 72 hours the supernatant is harvested and the IgG concentration determined by ELISA. Antibody is purified on a modified protein A column (GE Healthcare), eluted into a citrate buffer and then dialysed to a concentration of 2.5 mg/ml in PBS. Alternatively, a CHO cell line stably integrated with the antibody expression plasmids is generated and used to produce the antibodies.

Surface Plasmon Resonance Analysis for Determining Affinity Constants a) Antibody Capture Method The sensor chip is coated with approximately 1000 RU of the reference antibody in flow cell 1 and approximately 1000 RU of a rabbit-anti-human Fc-gamma-specific antibody in flow cell 2 using the coupling reagents from an amine coupling kit. A target of 1000 RU is set in the surface preparation wizard of the Biacore 3000 software at a flow rate of 5 µl/min Running buffer used is HBS-EP. The affinity measurements are made using the following parameters: 20 µl/min flow (HCB running buffer:); 25° C. detection temperature; Fc1, Fc2 flow paths; Fc1, Fc2 detection; anti-IGF-huMAb-capturing: 3 min of a 1 µg/ml solution; 5 min IGF-Ag-association; 5 min IGF-Ag-dissociation; regeneration: 30 sec pulse with 50 mM HCl. The IGF antigens are diluted to 500, 250, 125, 62.5 and 31.3 nM in running buffer (HCB) and the different antigen dilutions are run singly over Fc1 and Fc2 with random order. Blank runs using running buffer only are run in-between. A blank run curve is subtracted from each binding curve before affinity analysis. Data evaluation is performed using the BIAevaluation software (version 4.1, Biacore, Freiburg, Germany). The dissociation and association phases of the kinetics are fitted separately. For the separate fit of the $k_{diss}$ values a time-frame of the initial 200-300 seconds in the dissociation phase is used (range of steady decrease of signal). For the separate fit of the $k_{ass}$ values, initial time frames of approx 100 seconds are used (range of steady increase of signal) and for calculation the individual $k_{diss}$ values are used with the 1:1 Langmuir association model. The average values with the standard deviations of the kinetic data together with the corresponding dissociation ($K_D$) and association ($K_A$) constants are calculated.

b) IGF Coating Method

The determination of binding constants of IGF antibodies to IGF ligands when the sensor chip is coated with IGF ligands is essentially performed as described above except that the sensor chip is coated with 35.1 pg/mm$^2$ and 38.5 pg/mm$^2$ IGF-1 and IGF-2 respectively. The antibodies are then flowed over the chip at the following concentrations: 50, 25, 12.5, 6.25, 3.12 nM.

Measurement of Binding to Human, Murine and Rat IGFs and to Human Insulin in Immunosorbent Assays Fully human IgG1 antibodies that bound with high affinity to IGF-1 are also tested for binding to human IGF-1 in direct immunosorbent assays (ELISA). Assays are performed by coating human IGF-1 (R&D Systems, No. 291-G1) to 96-well Maxisorb plates at a concentration of 0.5 µg/ml overnight at 4° C. (100 µl/well). Coating buffer alone is used as a control for unspecific binding. Wells are then washed once with washing buffer (1×TBS-T) and residual binding sites are blocked with 200 µl blocking buffer for 1 hour at room temperature on an orbital shaker followed by a further wash cycle. Serial three-fold dilutions of each test antibody in blocking buffer are prepared directly on the coated plates. Typical concentrations used are 50, 16.6, 5.6, 1.8, 0.6, 0.2, and 0.07 ng/ml. Blocking buffer alone is used as a positive control. The plates are then incubated for 2 hours at room temperature with agitation. After three wash cycles 100 µl/well of HRPO-conjugated anti-human IgG secondary reagent (Jackson ImmunoResearch Inc.) diluted in blocking buffer is added to all wells. After 2 hours incubation at room temperature with agitation the plates are washed three-times and 100 µl/well of TMB substrate solution (equal amounts of solution A and B) are pipetted into all wells. The plates are incubated for 10-20 min at RT with agitation and then the reaction is stopped by addition of 100 µl/well 1 M phosphoric acid. The absorbance is measured at a wavelength of 450 nm (reference 650 nm).

Binding of the fully human IGF-1 binding IgG1 antibodies to mouse IGF-1 (R&D Systems, No. 791-MG), rat IGF-1 (IBT, No. RU100), human IGF-2 (GroPep, No. FM001), mouse IGF-2 (R&D Systems, No. 792-MG), rat IGF-2 (IBT, No. AAU100), and human insulin (Roche) is also tested as described above for human IGF-1 (except that the concentration of human insulin used for coating is 3 µg/ml).

In Vitro Cell Proliferation Assays for Determining Neutralization Potency

The MCF-7 breast cancer derived cell line (ATCC, HTB-22) and COLO 205 colon cancer-derived cell line (ATCC #CCL-222) are plated in 96-well plates at a cell density of 1000 cells per well in serum-free RPMI medium. 10 ng/ml of either IGF-1 or IGF-2 is added in the presence or absence of a humanized isotype control antibody that does not bind IGF-1 or IGF-2, or antibodies 60814, 60819, and 60833 at concentrations of 12, 37, 111, 333, 1000 and 3000 ng/ml. Cells are cultured for 5 days then the relative cell number in each well determined using the CellTiter-Glo luminescent cell viability assay (Promega). Luminescence (LU=Luminescence Units) is recorded using a XFluor GENios Pro 4.

Ewing's Sarcoma-Derived Cell Line Growth Assay

The Ewing's sarcoma-derived cell lines TC-71 (ATCC #ACC516) and SK-ES-1 (ATCC #HTB86) are plated in 96-well plates at a density of 1000 cells per well in DMEM medium containing 1× NEAA, 1× sodium pyruvate, 1× glutamax and 10% fetal calf serum (FCS) and incubated overnight at 37° C. and 5% CO$_2$ in a humidified atmosphere. The following day a serial dilution of test antibody, humanized isotype control antibody (a humanized IgG1 antibody targeted to CD44-v6) that does not bind IGF-1 or IGF-2, rapamycin, or a combination of rapamycin and test antibody, are added to the cells. The typical concentrations used are 30, 10, 3.3, 1.1, 0.37, and 0.12 µg/ml (or 100, 10, 1, 0.1, 0.01, 0.001 nM rapamycin and test antibody for combination studies) and each dilution is performed in triplicate wells. The cells plus antibody are then incubated for 120 hours after which time the relative cell number in each well is determined using the CellTiter-Glo luminescent cell viability assay (Promega). Luminescence (LU=Luminescence Units) is recorded using a XFluor GENios Pro 4 and for data analysis the mean value from triplicate wells is taken and fitted by iterative calculations using a sigmoidal curve analysis program (Graph Pad Prism) with variable Hill slope.

Western Blot Analysis of Phosphorylated AKT and PTEN Levels

SK-ES-1 cells are plated in 6-well plates in medium containing 10% fetal bovine serum and after overnight incubation they are treated with either 100 nM isotype control antibody (a humanized IgG1 antibody targeted to CD44-v6) that does not bind IGF-1 or IGF-2, 100 nM 60819, 100 nM rapamycin, or a combination of 100 nM 60819 and 100 nM rapamycin. 24 hours later the cells are lysed and the cell lysate frozen after the protein concentration is determined by Bradford assay. Western blotting is performed by applying 30 µg of protein lysates to an SDS PAGE gel (BioRad) and the gel blotted on a Citerian gel blotting sandwich. Western blots are incubated overnight with a rabbit anti-beta actin (control) antibody, a rabbit anti-PTEN antibody (Cell Signaling #9559), or a rabbit anti-phospho-pAKT antibody (Cell Signaling #4060), at 1:5000 (anti-beta actin), 1:1000 (anti-PTEN), or 1:2000 (anti-phosphoAKT) dilutions in 1% milk powder. Following washing in TBS an anti-rabbit IgG HRPO-conjugated secondary antibody (Amersham) is applied for 1 hour and after further washes in TBS antibody reactivity is detected by ECL and captured on Hyperfilm (Amersham).

In Vitro Combination of Anti-IGF Antibody with EGFR Inhibitor in NSCLC-Derived Cell Line The NSCLC-derived cell line A-549 (ATCC #CCL-185) is plated in 96-well plates at a density of 1000 cells per well in RPMI 1640 medium containing 2 mM L-glutamine and 10% fetal bovine serum and incubated overnight at 37° C. and 5% CO$_2$ in a humidified atmosphere. The following day a serial dilution of test IGF antibody, erlotinib/Tarceva, or a combination of test IGF antibody and erlotinib are added to the cells. The typical concentrations of the test IGF antibody used are 30000, 10000, 3333, 1111, 370, 123, 41, 14 ng/mL, and the typical concentration of erlotinib used are 20000, 6667, 2222, 741, 247, 82, 27, 9 nM, and each dilution is performed in triplicate wells. The cells are then incubated for 120 hours after which time the relative cell number in each well is determined using the CellTiter-Glo luminescent cell viability assay (Promega). Luminescence (LU=Luminescence Units) is recorded using a XFluor GENios Pro 4 and for data analysis the mean value from triplicate wells is taken and fitted by iterative calculations using a sigmoidal curve analysis program (Graph Pad Prism) with variable Hill slope.

Determination of the Effect on Total Murine and Total Rat Serum IGF-1 Levels

Single intravenous (bolus) administrations of 25, 12.5, 6.25, and 3.13 mg/kg of test IGF antibody are given to female athymic NMRI nude mice, 6-8 weeks old (n=5). Single 10 minute intravenous administrations of 30, 100, 200 mg/kg of antibody 60819 are given to male and female Wistar Han rats, 6-8 weeks old (n=4 male, 4 female). Prior to antibody treatment and 24 hours post administration a blood sample is taken, serum collected, and total murine or rat IGF-1 levels determined using the OCTEIA rat/mouse total IGF-1 immunocytometric assay. The assay is performed according to the manufacturer's instructions, absorbance is measured at 450 nm and evaluated using the SoftMax Pro software. A standard curve is used to determine the serum concentration of total IGF-1 in ng/ml. Statistical analysis is performed using the GraphPad Prism software.

Cell Based IGF-1R Phosphorylation ELISA

Mouse fibroblast cell lines recombinantly expressing human IGF-1R or human IR-A are maintained in DMEM supplemented with 10% heat inactivated FCS, 1 mM sodium pyrovate, 0.075% sodium bicarbonate, MEM NEAA, and 0.3 μg/ml puromycin at 37° C. and 5% $CO_2$ in a humidified incubator. Cells are detached with trypsin/EDTA, resuspended in growth medium and diluted to 100,000 cells/mL. 100 μL (10,000 cells) are seeded in wells of a sterile 96-well plate and incubated overnight in a humidified incubator at 37° C. and 5% $CO_2$. The cells are then starved with 100 μL/well assay medium (DMEM supplemented with 0.5% heat inactivated FCS; 1 mM sodium pyrovate, 0.075% sodium bicarbonate, and MEM NEAA) and incubated overnight as before. A range of test antibody concentrations prepared in assay medium is added to the cells, all samples are prepared in triplicate to determine the standard deviation for each assay condition. An IGF-1R antibody, αIR-3 (Calbiochem, No. GR11L) is also tested in these experiments. IGF-1 (20 ng/mL final concentration), IGF-2 (100 ng/mL final concentration), or human serum (20% final concentration) is then added and the plates incubated for 30 min in the humidified incubator. Cells are fixed by replacing the growth medium with 4% formaldehyde in PBS for 20 min at RT. After two wash cycles with 300 μL/well wash buffer (PBS with 0.1% Triton X-100) for 5 min (with agitation) the cells are quenched with 100 μL/well 1.2 wt % hydrogen peroxide in wash buffer for 30 minutes at RT. Cells are washed again with 300 μL/well washing buffer and blocked with 100 μL/well blocking buffer (5% BSA in wash buffer) for 60 min at RT with agitation. Blocking buffer is removed and 50 μl/well primary phopho-IGF-I receptor β (tyr1135/1136)/insulin receptor β (tyr1150/1151) antibody (Cell Signaling, No. 3024) diluted 1:1000 in blocking buffer is added. Plates are incubated overnight at 4° C. with agitation then washed three times as above and 50 μL/well anti-rabbit IgG goat immunoglobulins conjugated with horseradish peroxidase (Dako, No. P0448) diluted 1:500 in blocking buffer is added. After a 60 min incubation at RT with agitation the wells are washed twice with washing buffer as above and once with 300 μL PBS. 100 μL/well TMB substrate solution (Bender MedSystems, No. BMS406.1000) is added to the wells and incubated for 10 min with agitation, following this the reaction is stopped by adding 100 μL/well 1 M phosphoric acid and the absorbance read using a photometer (OD 450 nm, OD 650 nm as reference) Inhibition of IGF-1R or IR-A phosphorylation $IC_{50}$ values are determined by graphical analysis.

Fab-IGF-1 Co-crystallisation and Structure Determination

Monoclonal antibodies are prepared in a buffer of 100 mM Na-phosphate (pH 7.0) prior to papain digestion. Papain (Sigma Aldrich, P #3125) is activated in digestion buffer (phosphate buffer containing 10 mM cysteine hydrochloride, 4 mM EDTA, pH 7.0) following the manufacturer's instructions. IgG antibody is mixed with the activated papain (ratio enzyme:IgG=1:100) and the reaction is incubated at 37° C. on a rotor shaker overnight. Digestion is stopped by adding iodacetamid to a final concentration of 30 mM. To separate the Fab fragment from Fc fragments, Fc cleavage products and intact Mab, the digestion mix is loaded onto a Protein A MabSelect column equilibrated with phosphate buffer. The column is washed with column volumes of PBS, and the Fab fragment is collected in the flow-through and wash fractions. The Fc fragment and intact Mab are eluted from the column with 100 mM citrate buffer (pH 3.0) and subsequent size exclusion chromatography of the Fab fragment is performed using a HiLoad Superdex 75 column The column is run at 0.5 mL per min with 20 mM triethanolamine, 130 mM NaCl, pH 8.0. The protein concentration of Fab fragments is determined by measuring absorbance at 280 nm Quality of Fab fragments is analysed by Western Blotting and ELISA.

Fab-IGF-1 complex is generated by adding a 2-fold molar excess of the recombinant IGF-1 (Gropep; Receptor Grade) to the purified Fab which is then incubated overnight on a rotor shaker at 4° C. Concentration of the complex to (15 mg/mL) and removal of unbound IGF-1 is performed using an Amicon-Ultra device. Crystallization of the Fab:IGF-1 complex is carried out using various techniques such as hanging drop, sitting drop, and seeding. In one embodiment, the crystal is precipitated by contacting the solution with a reservoir that reduces the solubility of the proteins due to presence of precipitants, i.e., reagents that induce precipitation. Screening of various conditions lead to a suitable buffer system manipulated by addition of a precipitant and additives. The concentration of the precipitants is preferably between 5-50% w/v. The pH of the buffer is preferably about 3 to about 6. The concentration of the protein in the solution is preferably that of super-saturation to allow precipitation. The temperature during crystallization is preferably between 4 and 25° C.

The three dimensional structure of Fab:IGF-1 complex as defined by atomic coordinates is obtained from the X-ray diffraction pattern of the crystal and the electron density map derived there from. The diffraction of the crystals is better than 2 Å resolution. The crystals preferably have the space group P3221 (number 154) and unit cell dimensions of approximately=70 Å, b=70 Å, c=195 Å; and γ=120°. The method for determining the three dimensional structure is molecular replacement which involves use of the structure of a closely related molecule or receptor ligand complex. Model building and refining is done in several iterative steps to final R-factors (R and $R_{free}$) of 21 and 23% respectively.

Determination of Pharmacokinetic Parameters in Rats

Wistar rats are given five intravenous bolus administrations of 18, 52, and 248 mg/kg antibody every 72 hours. At various time points a blood sample is taken and the human antibody concentration in the plasma is determined by sandwich ELISA. This allowed the mean pharmacokinetic parameters of the antibody to be calculated on the first day of dosing and half-life is calculated after the last day of dosing (with t(n) =1008 hours).

EXAMPLE 1

Selection of High Affinity Antibodies that Bind IGF-1

In order to identify Fab fragments with improved affinity to human IGF-1, several 'parental' Fab clones that are identified to bind IGF-1 with low nanomolar affinity are subjected to 'in vitro affinity maturation' where the L-CDR3 and H-CDR2 sequences of each clone are separately diversified by substituting the parental sequence with a library of new L-CDR3 and H-CDR2 sequences. The resultant 'maturation libraries' are subjected to solution pannings on human IGF-1 and the clones with the best affinity are selected for convertion into IgG1 antibodies and tested further. The three antibodies with the best human IGF-1 affinities are 60814, 60819, and 60833 which had affinities ($K_D$) of 180, 190, and 130 pM respectively (shown in Table 1) as determined by an electrochemiluminescence-based equilibrium titration method.

TABLE 1

IGF-1 BINDING SUMMARY

| Antibody | Affinity (pM) |
|---|---|
| 60814 | 180 |
| 60819 | 190 |
| 60833 | 130 |

The antibodies are also tested for their binding to human, murine, and rat IGF-1 and IGF-2, and human insulin, in immunosorbent assays. This demonstrated that 60814, 60819, and 60833 show comparable cross-reactive binding with mouse and rat IGF-1, and human, murine and rat IGF-2, but no reactivity to human insulin (at the highest concentration tested, 50 ng/ml) (FIGS. 1A-1G).

Affinity constants for binding of the antibodies to human, mouse, and rat IGF-1 and IGF-2 is also determined by surface plasmon resonance (Biacore) analysis. The method involves capturing the antibodies on the sensor and flowing the IGF antigens over the captured antibodies, thus overcoming any avidity effect that could occur if the IGF antigens are coated onto the sensor and the antibodies added. The affinity constants using this method for antibody 60833 are shown in Table 2 where it can be seen that the measured $K_D$ values for human IGF-1 and human IGF-2 are 0.07 nM and 0.9 nM respectively.

TABLE 2

AFFINITY CONSTANTS OF ANTIBODY 60833 FOR HUMAN, MOUSE, AND RAT IGF-1 AND IGF-2 DETERMINED BY SURFACE PLASMON RESONANCE (ANTIBODY CAPTURE METHOD)

| Antigen | $K_{on}$ [$M^{-1}s^{-1}$] | $K_{off}$ [$s^{-1}$] | $K_D$ [nM] |
|---|---|---|---|
| Human IGF-1 | $4.74 \times 10^6$ | $3.01 \times 10^{-4}$ | 0.07 |
| Mouse IGF-1 | $1.00 \times 10^6$ | $3.23 \times 10^{-4}$ | 0.33 |
| Rat IGF-1 | $3.81 \times 10^6$ | $2.53 \times 10^{-4}$ | 0.07 |
| Human IGF-2 | $3.97 \times 10^6$ | $3.53 \times 10^{-3}$ | 0.913 |
| Mouse IGF-2 | $8.68 \times 10^5$ | $1.1 \times 10^{-2}$ | 13.4 |
| Rat IGF-2 | $2.56 \times 10^6$ | $6.13 \times 10^{-3}$ | 2.41 |

EXAMPLE 2

Inhibition of IGF Signalling

Figure 2A:
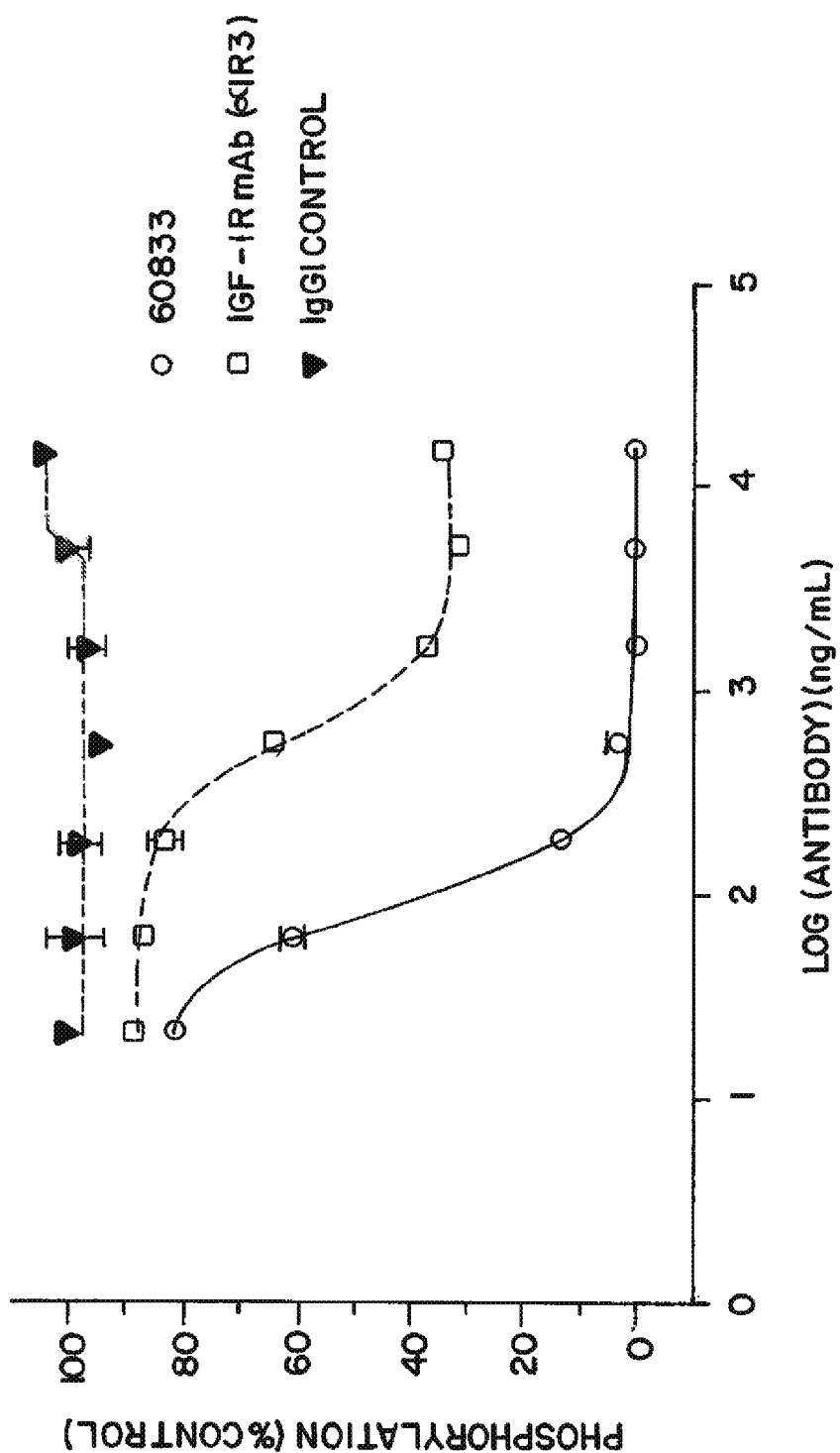
FIG. 2 shows typical titrations of antibody 60833 neutralising IGF-1 (20 ng/mL) (FIG. 2A) and IGF-2 (100 ng/mL) (FIG. 2B) induced phosphorylation of the IGF-1R using a cell based ELISA.
Figure 2B:
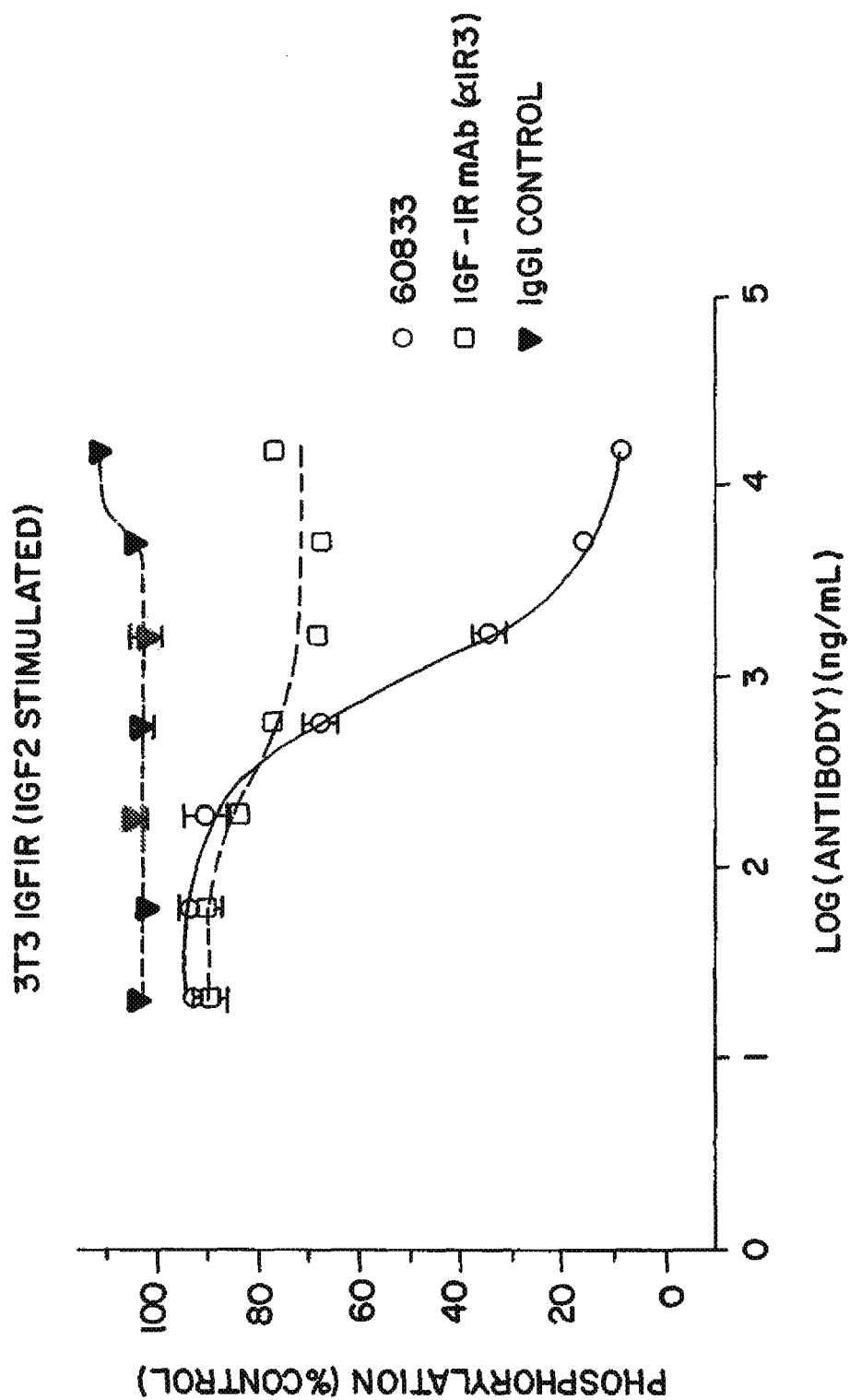

The first signalling event which occurs following binding of IGFs to the IGF-1R is the phosphorylation of the IGF-1R. A cell-based ELISA assay is used to measure the inhibition of IGF induced IGF-1R phosphorylation by the antibody 60833. The potency and effectiveness (of up to 15 µg/mL (100 nM)) of 60833 in neutralising recombinant bioactive IGF-1 and IGF-2 induced IGF-1R phosphorylation is determined As shown in Table 3 and example FIG. 2 60833 potently and effectively inhibits IGF-1 (FIG. 2A) and IGF-2 (FIG. 2B) induced signalling. In the same assay the IGF-1R targeted mAb αIR3 is much less potent and effective with respect to IGF-1 induced signalling, and displays a very weak effect on IGF-2 induced signalling.

Figure 3A:
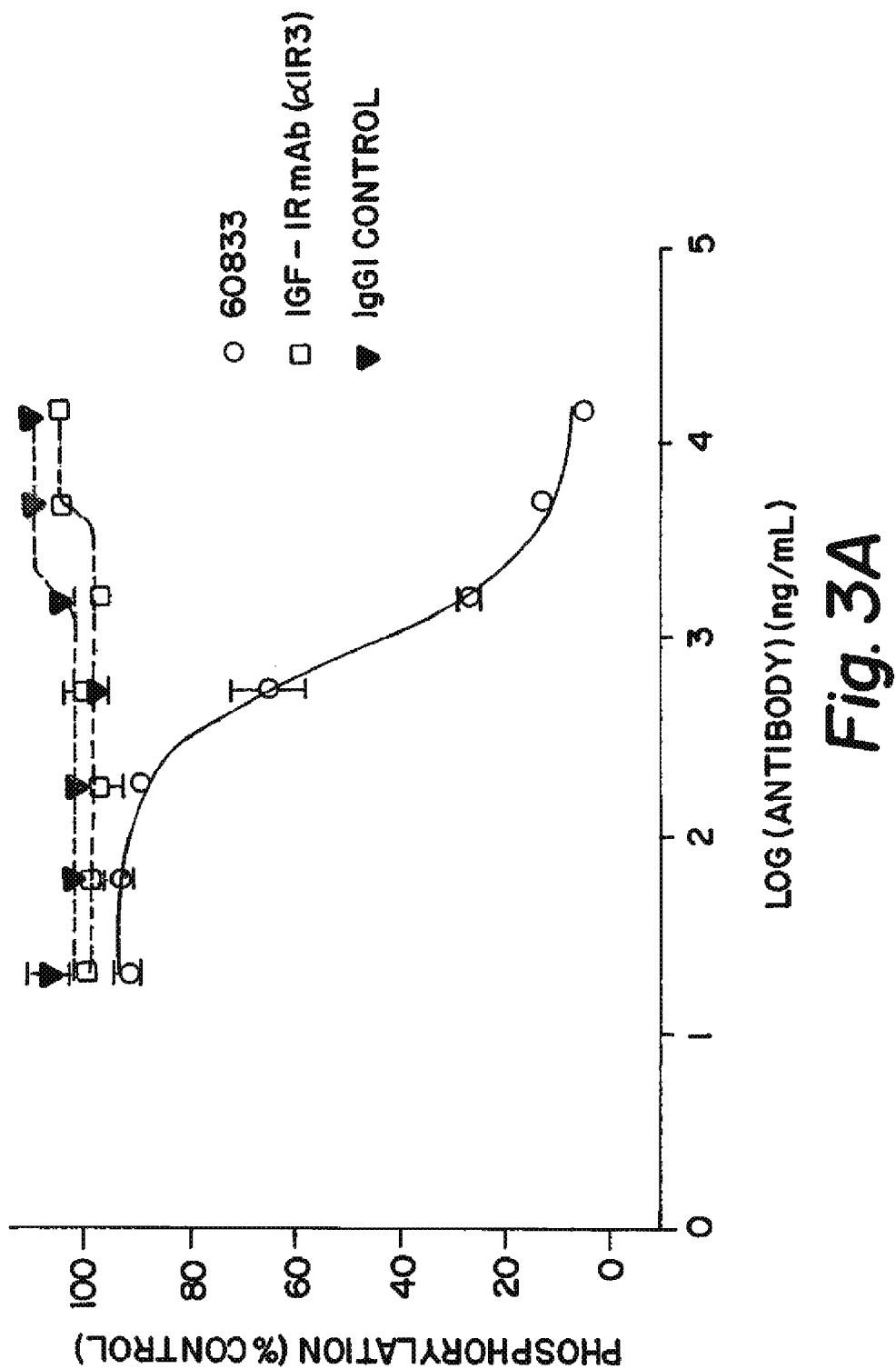
FIG. 3A shows a typical titration of antibody 60833 neutralising IGF-2 (100 ng/mL) induced IR-A phosphorylation.

A similar cell based IR-A phosphorylation ELISA is used to demonstrate that 60833 can also inhibit IGF-2 signalling via IR-A. As shown in Table 4 and example FIG. 3A, 60833 potently and effectively inhibits IGF-2 induced IR-A phosphorylation. In contrast, αIR3, which cannot bind IR-A, shows no inhibitory effect.

Figure 3B:
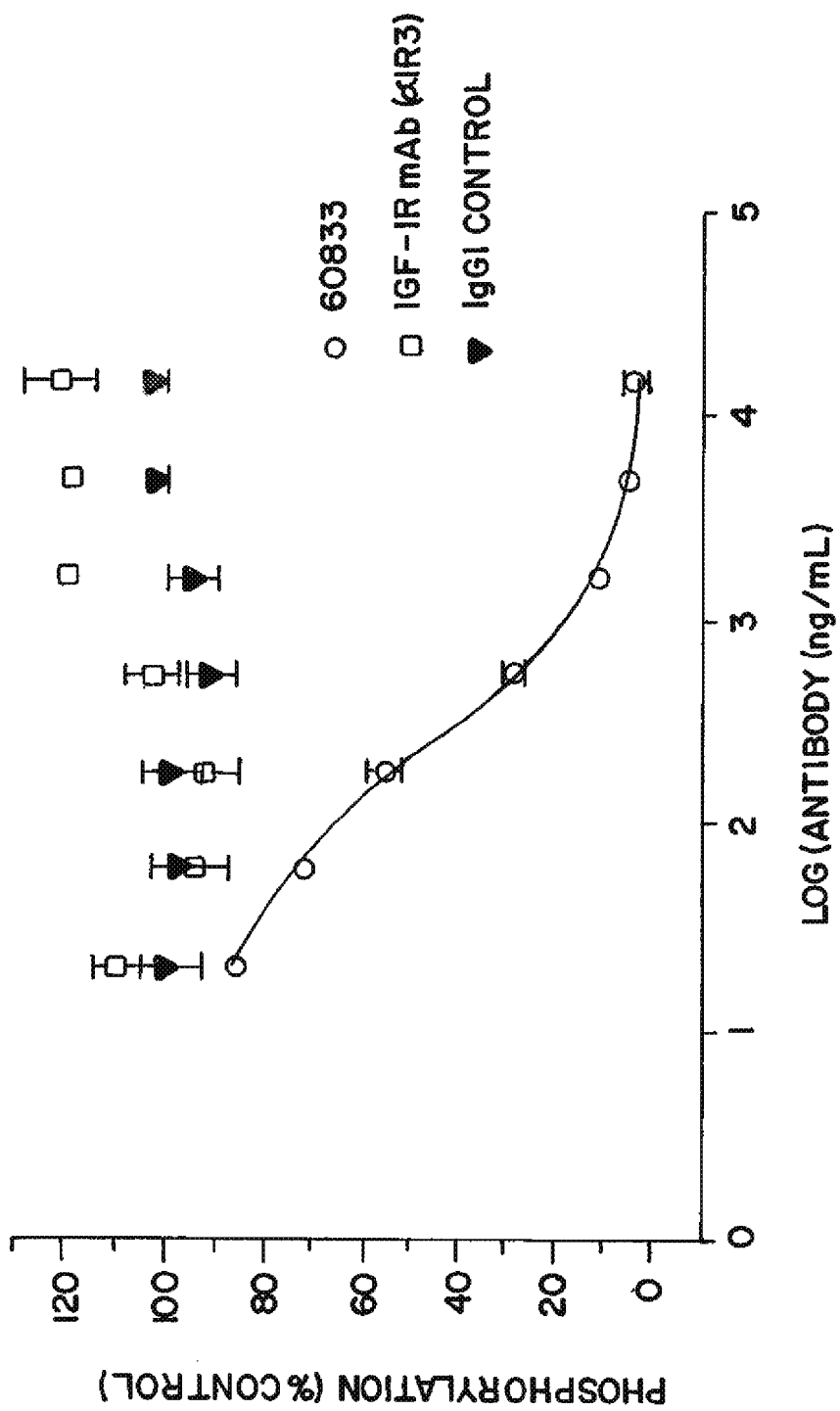
FIG. 3B shows a typical titration of antibody 60833 neutralising human serum (20%) induced phosphorylation of the IGF-1R. Both assays are performed using cell based ELISAs.
Figure 4A:
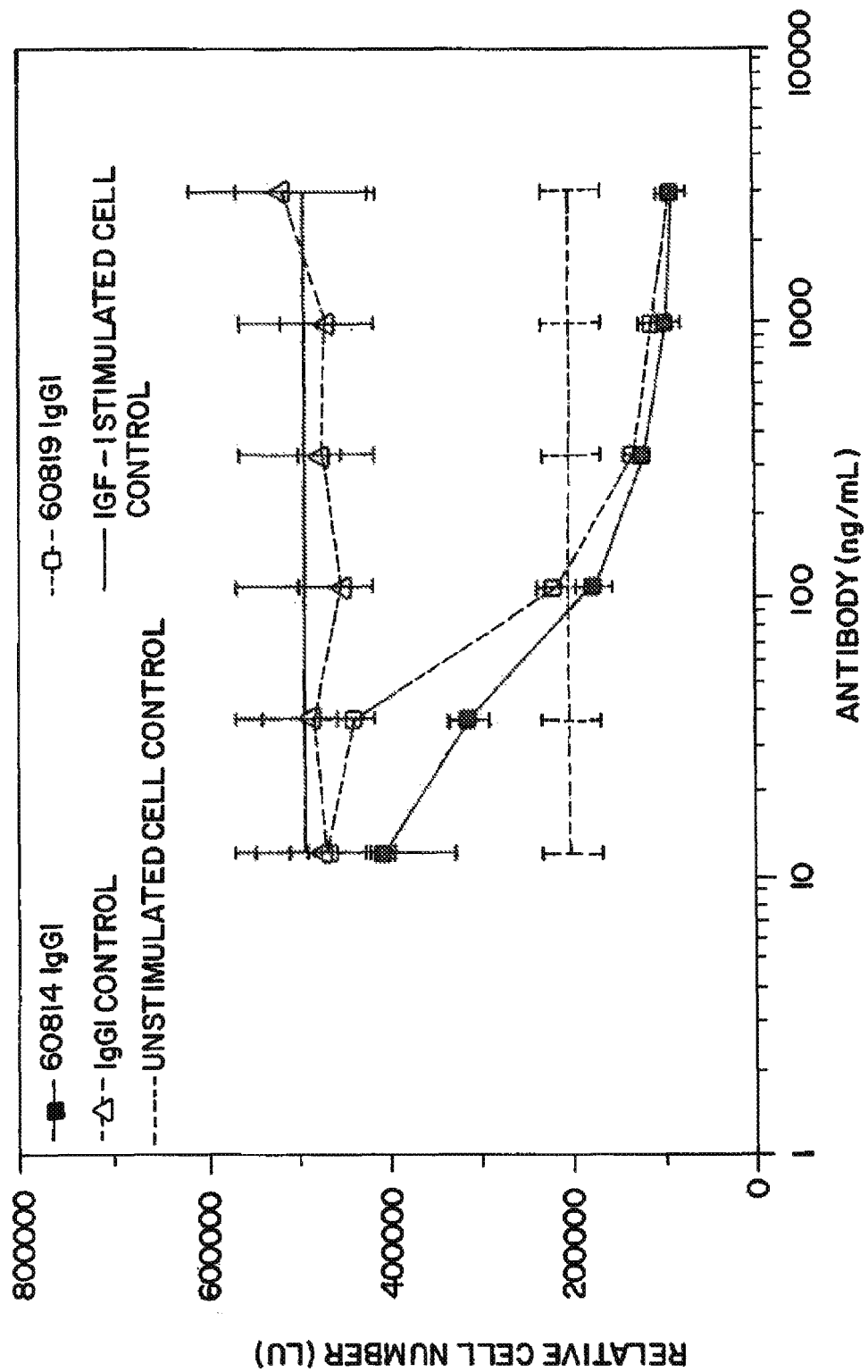
FIGS. 4A-4D show the effect of antibodies 60814 and 60819 on IGF-1 (FIGS. 4A and 4C) and IGF-2 (FIGS. 4B and 4D) stimulated MCF-7 (FIGS. 4A and 4B) and COLO 205 (FIGS. 4C and 4D) cell proliferation.
Figure 4B:
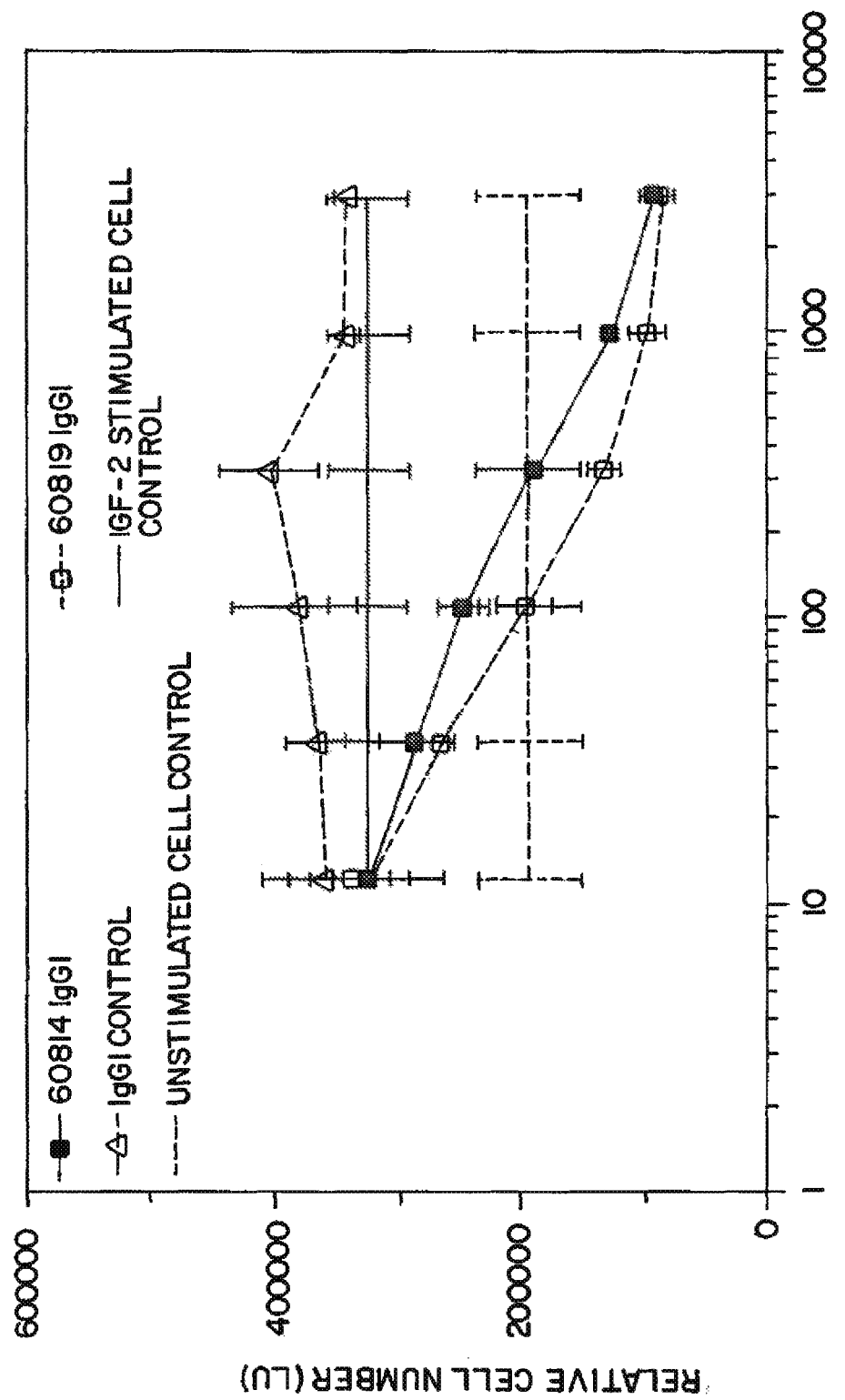
Figure 4C:
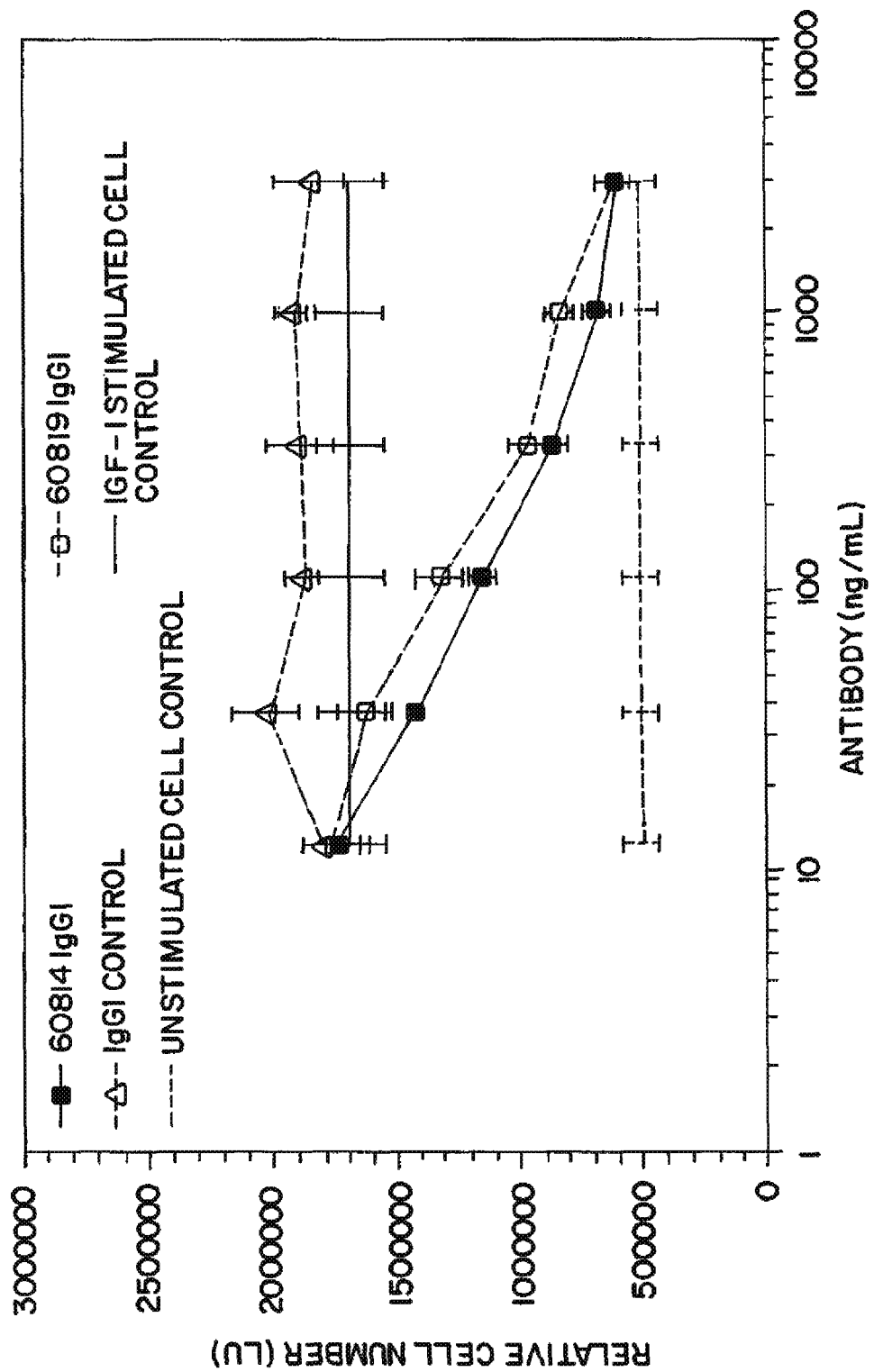
Figure 4D:
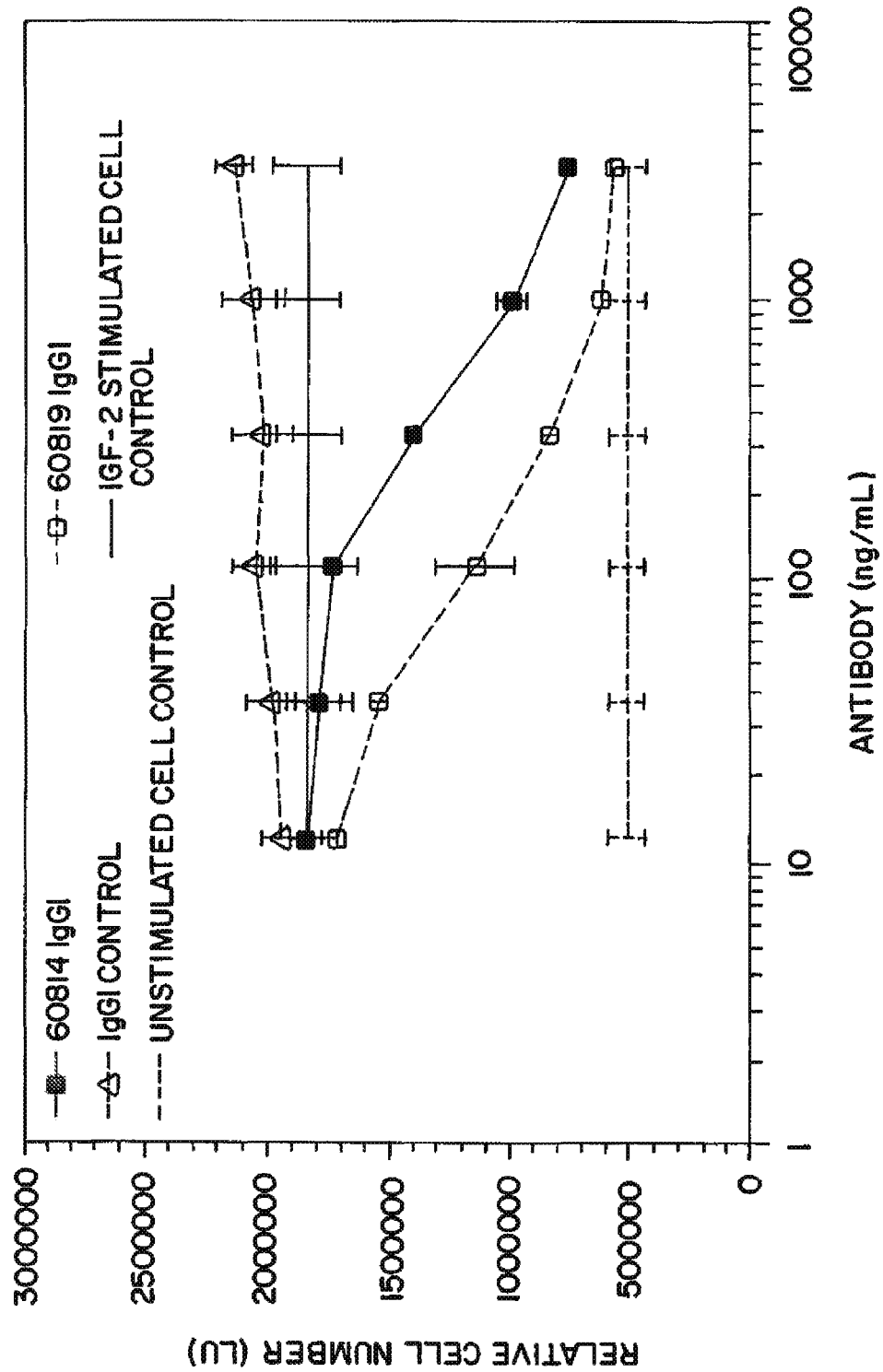

The level of IGF bioactivity in human serum or plasma samples can also be measured using the IGF-1R phosphorylation cell based ELISA. This is used to determine the potency and effectiveness (up to 15 µg/mL (100 nM)) of 60833 in neutralising human serum IGF bioactivity. As shown in Table 3 and example FIG. 3B 60833 potently and effectively inhibits IGF bioactivity in human serum.

TABLE 3

EFFECT OF 60833 ON IGF-1R PHOSPHORYLATION

| IGF-1R Phosphorylation Stimulus | Inhibitor | $IC_{50}$ (µg/mL) | % Remaining Phosphorylation at 15 µg/mL (100 nM) Inhibitor |
|---|---|---|---|
| IGF-1 (20 ng/mL) | 60833 | 0.09 | 0 |
|  | αIR3 | 1.16 | 35 |
|  | Control IgG | >15 | 108 |
| IGF-2 (100 ng/mL) | 60833 | 1.12 | 7 |
|  | αIR3 | >15 | 76 |
|  | Control IgG | >15 | 108 |
| Human Serum Pooled from Healthy Donors (20%) | 60833 | 0.25 | 5 |
|  | αIR3 | >15 | 120 |
|  | Control IgG | >15 | 110 |

TABLE 4

EFFECT OF 60833 ON IR-A PHOSPHORYLATION

| IR-A Phosphorylation Stimulus | Inhibitor | $IC_{50}$ (µg/mL) | % Remaining Phosphorylation at 15 µg/mL (100 nM) Inhibitor |
|---|---|---|---|
| IGF-2 (100 ng/mL) | 60833 | 0.82 | 6 |
|  | αIR3 | >15 | 115 |
|  | Control IgG | >15 | 109 |

EXAMPLE 3

Effects on IGF-1 and IGF-2-induced Cell Proliferation

The effects of antibodies 60814, 60819, and 60833 on IGF-1 and IGF-2 induced MCF-7 (breast cancer derived) and COLO 205 (colon cancer derived) cell line proliferation is determined Examples of the effects of antibodies 60814 and 60819 are shown in FIGS. 4A-D. All three antibodies show a dose dependent inhibition of IGF-1 (FIGS. 4A and 4C) and IGF-2 (FIGS. 4B and 4D) induced MCF-7 (FIGS. 4A and 4B) and COLO 205 (FIGS. 4C and 4D) cell proliferation. The concentration of each antibody required to inhibit 50% of the IGF-1 or IGF-2 induced proliferation of each cell line is shown in Table 5.

TABLE 5

INHIBITION OF IGF-1 AND IGF-2 INDUCED PROLIFERATION OF THE MCF-7 AND COLO 205 CANCER CELL LINES

| | | $IC_{50}$ (ng/ml) | | |
|---|---|---|---|---|
| Cell Line | Stimulation | 60814 | 60819 | 60833 |
| MCF7 | IGF-1 | 24.1 | 54.0 | 38.6 |
| MCF7 | IGF-2 | 78.2 | 40.8 | 81.2 |
| COLO-205 | IGF-1 | 135.0 | 216.9 | 165.1 |
| COLO 205 | IGF-2 | 576.1 | 100.8 | 632.3 |

EXAMPLE 4

Effects on Proliferation of Ewing's Sarcoma-derived Cell Lines

Figure 5:
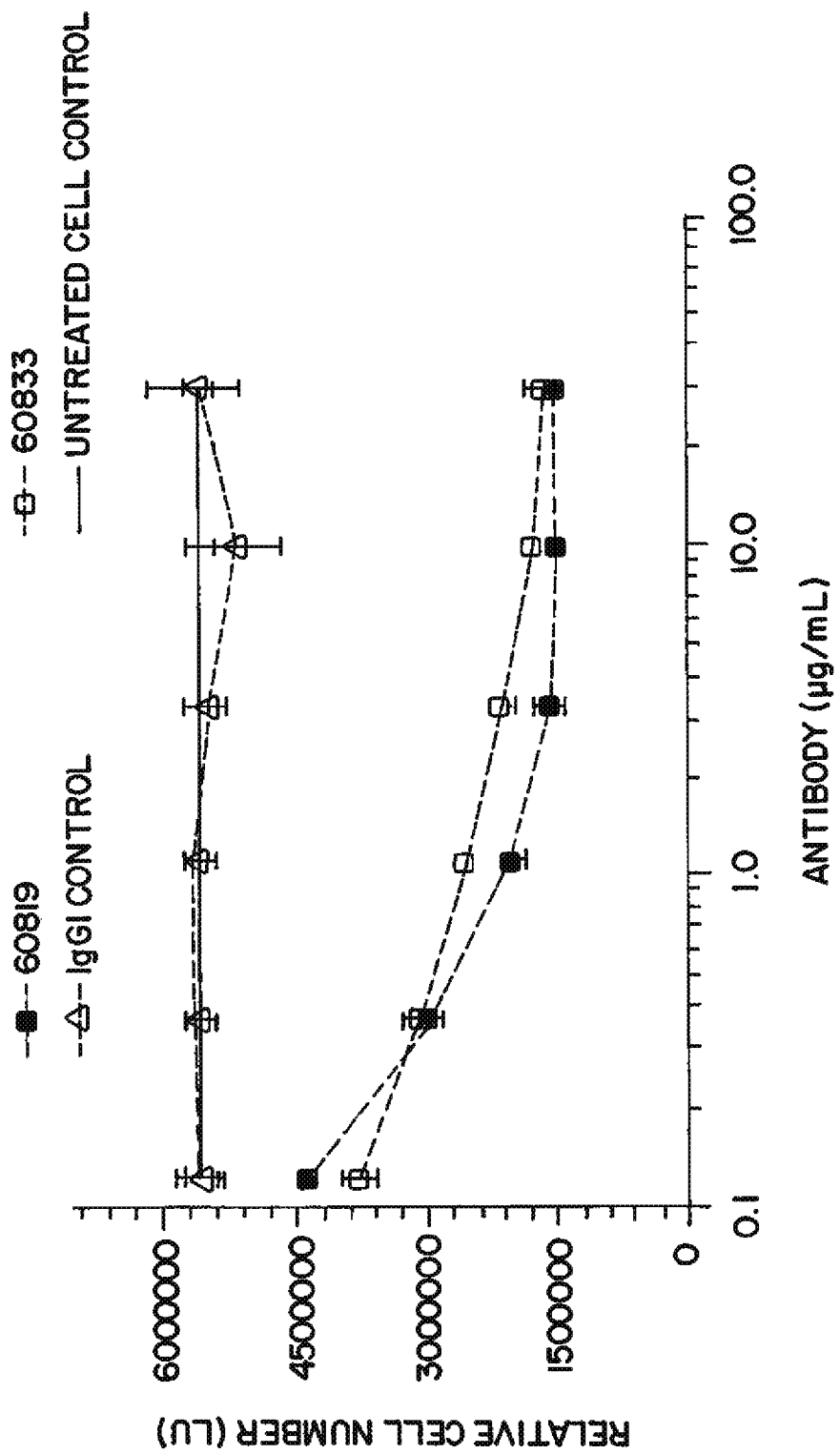
FIG. 5 shows the effect of antibodies 60819 and 60833 on the proliferation of the Ewing's sarcoma-derived cell line TC-71 in 10% growth medium.

The effect of antibodies 60819 and 60833 on the proliferation of the Ewing's sarcoma-derived cell line TC-71 grown in medium containing 10% FCS is shown in FIG. 5. Relative to a humanized IgG1 isotype control antibody, that does not bind IGF-1 or IGF-2, both 60819 and 60833 show a dose-dependent inhibition of TC-71 cell proliferation.

EXAMPLE 5

Effect on Total Murine and Rat IGF-1 Levels

Figure 6:
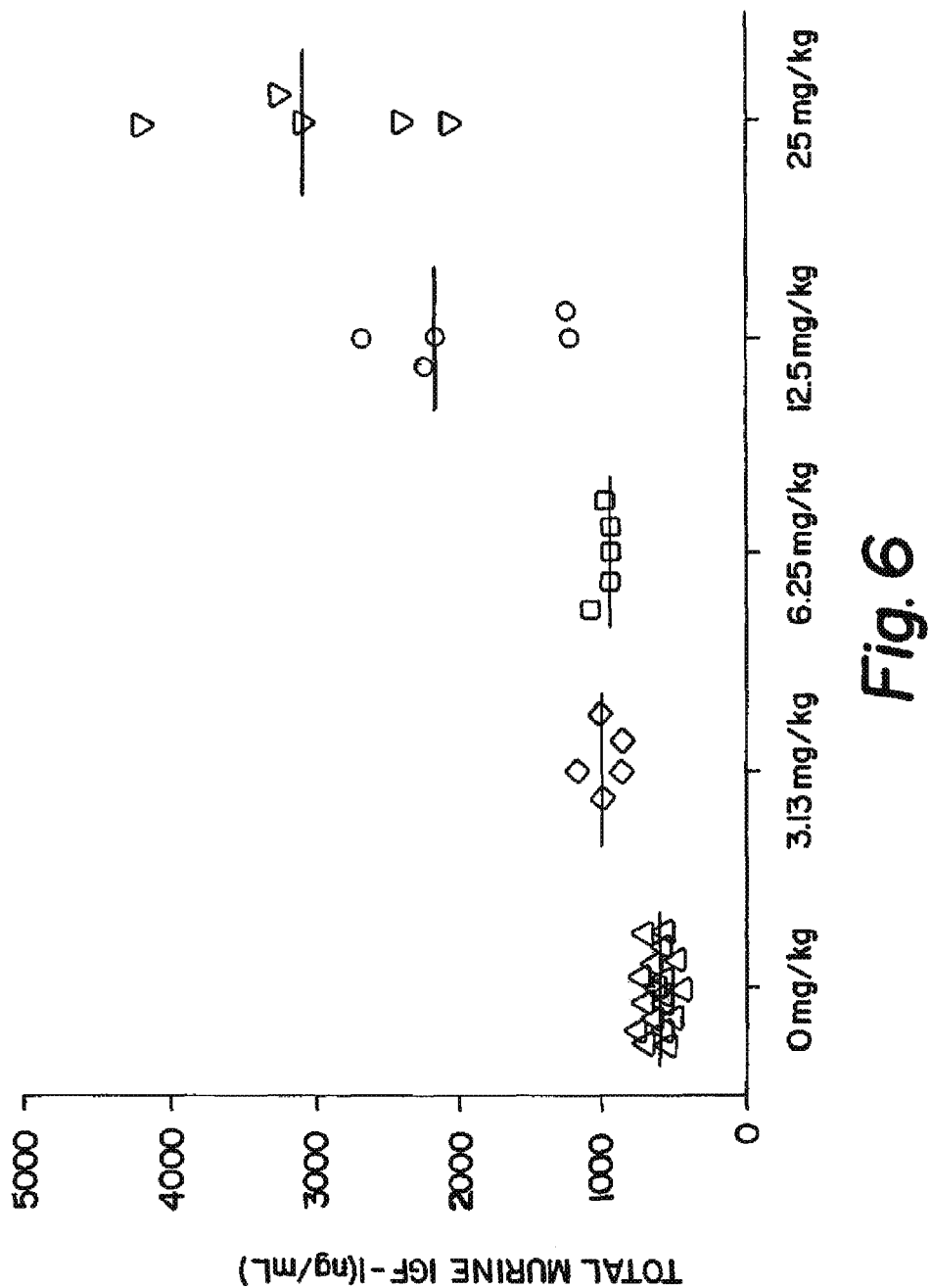
FIG. 6 shows the effect of antibody 60819 on murine total serum IGF-1 levels 24 hours following the administration of single doses of 25, 12.5, 6.25, 3.13 mg/kg. 0 mg/kg represents the total serum IGF-1 levels prior to antibody treatment.
Figure 7:
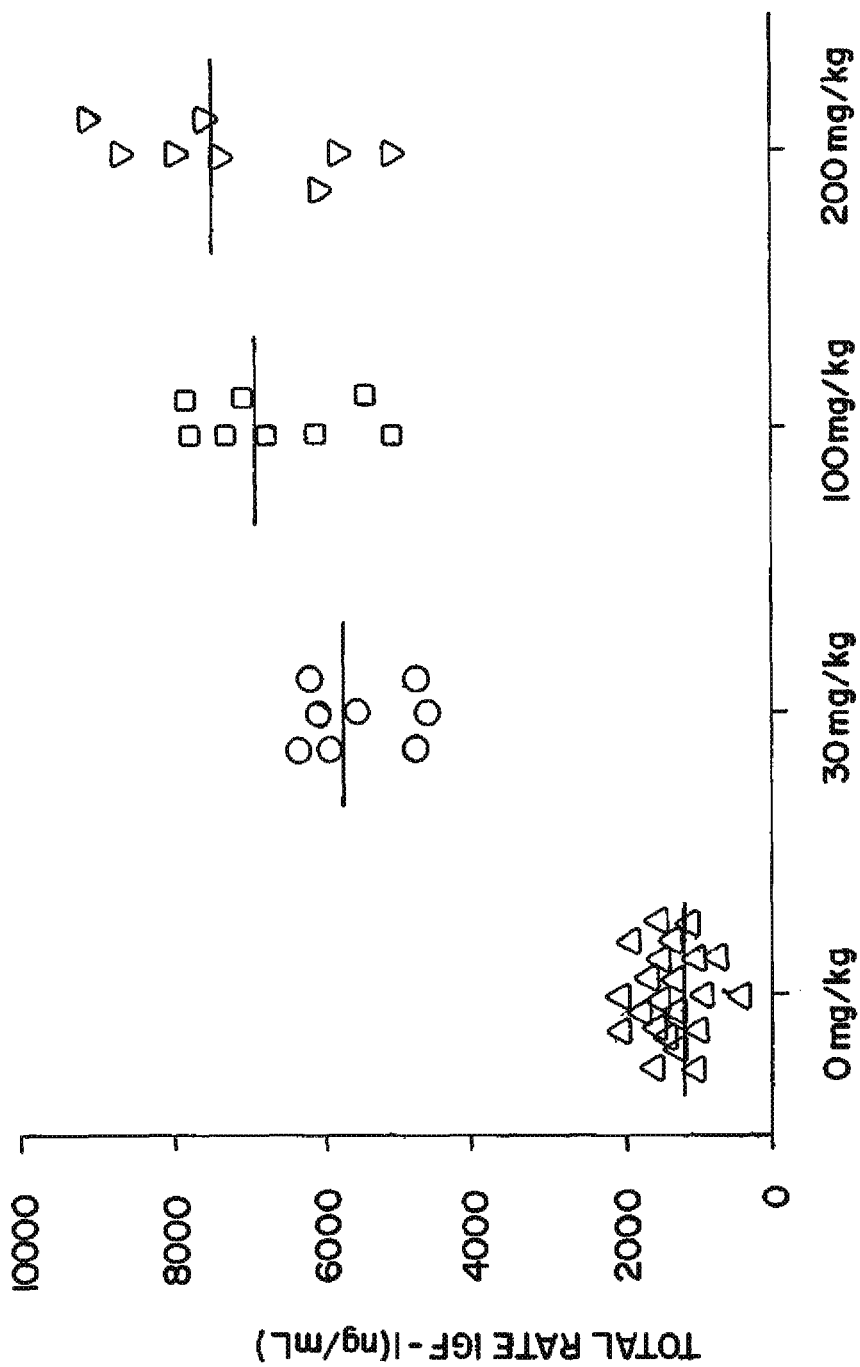
FIG. 7 shows the effect of antibody 60819 on rat total plasma IGF-1 levels 24 hours following the administration of single doses of 30, 100, 200 mg/kg by a 10 minute intravenous infusion. 0 mg/kg represents the total serum IGF-1 levels prior to antibody treatment.

Neutralization of active IGF-1 with an IGF targeted antibody may be expected to result in an endocrine feedback through the GH pathway which results in elevated total serum IGF-1 levels. Antibodies 60814, 60819, and 60833 are cross-reactive with mouse and rat IGF-1 which allows any pharmacodynamic effect on total serum IGF-1 levels to be measured in these species. As shown in FIGS. 6 and 7, administration of antibody 60819 to mice (FIG. 6) and rats (FIG. 7) results in a dose dependent elevation of serum total murine and rat IGF-1 levels 24 hours post administration. This represents a useful pharmacodynamic marker of the activity of these antibodies which can be tested during clinical development in humans.

EXAMPLE 6

Figure 8:
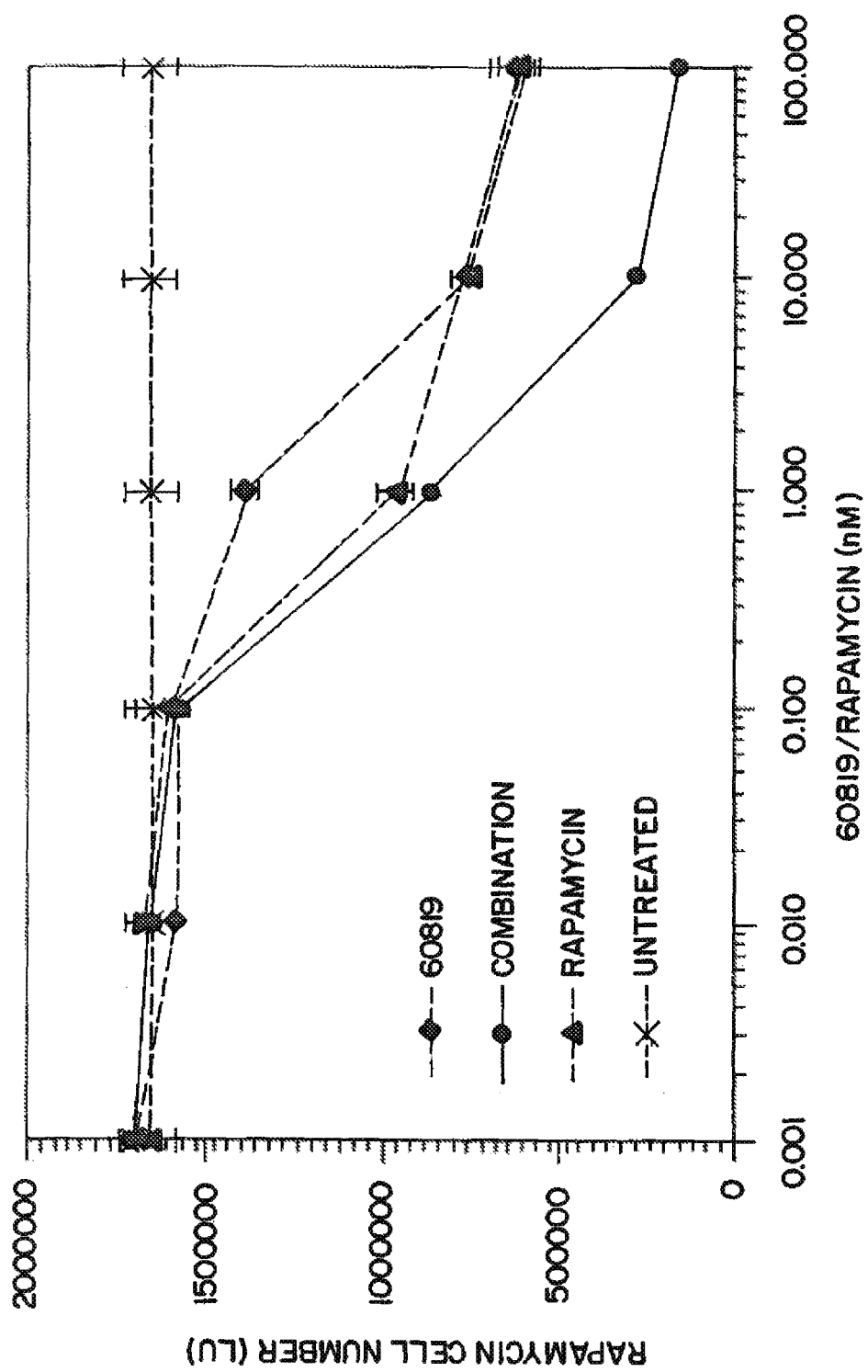
FIG. 8 demonstrates the effect of antibody 60819 and rapamycin, alone or in combination, on the proliferation of the Ewing's sarcoma-derived cell line SK-ES-1 in 10% FCS containing growth medium.

Effect of Combination of IGF Ligand Targeting Antibodies and Rapamycin on Ewing's Sarcoma-derived Cell Line Proliferation and Intracellular Signaling The effect of antibody 60819 and the mTOR inhibitor rapamycin, alone or in combination, on the proliferation of the Ewing's sarcoma-derived cell line SK-ES-1 is shown in FIG. 8. There is a dose dependent inhibition of proliferation with both antibody 60819 and rapamycin alone, with both single agents achieving around 60% proliferation inhibition at 100 nM. Combination of equivalent doses of both antibody 60819 and rapamycin demonstrated an additive effect on the inhibition of cell proliferation with approximately 95% inhibition when 100 nM doses are combined.

Figure 9:
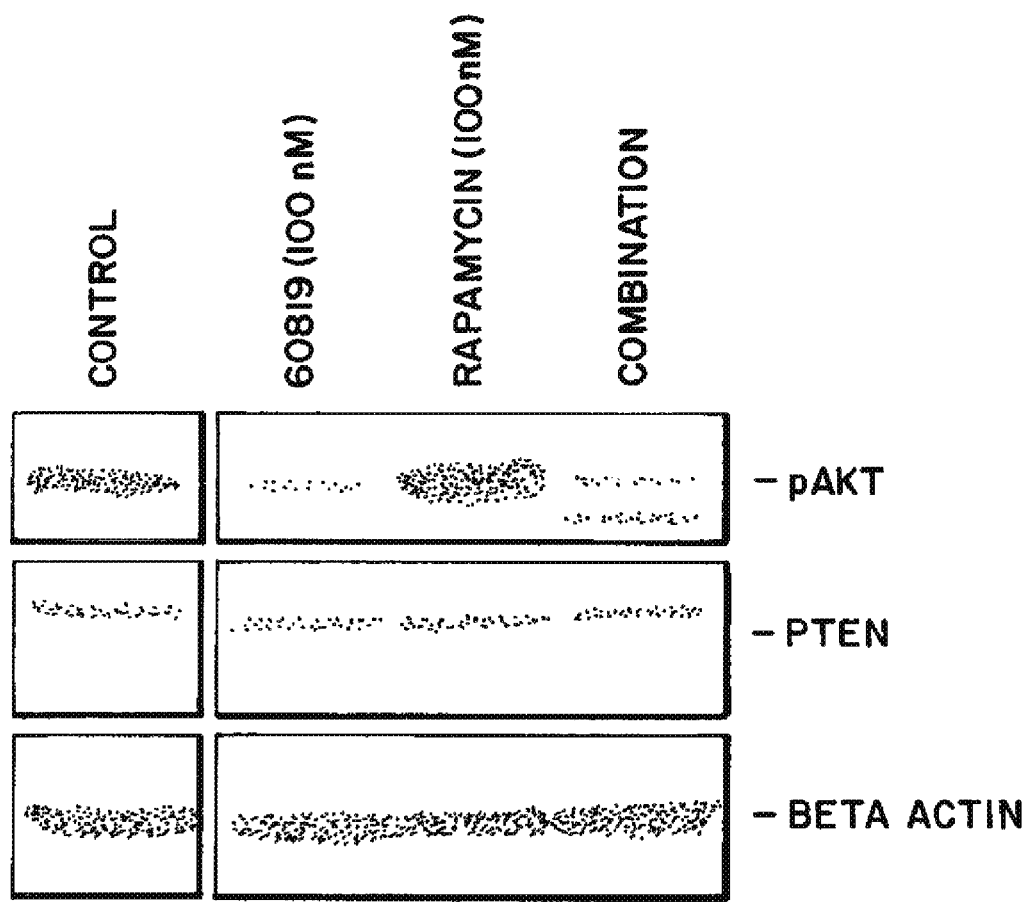
FIG. 9 shows the effect of antibody 60819 and rapamycin, alone or in combination, on the phosphorylation of AKT and levels of PTEN.

IGF-induced cell proliferation is mediated via a chain of intracellular protein phosphorylation events. One protein whose phosphorylation is increased by IGF stimulation is AKT. FIG. 9 demonstrates the effect of antibody 60819 and rapamycin, alone or in combination, on the phosphorylation of AKT in SK-ES-1 cells 24 hours following treatment using 100 nM doses. Compared with proliferating untreated cells which show phosphorylation of AKT, 100 nM antibody 60819 inhibited AKT phosphorylation. Conversely, 100 nM rapamycin treatment resulted in higher levels of phosphorylated AKT than the control which is thought to be due to a compensatory feedback mechanism following mTOR inhibition. However, when 100 nM rapamycin and 100 nM antibody 60819 are combined the phosphorylation of AKT is inhibited. This suggests that the compensatory feedback which leads to phosphorylated AKT upon rapamycin treatment is due to elevation of the IGF ligands and these are inhibited by antibody 60819. FIG. 9 also demonstrates that both antibody 60819 and rapamycin, alone or in combination, do not affect the total levels of PTEN.

EXAMPLE 7

Figure 10:
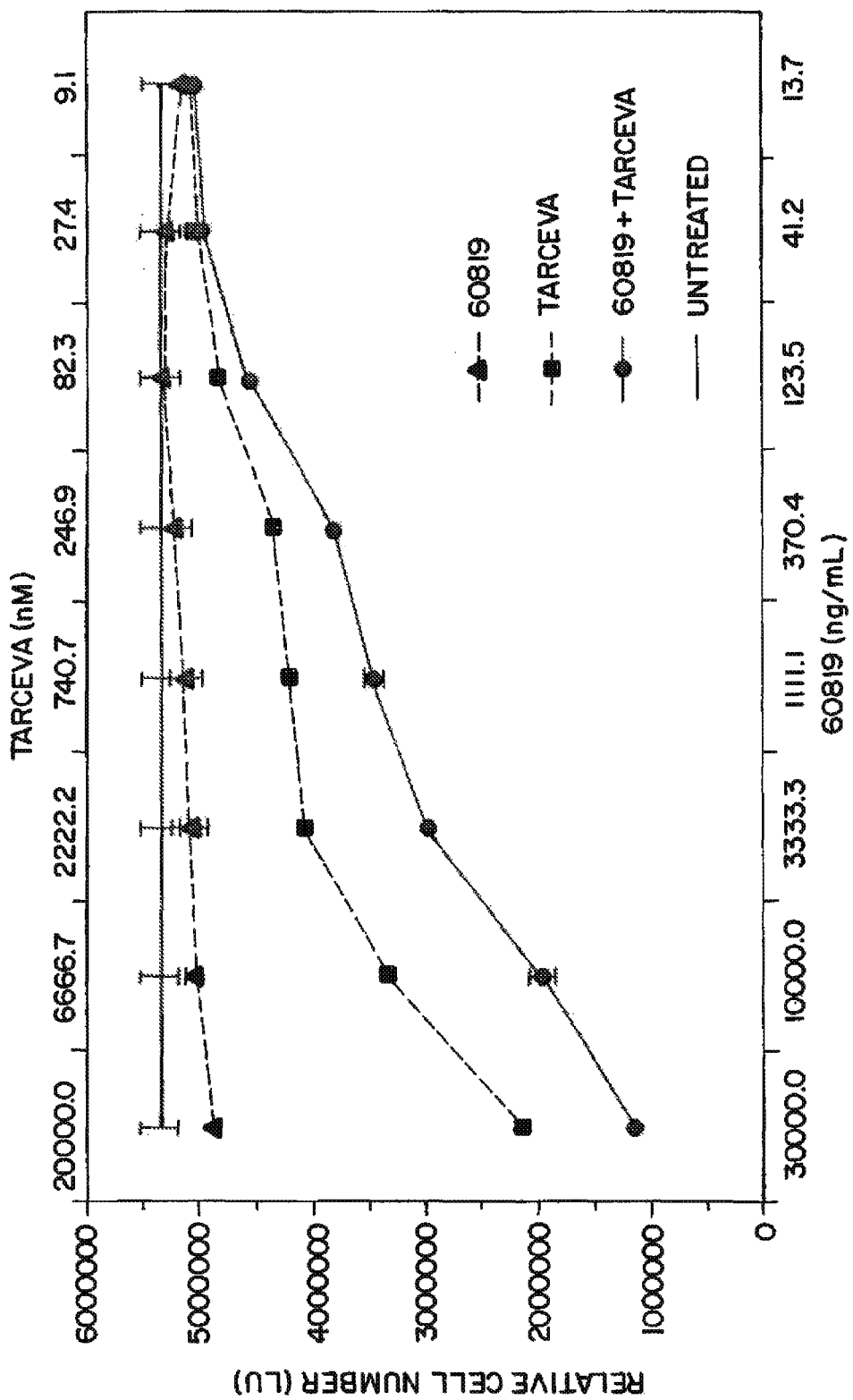
FIG. 10 demonstrates the effect of antibody 60819 and erlotinib/Tarceva, alone or in combination, on the proliferation of the NSCLC-derived cell line A-549 in 10% FCS containing growth medium.

Effect of Combination of an IGF Ligand Targeting Antibody and an EGFR Inhibitor on NSCLC-derived Cell Line Proliferation The effect of antibody 60819 and the EGFR inhibitor erlotinib/tarceva, alone or in combination, on the proliferation of the NSCLC-derived cell line A-549 is shown in FIG. 10. In this model, there is only a small effect of antibody 60819 alone on cell proliferation whilst tarceva shows a dose dependent effect with around 60% cell proliferation inhibition at the highest dose tested (20 µM). However, when antibody 60819 and tarceva are combined there is a more potent and effective inhibition of cell proliferation indicative of a synergistic effect.

EXAMPLE 8

Pharmacokinetic Properties in Wistar Rats

The mean pharmacokinetic parameters of antibody 60833 in Wistar rats on the first day of dosing with 18, 52, and 248 mg/kg is shown in Table 6. Terminal half-life was calculated after the last day of dosing (with t(n)=1008 hours), the average terminal half-life for all three dose levels is 221 hr (9.2 days).

TABLE 6

MEAN PHARMACOKINETIC PARAMETERS OF ANTIBODY 60833 IN WISTAR RATS ON FIRST DAY OF DOSING

| | 60833 Dose (mg/kg) | | |
|---|---|---|---|
| | 18 | 52 | 248 |
| C(max) [mg/mL] | 0.531 | 1.70 | 5.56 |
| AUC(0-72 h) [mg · h/mL] | 15.5 | 40.2 | 120 |
| CL [(mL/day)/kg] | 22.9 | 28.7 | 37.3 |
| V(ss) [mL/kg] | 68.1 | 76.3 | 65.4 |
| t½φ [hr] | 210 | 197 | 255 |

φ = after last day of dosing with t(n) = 1008 hr

Example 9

Fab-IGF-1 Co-Crystallisation and Structure Determination to Identify Antibody Binding Sites on IGF-1

Figure 11:
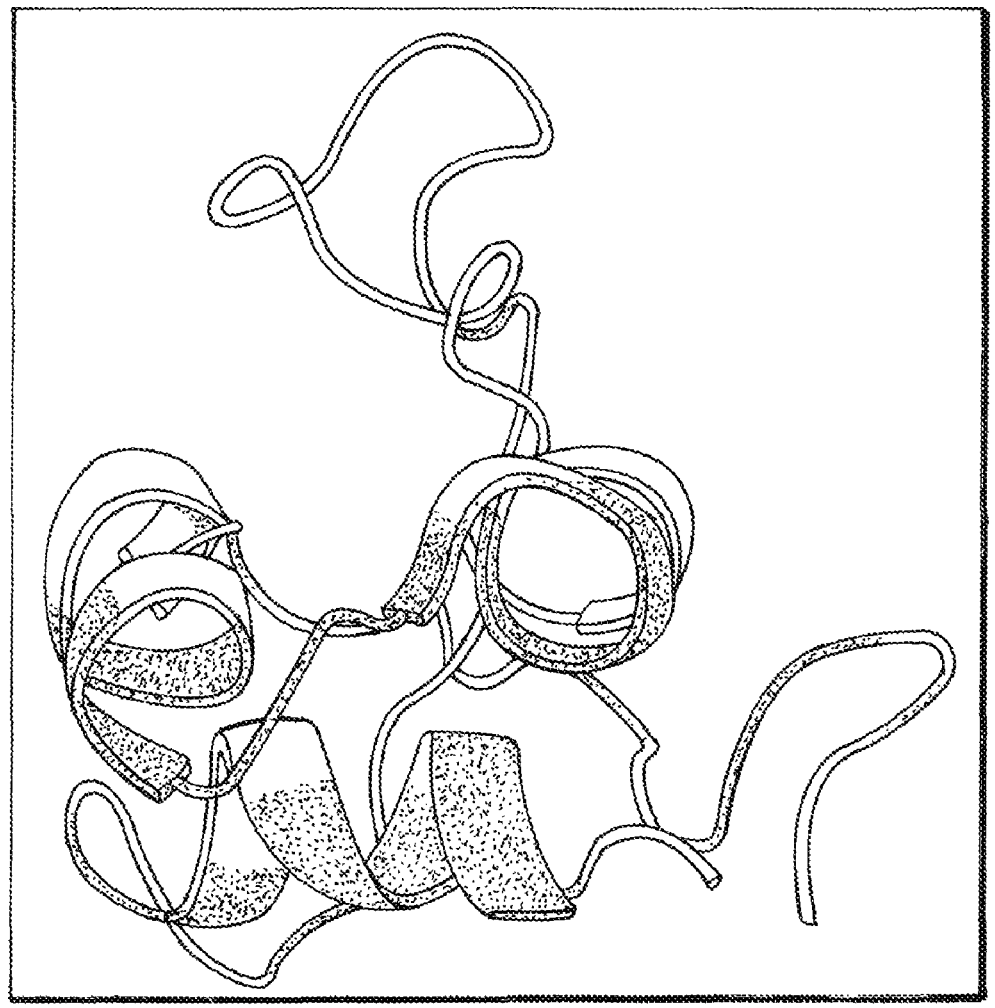
FIG. 11 shows the 3D structure of human IGF-1 where the amino acids bound by antibody 60833 are highlighted (dark grey). The linear amino acid sequence of human IGF-1 where the amino acids that interact with antibody 60833 are underlined is shown underneath (SEQ ID NO: 43).

To definitively determine the residues on human IGF-1 that interact with the IGF antibodies the Fab and IGF-1 were co-crystallised and the structure of the interaction determined with better than 2 Å resolution. The residues on IGF-1 that are contacted by antibody (Fab) 60833 are shown in Table 7. In total 19 residues on IGF-1 make contact with 15 CDR residues on 60833. Of these 19 IGF-1 residues 17 are identical in human IGF-2 when the human IGF-1 and IGF-2 amino acid sequences are aligned (listed in Table 7). FIG. 11 shows the 3D structure of IGF-1 with the amino acids that are bound by 60833 highlighted, the linear amino acid sequence of human IGF-1 is also shown with the interacting amino acids underlined.

TABLE 7

RESIDUES IN HUMAN IGF-1 THAT MAKE CONTACTS WITH RESIDUES OF 60833 FAB

| IGF-1 residues in contact with 60833 | Contact residues on 60833 (CDR) | Homologous residue on IGF-2 |
|---|---|---|
| Leu (L) 5 | Tyr (Y) 54; (HCDR 2) | Leu (L) 8 |
| Cys (C) 6 | Ser (S) 56; (HCDR 2) | Cys (C) 9 |
| Glu (E) 9 | Thr (T) 52; (HCDR 2) | Glu (E) 12 |
| | Ser (S) 53; (HCDR 2) | |
| | Tyr (Y) 54; (HCDR 2) | |
| | Gly (G) 55; (HCDR 2) | |
| | Ser (S) 56; (HCDR 2) | |
| Leu (L) 10 | Phe (F) 57; (HCDR 2) | Leu (L) 13 |
| Asp (D) 12 | Trp (W) 33; (HCDR 1) | Asp (D) 15 |
| Ala (A) 13 | Trp (W) 33; (HCDR 1) | — |
| Phe (F) 16 | Trp (W) 33; (HCDR 1) | Phe (F) 19 |
| | Arg (R) 92; (LCDR 3) | |
| | Tyr (Y) 98; (LCDR 3) | |
| | Trp (W) 99; (LCDR 3) | |
| | Tyr (Y) 101; (HCDR 3) | |
| Val (V) 17 | Arg (R) 92; (LCDR 3) | Val (V) 20 |
| | Tyr (Y) 98; (LCDR 3) | |
| Arg (R) 21 | Tyr (Y) 95; (LCDR 3) | Arg (R) 24 |
| Cys (C) 47 | Ser (S) 56; (HCDR 2) | Cys (C) 46 |
| | Phe (F) 57; (HCDR 2) | |
| Cys (C) 48 | Ser (S) 56; (HCDR 2) | Cys (C) 47 |
| Phe (F) 49 | Tyr (Y) 54; (HCDR 2) | Phe (F) 48 |
| | Gly (G) 55; (HCDR 2) | |
| | Ser (S) 56; (HCDR 2) | |
| Ser (S) 51 | Gly (G) 55; (HCDR 2) | Ser (S) 50 |
| | Ser (S) 56; (HCDR 2) | |
| | Thr (T) 58; (HCDR 2) | |
| Cys (C) 52 | Ser (S) 56; (HCDR 2) | Cys (C) 51 |
| | Phe (F) 57; (HCDR 2) | |
| | Thr (T) 58; (HCDR 2) | |
| Asp (D) 53 | Phe (F) 57; (HCDR 2) | Asp (D) 52 |
| | Thr (T) 58; (HCDR 2) | |
| Leu (L) 54 | Trp (W) 33; (HCDR 1) | Leu (L) 53 |
| | Phe (F) 57; (HCDR 2) | |
| | Thr (T) 58; (HCDR 2) | |
| | Tyr (Y) 98; (LCDR 3) | |
| Arg (R) 55 | Lys (K) 65; (HCDR 2) | — |
| | Gly (G) 96; (LCDR 3) | |
| | Tyr (Y) 98; (LCDR 3) | |
| Leu (L) 57 | Phe (F) 57; (HCDR 2) | Leu (L) 56 |
| Glu (E) 58 | Tyr (Y) 95; (LCDR 3) | Glu (E) 57 |
| | Gly (G) 96; (LCDR 3) | |
| | Tyr (Y) 98; (LCDR 3) | |
| 19 residues on IGF-1_involved in contact with 60833 | 15 residues on 60833 involved in contacts with IGF-1: HCDR 1: 1 residues HCDR 2: 8 residues HCDR 3: 1 residues LCDR 1: — LCDR 2: — LCDR 3: 5 residues | |

REFERENCES

Barbas, et al., 1994, Proc. Nat. Acad. Sci, USA 91:3809-3813.
Burtrum et al., Cancer Res. 63: 8912-21, 2003).
Chen et al., J. Clin. Endocrinol. 90: 366-371, 2005.
Cui et al., Science 299: 1753-55, 2003.
Cruz-Correa et al., Gastroenterology 126: 1190-3, 2004.
Dufner and Thomas, Exp. Cell Res. 253: 100-109, 1999.
Frasca et al., Mol. Cell. Biol. 19: 3278-88, 1999.
Freier et al., Gut, May;44(5): 704-08, 1999;
Fukuzawa et al., Int. J. Cancer 82: 490-497, 1999.
Goetsch et al., Int. J. Cancer 113: 316-28, 2005.
Goya et al., Cancer Res. 64: 6252-58, 2004.
Haenel et al., Anal. Biochem. 339: 182-184, 2005.
Hassan et al., Cancer Res. 60: 1070-6, 2000
Hawkins et al., 1992, J. MoI. Biol. 226(3): 889 896.
Jackson et al., 1995, J. Immunol. 154(7):3310-9.
Jerome et al., End. Rel. Cancer 10: 561-578, 2003.
Kabat et al., Sequences of Proteins of Immunological Interest (5th Ed.). NIH Publication No. 91 3242. U.S. Department of Health and Human Services, Public Health Service, National Institutes of Health, Bethesda, Md. (1991).
Kipriyanow and Le Gall, Molecular Biotechnology 26: 39-60, 2004.
Knappik et al., J. Mol. Biol. 296: 57-86, 2000.
Kolb et al. Pediatr. Blood Cancer 50: 1190-1197, 2008.
Krebs, B. et al., J. Immunol. Meth. 245: 67 84, 2001.
Kulik et al., Mol. Cell. Biol. 17: 1595-606, 1997.
LeRoith D, Experimental Diab. Res. 4: 205-212, 2003.
Li et al., Tumour Biol. 25: 62-8, 2004.
Lowman et al., Biochemistry 30(45): 10832-10837, 1991.
Lund et al., Cancer Lett. 206: 85-96, 2004.
Manara et al., Clin. Cancer Res. 13: 1322-1330, 2007.
Manes et al., Endocrinology 138: 905-915, 1997.
Marks et al., 1992, Biotechnology 10:779-783.
Miyamoto et al., Clin. Cancer Res. 11: 3494-3502, 2005.
Moorhead et al., Oncogene 22: 853-7, 2003.
Nagy et al., Nature Med. 8(8): 801-807, 2002.
Ng et al., J. Gastroenterol. Hepatol. 13: 152-7, 1998.
Pandini et al., J. Biol. Chem. 277: 39684-95, 2002.
Pollack et al., Nature Rev. Can. 4: 505-518, 2004.
Pollack et al., American Society for Clinical Oncology (ASCO), Annual Meeting 2007, abstract 3587.
Quinn et al., J. Biol. Chem. 271: 11477-83, 1996.
Rauchenberger, R. et al., J. Biol. Chem. 278: 38194-38205, 2003.
Reinberg, U.S. News World Report, Mar. 5, 2008.
Remington: "The Science and Practice of Pharmacy", 2005, 21$^{st}$ edition, Hendrickson Randy, Editor; Advanced Concepts Institute, University of The Sciences in Philadelphia, 600 S. 43$^{rd}$ Street, Philadelphia, Pa. 19104, USA; 215-895-1184.
Renehan et al., Br. J. Cancer 83: 1344-50, 2000a).
Renehan et al., J. Clin. Endocrinol. Metab. 85: 3402-8, 2000b).
Revets et al., Expert Opin Biol Ther. 5(1):111-24, 2005.
Rubin et al., Lab. Invest. 73: 311-31, 1995.
Russell et al., Proc. Natl. Acad. Sci USA 81: 2389-2392, 1984.
Scotlandi et al., Cancer Res. 56: 4570-4574, 1996.
Sell et al., Natl. Acad. Sci. USA 90: 11217-21, 1993.
Sell et al., Mol. Cell. Biol. 14: 3604-12, 1994.
Shier et al., 1995, Gene 169:147-155.
Shukla et al., 2007, J. Chromatography B, 848(1): 28-39
Srinivasan, M. and Roeske, R W., Curr Protein Pept Sci. 2005, April;6(2):185-96.
Strumberg D., 2005, Drugs Today (Barc). 2005 Dec;41(12): 773-84
Takanami et al., J. Surg. Oncol. 61: 205-8, 1996.
Tsai et al., Scand. J. Gastroenterol. 40: 68-75, 2005.
Wang et al., World J. Gastroenterol. 9: 267-70, 2003.
Woodson et al., J. Natl. Cancer Inst. 96: 407-10, 2004.
Yao et al., Clin. Cancer Res. 9: 2719-26, 2003a).
Yao et al., J. Clin. Invest. 111: 265-273, 2003b).
Yelton et al., 1995, Immunol. 155:1994-2004.

Zapata et al., Protein Eng. 8(10): 1057-1062., 1995.
Zhao et al., Cancer Epidemiol. Biomarkers Prev. 14: 1819-22, 2005.
WO 89/011297
WO 94/29348
WO 02/056910
WO 03/002609
WO 03/050531
WO 03/093317
WO 04/003019
WO 04/058821
WO 2005/018671
WO 2005/027970
WO 2005/028515
WO 2007/042309
WO 2007/070432
JP 2003-310275
U.S. Pat. No. 4,342,566
U.S. Pat. No. 3,773,919
U.S. Pat. No. 6,696,245
U.S. Pat. No. 6,991,790
U.S. Pat. No. 7,060,268

The invention claimed is:

1. An anti-IGF antibody molecule, wherein said antibody molecule has heavy chain CDRs comprising the amino acid sequences of SEQ ID NO:21 (CDR1), SEQ ID NO:22 (CDR2) and SEQ ID NO:23 (CDR3) and has light chain CDRs comprising the amino acid sequences of SEQ ID NO:24 (CDR1), SEQ ID NO:25 (CDR2) and SEQ ID NO:26 (CDR3).

2. The antibody molecule of claim 1, which has a variable heavy chain comprising the amino acid sequence of SEQ ID NO:28.

3. The antibody molecule of claim 1, which has a variable light chain comprising the amino acid sequence of SEQ ID NO:30.

4. The antibody molecule of claim 1, comprising a heavy chain constant region selected from the group consisting of IgG1, IgG2, IgG3, IgG4, IgM, IgA and IgE constant regions.

5. The antibody molecule of claim 4, wherein said heavy chain constant region is IgG1 comprising the amino acid sequence of SEQ ID NO:32.

6. The antibody molecule of claim 1, wherein the light chain constant region is Igλ.

7. The antibody molecule of claim 6, wherein the light chain constant region comprises the amino acid sequence of SEQ ID NO:34.

8. The antibody molecule of claim 1, which is a Fab, F(ab')$_2$, or single chain Fv fragment.

9. A pharmaceutical composition comprising an antibody molecule of claim 1 and a pharmaceutically acceptable carrier.

10. The antibody molecule of claim 1, which has a variable heavy chain comprising the amino acid sequence of SEQ ID NO:28 and a variable light chain comprising the amino acid sequence of SEQ ID NO:30.

11. A pharmaceutical composition comprising an antibody molecule of claim 10 and a pharmaceutically acceptable carrier.

12. An anti-IGF antibody molecule, wherein said antibody molecule has
 a) a heavy chain comprising the amino acid sequence of SEQ ID NO:39, and
 b) a light chain comprising the amino acid sequence of SEQ ID NO:40.

13. A pharmaceutical composition comprising an antibody molecule of claim 12 and a pharmaceutically acceptable carrier.

* * * * *

SEQUENCE LISTING

```
<160> NUMBER OF SEQ ID NOS: 43

<210> SEQ ID NO 1
<211> LENGTH: 5
<212> TYPE: PRT
<213> ORGANISM: Homo sapiens

<400> SEQUENCE: 1

Asn Tyr Trp Met His
1               5

<210> SEQ ID NO 2
<211> LENGTH: 17
<212> TYPE: PRT
<213> ORGANISM: Homo sapiens

<400> SEQUENCE: 2

Gly Ile Ser Gly Trp Ser Ser Trp Thr Tyr Tyr Ala Asp Ser Val Lys
1               5                   10                  15

Gly

<210> SEQ ID NO 3
<211> LENGTH: 13
<212> TYPE: PRT
<213> ORGANISM: Homo sapiens

<400> SEQUENCE: 3

Phe Gly Ile Asp Ala Tyr Thr Lys Val Tyr Phe Asp Tyr
1               5                   10

<210> SEQ ID NO 4
<211> LENGTH: 11
<212> TYPE: PRT
<213> ORGANISM: Homo sapiens

<400> SEQUENCE: 4

Ser Gly Asp Asn Ile Pro Leu Lys Tyr Val Ser
1               5                   10

<210> SEQ ID NO 5
<211> LENGTH: 7
<212> TYPE: PRT
<213> ORGANISM: Homo sapiens

<400> SEQUENCE: 5

Asp Asp Asn Lys Arg Pro Ser
1               5

<210> SEQ ID NO 6
<211> LENGTH: 11
<212> TYPE: PRT
```

<213> ORGANISM: Homo sapiens

<400> SEQUENCE: 6

Ser Ser Trp Asp Thr Leu Asp Ile Phe Asn Val
1               5                   10

<210> SEQ ID NO 7
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 7

```
cag gtg gaa ttg gtg gaa agc ggc ggc ggc ctg gtg caa ccg ggc ggc      48
Gln Val Glu Leu Val Glu Ser Gly Gly Gly Leu Val Gln Pro Gly Gly
1               5                   10                  15 agc ctg cgt ctg agc tgc gcg gcc tcc gga ttt acc ttt tct aat tat      96
Ser Leu Arg Leu Ser Cys Ala Ala Ser Gly Phe Thr Phe Ser Asn Tyr
            20                  25                  30 tgg atg cat tgg gtg cgc caa gcc cct ggg aag ggt ctc gag tgg gtg     144
Trp Met His Trp Val Arg Gln Ala Pro Gly Lys Gly Leu Glu Trp Val
        35                  40                  45 agc ggt atc tct ggt tgg tct agc tgg acc tat tat gcg gat agc gtg     192
Ser Gly Ile Ser Gly Trp Ser Ser Trp Thr Tyr Tyr Ala Asp Ser Val
    50                  55                  60 aaa ggc cgt ttt acc att tca cgt gat aat tcg aaa aac acc ctg tat     240
Lys Gly Arg Phe Thr Ile Ser Arg Asp Asn Ser Lys Asn Thr Leu Tyr
65                  70                  75                  80 ctg caa atg aac agc ctg cgt gcg gaa gat acg gcc gtg tat tat tgc     288
Leu Gln Met Asn Ser Leu Arg Ala Glu Asp Thr Ala Val Tyr Tyr Cys
                85                  90                  95 gcg cgt ttt ggt att gat gct tat act aag gtt tat ttt gat tat tgg     336
Ala Arg Phe Gly Ile Asp Ala Tyr Thr Lys Val Tyr Phe Asp Tyr Trp
            100                 105                 110 ggc caa ggc acc ctg gtg acg gtt agc tca                              366
Gly Gln Gly Thr Leu Val Thr Val Ser Ser
        115                 120
```

<210> SEQ ID NO 8
<211> LENGTH: 122
<212> TYPE: PRT
<213> ORGANISM: Homo sapiens

<400> SEQUENCE: 8

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser
        115                 120

<210> SEQ ID NO 9
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 9

```
gat atc gaa ctg acc cag ccg cct tca gtg agc gtt gca cca ggt cag      48
Asp Ile Glu Leu Thr Gln Pro Pro Ser Val Ser Val Ala Pro Gly Gln
1               5                   10                  15 acc gcg cgt atc tcg tgt agc ggc gat aat att cct ctt aag tat gtt      96
Thr Ala Arg Ile Ser Cys Ser Gly Asp Asn Ile Pro Leu Lys Tyr Val
            20                  25                  30 tct tgg tac cag cag aaa ccc ggg cag gcg cca gtt ctt gtg att cat     144
Ser Trp Tyr Gln Gln Lys Pro Gly Gln Ala Pro Val Leu Val Ile His
        35                  40                  45 gat gat aat aag cgt ccc tca ggc atc ccg gaa cgc ttt agc gga tcc     192
Asp Asp Asn Lys Arg Pro Ser Gly Ile Pro Glu Arg Phe Ser Gly Ser
    50                  55                  60 aac agc ggc aac acc gcg acc ctg acc att agc ggc act cag gcg gaa     240
Asn Ser Gly Asn Thr Ala Thr Leu Thr Ile Ser Gly Thr Gln Ala Glu
65                  70                  75                  80 gac gaa gcg gat tat tat tgc tct tct tgg gat act ctt gat att ttt     288
Asp Glu Ala Asp Tyr Tyr Cys Ser Ser Trp Asp Thr Leu Asp Ile Phe
                85                  90                  95 aat gtg ttt ggc ggc ggc acg aag tta acc gtc cta ggt                 327
Asn Val Phe Gly Gly Gly Thr Lys Leu Thr Val Leu Gly
            100                 105
```

<210> SEQ ID NO 10
<211> LENGTH: 109
<212> TYPE: PRT
<213> ORGANISM: Homo sapiens

<400> SEQUENCE: 10

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Thr Leu Asp Ile Phe
                85                  90                  95

Asn Val Phe Gly Gly Gly Thr Lys Leu Thr Val Leu Gly
            100                 105
```

<210> SEQ ID NO 11
<211> LENGTH: 5
<212> TYPE: PRT
<213> ORGANISM: Homo sapiens

<400> SEQUENCE: 11

```
Asn Tyr Trp Met His
1               5
```

```
<210> SEQ ID NO 12
<211> LENGTH: 17
<212> TYPE: PRT
<213> ORGANISM: Homo sapiens

<400> SEQUENCE: 12

Gly Ile Ser Gly Trp Ser Ser Trp Thr Tyr Tyr Ala Asp Ser Val Lys
1               5                   10                  15

Gly

<210> SEQ ID NO 13
<211> LENGTH: 13
<212> TYPE: PRT
<213> ORGANISM: Homo sapiens

<400> SEQUENCE: 13

Phe Gly Ile Asp Ala Tyr Thr Lys Val Tyr Phe Asp Tyr
1               5                   10

<210> SEQ ID NO 14
<211> LENGTH: 11
<212> TYPE: PRT
<213> ORGANISM: Homo sapiens

<400> SEQUENCE: 14

Ser Gly Asp Asn Ile Pro Leu Lys Tyr Val Ser
1               5                   10

<210> SEQ ID NO 15
<211> LENGTH: 7
<212> TYPE: PRT
<213> ORGANISM: Homo sapiens

<400> SEQUENCE: 15

Asp Asp Asn Lys Arg Pro Ser
1               5

<210> SEQ ID NO 16
<211> LENGTH: 11
<212> TYPE: PRT
<213> ORGANISM: Homo sapiens

<400> SEQUENCE: 16

Gln Ser Tyr Asp Tyr Phe Pro Lys Phe Val Val
1               5                   10

<210> SEQ ID NO 17
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 17 cag gtg gaa ttg gtg gaa agc ggc ggc ggc ctg gtg caa ccg ggc ggc       48
Gln Val Glu Leu Val Glu Ser Gly Gly Gly Leu Val Gln Pro Gly Gly
1               5                   10                  15 agc ctg cgt ctg agc tgc gcg gcc tcc gga ttt acc ttt tct aat tat       96
Ser Leu Arg Leu Ser Cys Ala Ala Ser Gly Phe Thr Phe Ser Asn Tyr
            20                  25                  30 tgg atg cat tgg gtg cgc caa gcc cct ggg aag ggt ctc gag tgg gtg      144
Trp Met His Trp Val Arg Gln Ala Pro Gly Lys Gly Leu Glu Trp Val
        35                  40                  45
```

```
agc ggt atc tct ggt tgg tct agc tgg acc tat tat gcg gat agc gtg      192
Ser Gly Ile Ser Gly Trp Ser Ser Trp Thr Tyr Tyr Ala Asp Ser Val
        50                  55                  60 aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
65                  70                  75                  80 ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                85                  90                  95 gcg cgt ttt ggt att gat gct tat act aag gtt tat ttt gat tat tgg      336
Ala Arg Phe Gly Ile Asp Ala Tyr Thr Lys Val Tyr Phe Asp Tyr Trp
            100                 105                 110 ggc caa ggc acc ctg gtg acg gtt agc tca                              366
Gly Gln Gly Thr Leu Val Thr Val Ser Ser
        115                 120
```

<210> SEQ ID NO 18
<211> LENGTH: 122
<212> TYPE: PRT
<213> ORGANISM: Homo sapiens

<400> SEQUENCE: 18

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser
        115                 120
```

<210> SEQ ID NO 19
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 19

```
gat atc gaa ctg acc cag ccg cct tca gtg agc gtt gca cca ggt cag       48
Asp Ile Glu Leu Thr Gln Pro Pro Ser Val Ser Val Ala Pro Gly Gln
1               5                   10                  15 acc gcg cgt atc tcg tgt agc ggc gat aat att cct ctt aag tat gtt       96
Thr Ala Arg Ile Ser Cys Ser Gly Asp Asn Ile Pro Leu Lys Tyr Val
            20                  25                  30 tct tgg tac cag cag aaa ccc ggg cag gcg cca gtt ctt gtg att cat      144
Ser Trp Tyr Gln Gln Lys Pro Gly Gln Ala Pro Val Leu Val Ile His
        35                  40                  45 gat gat aat aag cgt ccc tca ggc atc ccg gaa cgc ttt agc gga tcc      192
Asp Asp Asn Lys Arg Pro Ser Gly Ile Pro Glu Arg Phe Ser Gly Ser
    50                  55                  60
```

```
aac agc ggc aac acc gcg acc ctg acc att agc ggc act cag gcg gaa    240
Asn Ser Gly Asn Thr Ala Thr Leu Thr Ile Ser Gly Thr Gln Ala Glu
 65                  70                  75                  80 gac gaa gcg gat tat tat tgc cag tct tat gat tat ttt cct aag ttt    288
Asp Glu Ala Asp Tyr Tyr Cys Gln Ser Tyr Asp Tyr Phe Pro Lys Phe
                 85                  90                  95 gtt gtg ttt ggc ggc ggc acg aag tta acc gtc cta ggt                327
Val Val Phe Gly Gly Gly Thr Lys Leu Thr Val Leu Gly
            100                 105
```

<210> SEQ ID NO 20
<211> LENGTH: 109
<212> TYPE: PRT
<213> ORGANISM: Homo sapiens

<400> SEQUENCE: 20

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Tyr Phe Pro Lys Phe
                 85                  90                  95

Val Val Phe Gly Gly Gly Thr Lys Leu Thr Val Leu Gly
            100                 105
```

<210> SEQ ID NO 21
<211> LENGTH: 5
<212> TYPE: PRT
<213> ORGANISM: Homo sapiens

<400> SEQUENCE: 21

```
Ser Tyr Trp Met Ser
 1               5
```

<210> SEQ ID NO 22
<211> LENGTH: 17
<212> TYPE: PRT
<213> ORGANISM: Homo sapiens

<400> SEQUENCE: 22

```
Ser Ile Thr Ser Tyr Gly Ser Phe Thr Tyr Tyr Ala Asp Ser Val Lys
 1               5                  10                  15

Gly
```

<210> SEQ ID NO 23
<211> LENGTH: 8
<212> TYPE: PRT
<213> ORGANISM: Homo sapiens

<400> SEQUENCE: 23

```
Asn Met Tyr Thr His Phe Asp Ser
 1               5
```

<210> SEQ ID NO 24
<211> LENGTH: 13
<212> TYPE: PRT

<213> ORGANISM: Homo sapiens

<400> SEQUENCE: 24

Ser Gly Ser Ser Ser Asn Ile Gly Ser Asn Ser Val Ser
1               5                   10

<210> SEQ ID NO 25
<211> LENGTH: 7
<212> TYPE: PRT
<213> ORGANISM: Homo sapiens

<400> SEQUENCE: 25

Asp Asn Ser Lys Arg Pro Ser
1               5

<210> SEQ ID NO 26
<211> LENGTH: 11
<212> TYPE: PRT
<213> ORGANISM: Homo sapiens

<400> SEQUENCE: 26

Gln Ser Arg Asp Thr Tyr Gly Tyr Tyr Trp Val
1               5                   10

<210> SEQ ID NO 27
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 27 cag gtg gaa ttg gtg gaa agc ggc ggc ggc ctg gtg caa ccg ggc ggc        48
Gln Val Glu Leu Val Glu Ser Gly Gly Gly Leu Val Gln Pro Gly Gly
1               5                   10                  15 agc ctg cgt ctg agc tgc gcg gcc tcc gga ttt acc ttt act tct tat        96
Ser Leu Arg Leu Ser Cys Ala Ala Ser Gly Phe Thr Phe Thr Ser Tyr
            20                  25                  30 tgg atg tct tgg gtg cgc caa gcc cct ggg aag ggt ctc gag ctt gtg       144
Trp Met Ser Trp Val Arg Gln Ala Pro Gly Lys Gly Leu Glu Leu Val
        35                  40                  45 agc tct atc act tct tat ggt agc ttt acc tat tat gcg gat agc gtg       192
Ser Ser Ile Thr Ser Tyr Gly Ser Phe Thr Tyr Tyr Ala Asp Ser Val
    50                  55                  60 aaa ggc cgt ttt acc att tca cgt gat aat tcg aaa aac acc ctg tat       240
Lys Gly Arg Phe Thr Ile Ser Arg Asp Asn Ser Lys Asn Thr Leu Tyr
65                  70                  75                  80 ctg caa atg aac agc ctg cgt gcg gaa gat acg gcc gtg tat tat tgc       288
Leu Gln Met Asn Ser Leu Arg Ala Glu Asp Thr Ala Val Tyr Tyr Cys
                85                  90                  95 gcg cgt aat atg tat act cat ttt gat tct tgg ggc caa ggc acc ctg       336
Ala Arg Asn Met Tyr Thr His Phe Asp Ser Trp Gly Gln Gly Thr Leu
            100                 105                 110 gtg acg gtt agc tca                                                    351
Val Thr Val Ser Ser
        115

<210> SEQ ID NO 28
<211> LENGTH: 117
<212> TYPE: PRT
<213> ORGANISM: Homo sapiens

<400> SEQUENCE: 28

```
Gln Val Glu Leu Val Glu Ser Gly Gly Gly Leu Val Gln Pro Gly
1               5                   10                  15

Ser Leu Arg Leu Ser Cys Ala Ala Ser Gly Phe Thr Phe Thr Ser Tyr
            20                  25                  30

Trp Met Ser Trp Val Arg Gln Ala Pro Gly Lys Gly Leu Glu Leu Val
        35                  40                  45

Ser Ser Ile Thr Ser Tyr Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Thr His Phe Asp Ser Trp Gly Gln Gly Thr Leu
            100                 105                 110

Val Thr Val Ser Ser
            115

<210> SEQ ID NO 29
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 29 gat atc gtg ctg acc cag ccg cct tca gtg agt ggc gca cca ggt cag      48
Asp Ile Val Leu Thr Gln Pro Pro Ser Val Ser Gly Ala Pro Gly Gln
1               5                   10                  15 cgt gtg acc atc tcg tgt agc ggc agc agc agc aac att ggt tct aat      96
Arg Val Thr Ile Ser Cys Ser Gly Ser Ser Ser Asn Ile Gly Ser Asn
            20                  25                  30 tct gtg tct tgg tac cag cag ttg ccc ggg acg gcg ccg aaa ctt ctg     144
Ser Val Ser Trp Tyr Gln Gln Leu Pro Gly Thr Ala Pro Lys Leu Leu
        35                  40                  45 att tat gat aat tct aag cgt ccc tca ggc gtg ccg gat cgt ttt agc     192
Ile Tyr Asp Asn Ser Lys Arg Pro Ser Gly Val Pro Asp Arg Phe Ser
    50                  55                  60 gga tcc aaa agc ggc acc agc gcg agc ctt gcg att acg ggc ctg caa     240
Gly Ser Lys Ser Gly Thr Ser Ala Ser Leu Ala Ile Thr Gly Leu Gln
65                  70                  75                  80 agc gaa gac gaa gcg gat tat tat tgc cag tct cgt gat act tat ggt     288
Ser Glu Asp Glu Ala Asp Tyr Tyr Cys Gln Ser Arg Asp Thr Tyr Gly
                85                  90                  95 tat tat tgg gtg ttt ggc ggc ggc acg aag tta acc gtc cta ggt         333
Tyr Tyr Trp Val Phe Gly Gly Gly Thr Lys Leu Thr Val Leu Gly
            100                 105                 110

<210> SEQ ID NO 30
<211> LENGTH: 111
<212> TYPE: PRT
<213> ORGANISM: Homo sapiens

<400> SEQUENCE: 30

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45
```

| | | | | | | | | | | | | |
|---|---|---|---|---|---|---|---|---|---|---|---|---|
| Ile | Tyr | Asp | Asn | Ser | Lys | Arg | Pro | Ser | Gly | Val | Pro | Asp | Arg | Phe | Ser |
| | | | 50 | | | | 55 | | | | 60 | | | | |
| Gly | Ser | Lys | Ser | Gly | Thr | Ser | Ala | Ser | Leu | Ala | Ile | Thr | Gly | Leu | Gln |
| 65 | | | | | 70 | | | | | 75 | | | | | 80 |
| Ser | Glu | Asp | Glu | Ala | Asp | Tyr | Tyr | Cys | Gln | Ser | Arg | Asp | Thr | Tyr | Gly |
| | | | | 85 | | | | | 90 | | | | | 95 | |
| Tyr | Tyr | Trp | Val | Phe | Gly | Gly | Gly | Thr | Lys | Leu | Thr | Val | Leu | Gly | |
| | | | 100 | | | | | 105 | | | | | 110 | | |

<210> SEQ ID NO 31
<211> LENGTH: 993
<212> TYPE: DNA
<213> ORGANISM: Homo sapiens
<220> FEATURE:
<221> NAME/KEY: CDS
<222> LOCATION: (1)..(993)

<400> SEQUENCE: 31

```
gcc tcc acc aag ggt cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgg gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag     720
Gln Pro Arg Glu Pro Gln Val Tyr Thr Leu Pro Pro Ser Arg Asp Glu
```

| | | | | | | | | | | | | |
|---|---|---|---|---|---|---|---|---|---|---|---|---|
| Gln | Pro | Arg | Glu | Pro | Gln | Val | Tyr | Thr | Leu | Pro | Pro | Ser | Arg | Asp | Glu |
| 225 | | | | 230 | | | | | 235 | | | | | 240 | |

| ctg | acc | aag | aac | cag | gtc | agc | ctg | acc | tgc | ctg | gtc | aaa | ggc | ttc | tat | 768 |
|---|---|---|---|---|---|---|---|---|---|---|---|---|---|---|---|---|
| Leu | Thr | Lys | Asn | Gln | Val | Ser | Leu | Thr | Cys | Leu | Val | Lys | Gly | Phe | Tyr | |
| | | | 245 | | | | | 250 | | | | | 255 | | | |

| ccc | agc | gac | atc | gcc | gtg | gag | tgg | gag | agc | aat | ggg | cag | ccg | gag | aac | 816 |
|---|---|---|---|---|---|---|---|---|---|---|---|---|---|---|---|---|
| Pro | Ser | Asp | Ile | Ala | Val | Glu | Trp | Glu | Ser | Asn | Gly | Gln | Pro | Glu | Asn | |
| | | | 260 | | | | | 265 | | | | | 270 | | | |

| aac | tac | aag | acc | acg | cct | ccc | gtg | ctg | gac | tcc | gac | ggc | tcc | ttc | ttc | 864 |
|---|---|---|---|---|---|---|---|---|---|---|---|---|---|---|---|---|
| Asn | Tyr | Lys | Thr | Thr | Pro | Pro | Val | Leu | Asp | Ser | Asp | Gly | Ser | Phe | Phe | |
| | | 275 | | | | | 280 | | | | | 285 | | | | |

| ctc | tac | agc | aag | ctc | acc | gtg | gac | aag | agc | agg | tgg | cag | cag | ggg | aac | 912 |
|---|---|---|---|---|---|---|---|---|---|---|---|---|---|---|---|---|
| Leu | Tyr | Ser | Lys | Leu | Thr | Val | Asp | Lys | Ser | Arg | Trp | Gln | Gln | Gly | Asn | |
| | 290 | | | | | 295 | | | | | 300 | | | | | |

| gtc | ttc | tca | tgc | tcc | gtg | atg | cat | gag | gct | ctg | cac | aac | cac | tac | acg | 960 |
|---|---|---|---|---|---|---|---|---|---|---|---|---|---|---|---|---|
| Val | Phe | Ser | Cys | Ser | Val | Met | His | Glu | Ala | Leu | His | Asn | His | Tyr | Thr | |
| 305 | | | | | 310 | | | | | 315 | | | | | 320 | |

| cag | aag | agc | ctc | tcc | ctg | tct | ccg | ggt | aaa | tga | | | | | | 993 |
|---|---|---|---|---|---|---|---|---|---|---|---|---|---|---|---|---|
| Gln | Lys | Ser | Leu | Ser | Leu | Ser | Pro | Gly | Lys | | | | | | | |
| | | | 325 | | | | | 330 | | | | | | | | |

<210> SEQ ID NO 32
<211> LENGTH: 330
<212> TYPE: PRT
<213> ORGANISM: Homo sapiens

<400> SEQUENCE: 32

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |

| Ser | Thr | Ser | Gly | Gly | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| | 50 | | | | | 55 | | | | | 60 | | | | |

| Leu | Ser | Ser | Val | Val | Thr | Val | Pro | Ser | Ser | Ser | Leu | Gly | Thr | Gln | Thr |
|---|---|---|---|---|---|---|---|---|---|---|---|---|---|---|---|
| 65 | | | | | 70 | | | | | 75 | | | | | 80 |

| Tyr | Ile | Cys | Asn | Val | Asn | His | Lys | Pro | Ser | Asn | Thr | Lys | Val | Asp | Lys |
|---|---|---|---|---|---|---|---|---|---|---|---|---|---|---|---|
| | | | 85 | | | | | 90 | | | | | 95 | | |

| Lys | Val | Glu | Pro | Lys | Ser | Cys | Asp | Lys | Thr | His | Thr | Cys | Pro | Pro | Cys |
|---|---|---|---|---|---|---|---|---|---|---|---|---|---|---|---|
| | | | 100 | | | | | 105 | | | | | 110 | | |

| Pro | Ala | Pro | Glu | Leu | Leu | Gly | Gly | Pro | Ser | Val | Phe | Leu | Phe | Pro | Pro |
|---|---|---|---|---|---|---|---|---|---|---|---|---|---|---|---|
| | | 115 | | | | | 120 | | | | | 125 | | | |

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| | 130 | | | | | 135 | | | | | 140 | | | | |

| Val | Val | Val | Asp | Val | Ser | His | Glu | Asp | Pro | Glu | Val | Lys | Phe | Asn | Trp |
|---|---|---|---|---|---|---|---|---|---|---|---|---|---|---|---|
| 145 | | | | | 150 | | | | | 155 | | | | | 160 |

| Tyr | Val | Asp | Gly | Val | Glu | Val | His | Asn | Ala | Lys | Thr | Lys | Pro | Arg | Glu |
|---|---|---|---|---|---|---|---|---|---|---|---|---|---|---|---|
| | | | | 165 | | | | | 170 | | | | | 175 | |

| Glu | Gln | Tyr | Asn | Ser | Thr | Tyr | Arg | Val | Val | Ser | Val | Leu | Thr | Val | Leu |
|---|---|---|---|---|---|---|---|---|---|---|---|---|---|---|---|
| | | | 180 | | | | | 185 | | | | | 190 | | |

| His | Gln | Asp | Trp | Leu | Asn | Gly | Lys | Glu | Tyr | Lys | Cys | Lys | Val | Ser | Asn |
|---|---|---|---|---|---|---|---|---|---|---|---|---|---|---|---|
| | | 195 | | | | | 200 | | | | | 205 | | | |

| Lys | Ala | Leu | Pro | Ala | Pro | Ile | Glu | Lys | Thr | Ile | Ser | Lys | Ala | Lys | Gly |
|---|---|---|---|---|---|---|---|---|---|---|---|---|---|---|---|
| | 210 | | | | | 215 | | | | | 220 | | | | |

| Gln | Pro | Arg | Glu | Pro | Gln | Val | Tyr | Thr | Leu | Pro | Pro | Ser | Arg | Asp | Glu |
|---|---|---|---|---|---|---|---|---|---|---|---|---|---|---|---|
| 225 | | | | | 230 | | | | | 235 | | | | | 240 |

```
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 33
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 33 cag ccc aag gct gcc ccc tcg gtc act ctg ttc ccg ccc tcc tct gag      48
Gln Pro Lys Ala Ala Pro Ser Val Thr Leu Phe Pro Pro Ser Ser Glu
1               5                   10                  15 gag ctt caa gcc aac aag gcc aca ctg gtg tgt ctc ata agt gac ttc      96
Glu Leu Gln Ala Asn Lys Ala Thr Leu Val Cys Leu Ile Ser Asp Phe
            20                  25                  30 tac ccg gga gcc gtg aca gtg gcc tgg aag gga gat agc agc ccc gtc     144
Tyr Pro Gly Ala Val Thr Val Ala Trp Lys Gly Asp Ser Ser Pro Val
        35                  40                  45 aag gcg gga gtg gag acc acc aca ccc tcc aaa caa agc aac aac aag     192
Lys Ala Gly Val Glu Thr Thr Thr Pro Ser Lys Gln Ser Asn Asn Lys
    50                  55                  60 tac gcg gcc agc agc tat ctg agc ctg acg cct gag cag tgg aag tcc     240
Tyr Ala Ala Ser Ser Tyr Leu Ser Leu Thr Pro Glu Gln Trp Lys Ser
65                  70                  75                  80 cac aga agc tac agc tgc cag gtc acg cat gaa ggg agc acc gtg gag     288
His Arg Ser Tyr Ser Cys Gln Val Thr His Glu Gly Ser Thr Val Glu
                85                  90                  95 aag aca gtg gcc cct aca gaa tgt tca tag                             318
Lys Thr Val Ala Pro Thr Glu Cys Ser
            100                 105

<210> SEQ ID NO 34
<211> LENGTH: 105
<212> TYPE: PRT
<213> ORGANISM: Homo sapiens

<400> SEQUENCE: 34

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Gly Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80
```

His Arg Ser Tyr Ser Cys Gln Val Thr His Glu Gly Ser Thr Val Glu
            85                  90                  95

Lys Thr Val Ala Pro Thr Glu Cys Ser
            100                 105

<210> SEQ ID NO 35
<211> LENGTH: 452
<212> TYPE: PRT
<213> ORGANISM: Homo sapiens

<400> SEQUENCE: 35

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

```
Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly Lys
    450

<210> SEQ ID NO 36
<211> LENGTH: 214
<212> TYPE: PRT
<213> ORGANISM: Homo sapiens

<400> SEQUENCE: 36

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Thr Leu Asp Ile Phe
                85                  90                  95

Asn Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 37
<211> LENGTH: 452
<212> TYPE: PRT
<213> ORGANISM: Homo sapiens

<400> SEQUENCE: 37

Gln Val Glu Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
            35                  40                  45

Ser Gly Ile Ser Gly Trp Ser Trp Thr Tyr Tyr Ala Asp Ser Val
50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
            85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

Met His Glu Ala Leu His Asn His Tyr Thr Gln Lys Ser Leu Ser Leu
        435                 440                 445

Ser Pro Gly Lys
    450

<210> SEQ ID NO 38
<211> LENGTH: 214
<212> TYPE: PRT
<213> ORGANISM: Homo sapiens

<400> SEQUENCE: 38

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Phe Pro Lys Phe
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 39
<211> LENGTH: 447
<212> TYPE: PRT
<213> ORGANISM: Homo sapiens

<400> SEQUENCE: 39

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Trp Met Ser Trp Val Arg Gln Ala Pro Gly Lys Gly Leu Glu Leu Val
        35                  40                  45

Ser Ser Ile Thr Ser Tyr Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95
Ala Arg Asn Met Tyr Thr His Phe Asp Ser Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 40
<211> LENGTH: 216
<212> TYPE: PRT
<213> ORGANISM: Homo sapiens

<400> SEQUENCE: 40

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn

```
                    20                  25                  30
Ser Val Ser Trp Tyr Gln Gln Leu Pro Gly Thr Ala Pro Lys Leu Leu
            35                  40                  45
Ile Tyr Asp Asn Ser Lys Arg Pro Ser Gly Val Pro Asp Arg Phe Ser
        50                  55                  60
Gly Ser Lys Ser Gly Thr Ser Ala Ser Leu Ala Ile Thr Gly Leu Gln
 65                  70                  75                  80
Ser Glu Asp Glu Ala Asp Tyr Tyr Cys Gln Ser Arg Asp Thr Tyr Gly
                85                  90                  95
Tyr Tyr Trp Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Gly Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 41
<211> LENGTH: 17
<212> TYPE: PRT
<213> ORGANISM: Homo sapiens

<400> SEQUENCE: 41

Leu Cys Gly Ala Glu Leu Val Asp Ala Leu Gln Phe Val Cys Gly Asp
 1               5                  10                  15

Arg

<210> SEQ ID NO 42
<211> LENGTH: 13
<212> TYPE: PRT
<213> ORGANISM: Homo sapiens

<400> SEQUENCE: 42

Cys Cys Phe Arg Ser Cys Asp Leu Arg Arg Leu Glu Met
 1               5                  10

<210> SEQ ID NO 43
<211> LENGTH: 70
<212> TYPE: PRT
<213> ORGANISM: Homo sapiens

<400> SEQUENCE: 43

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
```

-continued

```
            50                  55                  60
Lys Pro Ala Lys Ser Ala
65                  70
```